US011078491B2

(12) United States Patent
Chen et al.

(10) Patent No.: US 11,078,491 B2
(45) Date of Patent: Aug. 3, 2021

(54) VACCINES AGAINST ZIKA VIRUS BASED ON ZIKA STRUCTURE PROTEINS

(71) Applicant: ARIZONA BOARD OF REGENTS ON BEHALF OF ARIZONA STATE UNIVERSITY, Scottsdale, AZ (US)

(72) Inventors: Qiang Chen, Chandler, AZ (US); Haiyan Sun, Tempe, AZ (US); Huafang Lai, Chandler, AZ (US); Ming Yang, Chandler, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 0 days.

(21) Appl. No.: 15/989,060

(22) Filed: May 24, 2018

(65) Prior Publication Data
US 2018/0340181 A1 Nov. 29, 2018

Related U.S. Application Data

(60) Provisional application No. 62/510,396, filed on May 24, 2017.

(51) Int. Cl.
| A61K 39/12 | (2006.01) |
| A61P 31/14 | (2006.01) |
| C12N 15/74 | (2006.01) |
| G01N 33/569 | (2006.01) |
| C12N 15/82 | (2006.01) |
| A61K 39/00 | (2006.01) |

(52) U.S. Cl.
CPC .......... *C12N 15/8258* (2013.01); *A61K 39/12* (2013.01); *C12N 15/743* (2013.01); *G01N 33/56983* (2013.01); *A61K 2039/5258* (2013.01); *A61K 2039/53* (2013.01); *A61K 2039/55505* (2013.01); *A61K 2039/55561* (2013.01); *A61P 31/14* (2018.01); *C12N 2730/10023* (2013.01); *C12N 2770/24122* (2013.01); *C12N 2770/24123* (2013.01); *C12N 2770/24134* (2013.01); *C12N 2770/24151* (2013.01); *G01N 2333/185* (2013.01)

(58) Field of Classification Search
None
See application file for complete search history.

(56) References Cited

U.S. PATENT DOCUMENTS

| 8,513,397 | B2 | 8/2013 | Mason | |
| 8,663,950 | B2 | 3/2014 | Chen | |
| 9,499,608 | B2 | 11/2016 | Chen | |
| 9,506,079 | B2 | 11/2016 | Mason | |
| 2017/0275639 | A1 | 9/2017 | Chen | |
| 2017/0298119 | A1* | 10/2017 | Wollacott | .............. C07K 16/10 |

FOREIGN PATENT DOCUMENTS

| WO | 2010025285 A1 | 3/2010 |
| WO | 2011085289 A1 | 7/2011 |
| WO | 2013006244 A1 | 1/2013 |
| WO | 2015113055 A2 | 7/2015 |
| WO | 2018226506 A1 | 12/2018 |

OTHER PUBLICATIONS

Shan et al., Cell Host Microbe., Jul. 2018, 24(1):12-17. (Year: 2018).*
Boigard et al., PLoS Negl Trap Dis, May 8, 2017, 11(5): e0005608. (Year: 2017).*
Abbink P., et al (2016) Protective efficacy of multiple vaccine platforms against Zika virus challenge in rhesus monkeys. Science, 353, 1129.
Attar N. (2016) ZIKA virus circulates in new regions. Nat. Rev. Microbiol. 14, 62-62.
Barba-Spaeth, G., et al. (2016). "Structural basis of potent Zika-dengue virus antibody cross-neutralization." Nature 536(7614): 48-53.
Belmusto-Worn V.E., et al (2005) Randomized, double-blind, phase III. Pivotal field trial of the comparative immunogenicity, safety, and tolerability of two yellow fever 17D vaccines (ARILVAX™ and YF-VAX™) in healthy infant and children in Peru. Am. J. Trop. Med. Hyg. 72, 189-197.
Beltramello, M., et al. (2010). "The Human Immune Response to Dengue Virus Is Dominated by Highly Cross-Reactive Antibodies Endowed with Neutralizing and Enhancing Activity." Cell Host & Microbe 8(3): 271-281.
Billaud, J. N., et al. (2007). "Advantages to the use of rodent hepadnavirus core proteins as vaccine platforms." Vaccine 25(9): 1593-1606.
Brown, A. L., et al. (1991). "Foreign epitopes in immunodominant regions of hepatitis B core particles are highly immunogenic and conformationally restricted." Vaccine 9(8): 595-601.
Cao-Lormeau V.-M., et al (2016) Guillain-Barré Syndrome outbreak associated with Zika virus infection in French Polynesia: a case-control study. Lancet, 387, 1531-1539.
Chan, H.-T., et al. (2016) Cold chain and virus-free chloroplast-made booster vaccine to confer immunity against different poliovirus serotypes. Plant Biotechnol. J. 14, 2190-2200.
Chen Q. (2008) Expression and purification of pharmaceutical proteins in plants. Biol. Eng. 1, 291-321.

(Continued)

*Primary Examiner* — Nicole Kinsey White
(74) *Attorney, Agent, or Firm* — Quarles & Brady LLP

(57) ABSTRACT

Compositions including a virus-like particle (VLP)-based vaccine displaying a portion of ZIKV envelope protein (E) domain III (DIII) and a portion of ZIKV envelope protein (E) and related methods are disclosed herein. Further, compositions including vaccines comprising a portion of ZIKA virus E protein, wherein the portion of ZIKA virus E protein is either a full-length version of ZIKA virus E protein or a functionally equivalent version of the full-length ZIKA virus E protein, are disclosed.

11 Claims, 17 Drawing Sheets
Specification includes a Sequence Listing.

(56) References Cited

OTHER PUBLICATIONS

Chen Q. (2011) Expression and manufacture of pharmaceutical proteins in genetically engineered horticultural plants in Transgenic Horticultural Crops: Challenges and Opportunities—Essays by Experts(Mou B., editor; and Scorza R., editor. , eds), pp. 83-124. Boca Raton: Taylor & Francis.
Chen Q. (2011) Turning a new leaf. Eur. Biopharm. Rev. 2, 64-68.
Chen Q. et al. (2016) The potential of plants as a system for the development and production of human biologics. F1000Res. 5 https://doi.org/10.12688/f11000research.18010.12681.
Chen Q. et al. (2014) Plant-derived monoclonal antibodies as human biologics for infectious disease and cancer in Plant-derived Pharmaceuticals: Principles and Applications for Developing Countries (Hefferon K.L., editor. , ed), pp. 42-75. Cryodon, UK: CABI.
Chen Q., et al. (2016) Transient protein expression by agroinfiltration in lettuce. Methods Mol. Biol. 1385, 55-67.
Chen, Q. (2013). Virus-like Particle Vaccines for Norovirus Gastroenteritis. Molecular Vaccines. M. Giese. Vienna, Springer, DOI:10.1007/978-3-7091-1419-3_8. 1: 153-181.
Chen, Q. et al. (2013). "Plant-derived virus-like particles as vaccines." Human Vaccines & Immunotherapeutics 9(1): 26-49.
Chen, Q., et al. (2013). "Agroinfiltration as an Effective and Scalable Strategy of Gene Delivery for Production of Pharmaceutical Proteins." Advanced Technolgy in Biology and Medicine 1(1): 103-112.
Chen, Q., et al. (2011). "Geminiviral vectors based on bean yellow dwarf virus for production of vaccine antigens and monoclonal antibodies in plants." Human Vaccines 7(3): 331-338.
Clarke J.L., et al (2017) Lettuce-produced hepatitis C virus E1E2 heterodimer triggers immune responses in mice and antibody production after oral vaccination. Plant Biotechnol. J. https://doi.org/10.1111/pbi.12743.
Clarke J.L., et al. (2013) How can plant genetic engineering contribute to cost-effective fish vaccine development for promoting sustainable aquaculture? Plant Mol. Biol. 83, 33-40.
Coffman, R. L., et al. (2010). "Vaccine Adjuvants: Putting Innate Immunity to Work." Immunity 33(4): 492-503.
Crill, W. D. et al. (2004). "Localization and characterization of flavivirus envelope glycoprotein cross-reactive epitopes." Journal of virology 78(24): 13975-13986.
Dai L., et al (2016) Structures of the Zika virus envelope protein and its complex with a flavivirus broadly protective antibody. Cell Host Microbe, 19, 696-704.
Dejnirattisai, W., et al. (2016). "Dengue virus sero-cross-reactivity drives antibody-dependent enhancement of infection with zika virus." Nat Immunol advance online publication.
Dent M., et al (2016) Plant-produced anti-dengue virus monoclonal antibodies exhibit reduced antibody-dependent enhancement of infection activity. J. Gen. Virol. 97, 3280-3290.
Fulton A., et al. (2015) Purification of monoclonal antibody against Ebola GP1 protein expressed in Nicotiana benthamiana. J. Chromatogr. A 1389, 128-132.
Genbank Accession No. AMC13911.1 VRL Feb. 1, 2016—accessed online at https://www.ncbi.nlm.nih.gov/protein/AMC13911.1/.
GenBank Accession No. AY632535 VRL Nov. 23, 2010—accessed online at https://www.ncbi.nlm.nih.gov/nuccore/AY632535.2/.
GenBank Accession No. EU545988 VRL Jul. 30, 2008—accessed online at https://www.ncbi.nlm.nih.gov/nuccore/EU545988.1/.
GenBank Accession No. HQ234499 VRL Mar. 19, 2012—accessed online at https://www.ncbi.nlm.nih.gov/nuccore/HQ234499.1/.
GenBank Accession No. JN860885 VRL Mar. 19, 2012—accessed online at https://www.ncbi.nlm.nih.gov/nuccore/JN860885.
GenBank Accession No. KF268948 VRL Dec. 21, 2015—accessed online at https://www.ncbi.nlm.nih.gov/nuccore/KF268948.
GenBank Accession No. KF268949 VRL Dec. 21, 2015—accessed online at https://www.ncbi.nlm.nih.gov/nuccore/KF268949.
GenBank Accession No. KF268950 VRL Dec. 21, 2015—accessed online at https://www.ncbi.nlm.nih.gov/nuccore/KF268950.
GenBank Accession No. KF383115 VRL Mar. 15, 2014—accessed online at https://www.ncbi.nlm.nih.gov/nuccore/KF383115.1/.
GenBank Accession No. KF383116 VRL Mar. 15, 2014—accessed online at https://www.ncbi.nlm.nih.gov/nuccore/KF3831156/.
GenBank Accession No. KF383117 VRL Mar. 15, 2014—accessed online at https://www.ncbi.nlm.nih.gov/nuccore/KF383117/.
GenBank Accession No. KF383118 VRL Mar. 15, 2014—accessed online at https://www.ncbi.nlm.nih.gov/nuccore/KF383118/.
GenBank Accession No. KF383119 VRL Mar. 15, 2014—accessed online at https://www.ncbi.nlm.nih.gov/nuccore/KF383119/.
GenBank Accession No. KF993678 VRL Nov. 6, 2014—accessed online at https://www.ncbi.nlm.nih.gov/nuccore/KF993678.
GenBank Accession No. KJ776791 VRL Aug. 31, 2016—accessed online at https://www.ncbi.nlm.nih.gov/nuccore/KJ776791.
GenBank Accession No. KU321639 VRL Apr. 5, 2016—accessed online at https://www.ncbi.nlm.nih.gov/nuccore/KU321639.
GenBank Accession No. KU501215 VRL Feb. 1, 2016—accessed online at https://www.ncbi.nlm.nih.gov/nuccore/KU501215.
GenBank Accession No. KU501216 VRL Feb. 1, 2016—accessed online at https://www.ncbi.nlm.nih.gov/nuccore/KU501216.
GenBank Accession No. KU501217 VRL Feb. 1, 2016—accessed online at https://www.ncbi.nlm.nih.gov/nuccore/KU501217.
Giritch A., et al. (2006) Rapid high-yield expression of full-size IgG antibodies in plants coinfected with noncompeting viral vectors. Proc. Natl Acad. Sci. USA, 103, 14701-14706.
Halstead, S. B. (2014). "Dengue Antibody-Dependent Enhancement: Knowns and Unknowns." Microbiol Spectr 2 (6).
Hasan S.S., et al (2017) A human antibody against Zika virus crosslinks the E protein to prevent infection. Nat. Commun. 8, 14722.
He J., et al. (2012) A novel system for rapid and cost-effective production of detection and diagnostic reagents of West Nile virus in plants. J. Biomed. Biotechnol. 2012, 1-10.
He J., et al (2014) Generation and analysis of novel plant-derived antibody-based therapeutic molecules against West Nile virus. PLoS One, 9, e93541 https://doi.org/93510.91371/journal.pone.0093541.
He J., et al. (2014) A plant-produced antigen elicits potent immune responses against West Nile virus in mice. Biomed. Res. Int. 2014, 10.
Heinz F.X., et al.. (2007) Field effectiveness of vaccination against tick-borne encephalitis. Vaccine, 25, 7559-7567.
Hombach J., et al. (2005) Report on a WHO consultation on immunological endpoints for evaluation of new Japanese encephalitis vaccines, WHO, Geneva, Sep. 2-3, 2004. Vaccine, 23, 5205-5211.
Huang, Z., et al. (2009). "A DNA replicon system for rapid high-level production of virus-like particles in plants." Biotechnology and bioengineering 103(4): 706-714.
Jungblut, M., et al. (2008). "Preparation of Single-Cell Suspensions from Mouse Spleen with the gentleMACS Dissociator." (22): e1029.
Kostyuchenko V.A., et al (2016) Structure of the thermally stable Zika virus. Nature, 533,425-428.
Kreil T.R., et al. (1997) Antibodies protect mice against challenge with tick-borne encephalitis virus (TBEV)-infected macrophages. Clin. Exp. Immunol. 110, 358-361.
Kwon K.-C. et al. (2015) Low-cost oral delivery of protein drugs bioencapsulated in plant cells. Plant Biotechnol. J. 13, 1017-1022.
Lai H., et al (2010) Monoclonal antibody produced in plants efficiently treats West Nile virus infection in mice. Proc. Natl Acad. Sci. USA, 107, 2419-2424.
Lai H.,et al. (2012) Robust production of virus-like particles and monoclonal antibodies with geminiviral replicon vectors in lettuce. Plant Biotechnol. J. 10, 95-104.
Lai H., et al (2014) Structural and functional characterization of an anti-West Nile virus monoclonal antibody and its single-chain variant produced in glycoengineered plants. Plant Biotechnol. J. 12, 1098-1107.
Lai, H. et al. (2012). "Bioprocessing of plant-derived virus-like particles of Norwalk virus capsid protein under current Good Manufacture Practice regulations." Plant Cell Reports 31(3): 573-584.
Larocca R.A., et al (2016) Vaccine protection against Zika virus from Brazil. Nature, 536, 474-478.
Lazear H.M. et al. (2016) Zika virus: new clinical syndromes and its emergence in the western hemisphere. J. Virol. 90, 4864-4875.

(56) References Cited

OTHER PUBLICATIONS

Leuzinger, K., et al. (2013). "Efficient Agroinfiltration of Plants for High-level Transient Expression of Recombinant Proteins." Journal of Visualized Experiments(77): doi:10.3791/50521.

Lin, H. E., et al. (2012). "Analysis of epitopes on dengue virus envelope protein recognized by monoclonal antibodies and polyclonal human sera by a high throughput assay." PLoS Negl Trop Dis 6(1): e1447.

Lindblad E.B. (2004) Aluminium compounds for use in vaccines. Immunol. Cell Biol. 82, 497-505.

Liu G., et al (2015) Immunogenicity and efficacy of flagellin-envelope fusion dengue vaccines in mice and monkeys. Clin. Vaccine Immunol. 22, 516-525.

Martin R.M., et al. (1998) The need for IgG2c specific antiserum when isotyping antibodies from C57BL/6 and NOD mice. J. lmmunol. Methods, 212, 187-192.

Mason R.A., et al. (1973) Yellow fever vaccine: direct challenge of monkeys given graded doses of 17D vaccine. Appl. Microbiol. 25, 539-544.

Morens, D. M. (1994). "Antibody-dependent of enhancement of infection and the pathogenesis of viral disease." Clin Inf Dis 19: 500-512.

Moyle P.M. et al. (2013) Modern subunit vaccines: development, components, and research opportunities. ChemMedChem, 8, 360-376.

Nandi S., et al.. (2016) Techno-economic analysis of a transient plant-based platform for monoclonal antibody production. mAbs, 8, 1456-1466.

Oliphant, T., et al. (2005). "Development of a humanized monoclonal antibody with therapeutic potential against West Nile virus." Nature Medicine 11(5): 522-530.

Pardi, N. et al. (2017). Nucleoside Modified mRNA Vaccines for Infectious Diseases. RNA Vaccines: Methods and Protocols. T Kramps and K. Elbers. New York, NY, Springer New York: 109-121.

Phoolcharoen W., et al(2011) A nonreplicating subunit vaccine protects mice against lethal Ebola virus challenge. Proc. Natl Acad. Sci. USA, 108, 20695-20700.

Richner J.M., et al (2017) Modified mRNA vaccines protect against Zika virus infection. Cell, 168(1114-1125), e1110.

Samarasekera, U. et al. (2016). "Concern over Zika virus grips the world." The Lancet 387(10018): 521-524.

Santi, L., et al. (2008). "An efficient plant viral expression system generating orally immunogenic Norwalk virus-like particles." Vaccine 26(15): 1846-1854.

Schijns, V. E. "Immunological concepts of vaccine adjuvant activity." Current opinion in immunology 12.4 (2000): 456.

Sirohi, D., et al (2016). "The 3.8 Å resolution cryo-EM structure of Zika virus." Science 352(6284): 467-470.

Stettler, K., et al (2016). "Specificity, cross-reactivity, and function of antibodies elicited by Zika virus infection." Science 353(6301): 823.

Sukupolvi-Petty, S., et al (2010). "Structure and Function Analysis of Therapeutic Monoclonal Antibodies against Dengue Virus Type 2." J. Virol. 84(18): 9227-9239.

Suthar, M. S., et al (2013). "Innate Immune Sensing of Flaviviruses." PLOS Pathogens 9(9): e1003541.

Tuse D., et al. (2014) Manufacturing economics of plant-made biologics: case studies in therapeutic and industrial enzymes. Biomed. Res. Int. 2014, 10.

Ulrich, R., et al (1998). "Core particles of hepatitis B virus as carrier for foreign epitopes." Adv Virus Res 50: 141-182.

Whitacre, D. C., et al (2009). "Use of hepadnavirus core proteins as vaccine platforms." Expert Review of Vaccines 3(11): 1565-1573.

Yang M., et al. (2017) Immunization of Zika virus envelope protein domain III induces specific and neutralizing immune responses against Zika virus. Vaccine, 35, 4287-4294.

Zhang S., et al (2016) Neutralization mechanism of a highly potent antibody against Zika virus. Nat. Commun. 7, 13679.

Zhao H., et al (2016) Structural basis of Zika virus-specific antibody protection. Cell, 166, 1016-1027.

\* cited by examiner

Fig. 11

SEQUENCE LISTING

```
<160> NUMBER OF SEQ ID NOS: 17

<210> SEQ ID NO 1
<211> LENGTH: 93
<212> TYPE: PRT
<213> ORGANISM: artificial sequence
<220> FEATURE:
<223> OTHER INFORMATION: synthetic

<400> SEQUENCE: 1

Ala Phe Thr Phe Thr Lys Ile Pro Ala Glu Thr Leu His Gly Thr Val
1               5                   10                  15

Thr Val Glu Val Gln Tyr Ala Gly Thr Asp Gly Pro Cys Lys Val Pro
            20                  25                  30

Ala Gln Met Ala Val Asp Met Gln Thr Leu Thr Pro Val Gly Arg Leu
        35                  40                  45

Ile Thr Ala Asn Pro Val Ile Thr Glu Ser Thr Glu Asn Ser Lys Met
    50                  55                  60

Met Leu Glu Leu Asp Pro Pro Phe Gly Asp Ser Tyr Ile Val Ile Gly
65                  70                  75                  80

Val Gly Glu Lys Lys Ile Thr His His Trp His Arg Ser
                85                  90

<210> SEQ ID NO 2
<211> LENGTH: 155
<212> TYPE: PRT
<213> ORGANISM: artificial sequence
<220> FEATURE:
<223> OTHER INFORMATION: synthetic

<400> SEQUENCE: 2

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Glu Asp Pro Ala
65                  70                  75                  80
```

Ser Arg Asp Leu Val Val Asn Tyr Val Asn Thr Asn Val Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Asp Arg Gly
145                 150                 155

<210> SEQ ID NO 3
<211> LENGTH: 18
<212> TYPE: DNA
<213> ORGANISM: artificial sequence
<220> FEATURE:
<223> OTHER INFORMATION: synthetic

<400> SEQUENCE: 3
gtttcttact ctctttgc                                              18

<210> SEQ ID NO 4
<211> LENGTH: 29
<212> TYPE: DNA
<213> ORGANISM: artificial sequence
<220> FEATURE:
<223> OTHER INFORMATION: synthetic

<400> SEQUENCE: 4
aggagctctc aagatccaaa atcccaagc                                  29

<210> SEQ ID NO 5
<211> LENGTH: 21
<212> TYPE: DNA
<213> ORGANISM: artificial sequence
<220> FEATURE:
<223> OTHER INFORMATION: synthetic

<400> SEQUENCE: 5
accatggaca ttgacccta c                                           21

<210> SEQ ID NO 6
<211> LENGTH: 36
<212> TYPE: DNA
<213> ORGANISM: artificial sequence
<220> FEATURE:
<223> OTHER INFORMATION: synthetic

<400> SEQUENCE: 6
gcaaagagag taagaaacac ccctgtccct tcttcg                          36

<210> SEQ ID NO 7
<211> LENGTH: 93
<212> TYPE: PRT
<213> ORGANISM: artificial sequence
<220> FEATURE:
<223> OTHER INFORMATION: synthetic

<400> SEQUENCE: 7

Ala Phe Thr Phe Thr Lys Val Pro Ala Glu Thr Leu His Gly Thr Val
1               5                   10                  15

Thr Val Glu Val Gln Tyr Ala Gly Thr Asp Gly Pro Cys Lys Val Pro
            20                  25                  30

```
Ala Gln Met Ala Val Asp Met Gln Thr Leu Thr Pro Val Gly Arg Leu
            35                  40                  45

Ile Thr Ala Asn Pro Val Ile Thr Glu Ser Thr Glu Asn Ser Lys Met
 50                      55                  60

Met Leu Glu Leu Asp Pro Pro Phe Gly Asp Ser Tyr Ile Val Ile Gly
 65                  70                  75                  80

Val Gly Asp Lys Lys Ile Thr His His Trp His Arg Ser
                85                  90
```

<210> SEQ ID NO 8
<211> LENGTH: 93
<212> TYPE: PRT
<213> ORGANISM: Artificial sequence
<220> FEATURE:
<223> OTHER INFORMATION: synthetic

<400> SEQUENCE: 8

```
Ala Phe Thr Phe Thr Lys Val Pro Ala Glu Thr Leu His Gly Thr Val
 1               5                  10                  15

Thr Val Glu Val Gln Tyr Ala Gly Arg Asp Gly Pro Cys Lys Val Pro
            20                  25                  30

Ala Gln Met Ala Val Asp Met Gln Thr Leu Thr Pro Val Gly Arg Leu
            35                  40                  45

Ile Thr Ala Asn Pro Val Ile Thr Glu Ser Thr Glu Asn Ser Lys Met
 50                      55                  60

Met Leu Glu Leu Asp Pro Pro Phe Gly Asp Ser Tyr Ile Val Ile Gly
 65                  70                  75                  80

Val Gly Asp Lys Lys Ile Thr His His Trp His Arg Ser
                85                  90
```

<210> SEQ ID NO 9
<211> LENGTH: 93
<212> TYPE: PRT
<213> ORGANISM: Artificial sequence
<220> FEATURE:
<223> OTHER INFORMATION: synthetic

<400> SEQUENCE: 9

```
Ala Phe Thr Phe Thr Lys Val Pro Ala Glu Thr Leu His Gly Thr Val
 1               5                  10                  15

Thr Val Glu Val Gln Tyr Ala Gly Thr Asp Gly Pro Cys Lys Ile Pro
            20                  25                  30

Val Gln Met Ala Val Asp Met Gln Thr Leu Thr Pro Val Gly Arg Leu
            35                  40                  45

Ile Thr Ala Asn Pro Val Ile Thr Glu Ser Thr Glu Asn Ser Lys Met
 50                      55                  60

Met Leu Glu Leu Asp Pro Pro Phe Gly Asp Ser Tyr Ile Val Ile Gly
 65                  70                  75                  80

Val Gly Asp Lys Lys Ile Thr His His Trp His Arg Ser
                85                  90
```

<210> SEQ ID NO 10
<211> LENGTH: 93
<212> TYPE: PRT
<213> ORGANISM: Artificial sequence
<220> FEATURE:
<223> OTHER INFORMATION: synthetic
<220> FEATURE:
<221> NAME/KEY: misc_feature
<222> LOCATION: (91)..(91)
<223> OTHER INFORMATION: Xaa can be any naturally occurring amino acid

```
<400> SEQUENCE: 10

Ala Phe Thr Phe Thr Lys Ile Pro Ala Glu Thr Leu His Gly Thr Val
1               5                   10                  15

Thr Val Glu Val Gln Tyr Ala Gly Thr Asp Gly Pro Cys Lys Val Pro
            20                  25                  30

Ala Gln Met Ala Val Asp Met Gln Thr Leu Thr Pro Val Gly Arg Leu
        35                  40                  45

Ile Thr Ala Asn Pro Val Ile Thr Glu Ser Thr Glu Asn Ser Lys Met
    50                  55                  60

Met Leu Glu Leu Asp Pro Pro Phe Gly Asp Ser Tyr Ile Val Ile Gly
65                  70                  75                  80

Val Gly Asp Lys Lys Ile Thr His His Trp Xaa Arg Ser
                85                  90

<210> SEQ ID NO 11
<211> LENGTH: 93
<212> TYPE: PRT
<213> ORGANISM: Artificial sequence
<220> FEATURE:
<223> OTHER INFORMATION: synthetic

<400> SEQUENCE: 11

Ala Phe Thr Phe Thr Lys Ile Pro Ala Glu Thr Leu His Gly Thr Val
1               5                   10                  15

Thr Val Glu Val Gln Tyr Ala Gly Thr Asp Gly Pro Cys Lys Val Pro
            20                  25                  30

Ala Gln Met Ala Val Asp Met Gln Thr Leu Thr Pro Val Gly Arg Leu
        35                  40                  45

Ile Thr Ala Asn Pro Val Ile Thr Glu Ser Thr Glu Asn Ser Lys Met
    50                  55                  60

Met Leu Glu Leu Asp Pro Pro Phe Gly Asp Ser Tyr Ile Val Ile Gly
65                  70                  75                  80

Ile Gly Glu Lys Lys Ile Thr His His Trp His Arg Ser
                85                  90

<210> SEQ ID NO 12
<211> LENGTH: 93
<212> TYPE: PRT
<213> ORGANISM: artificial sequence
<220> FEATURE:
<223> OTHER INFORMATION: synthetic

<400> SEQUENCE: 12

Ala Phe Thr Phe Thr Lys Ile Pro Ala Glu Thr Leu His Gly Thr Val
1               5                   10                  15

Thr Val Glu Val Gln Tyr Ala Gly Thr Asp Gly Pro Cys Lys Val Pro
            20                  25                  30

Ala Gln Met Ala Val Asp Met Gln Thr Leu Thr Pro Val Gly Arg Leu
        35                  40                  45

Ile Thr Ala Asn Pro Val Ile Thr Glu Gly Thr Glu Asn Ser Lys Met
    50                  55                  60

Met Leu Glu Leu Asp Pro Pro Phe Gly Asp Ser Tyr Ile Val Ile Gly
65                  70                  75                  80

Val Gly Glu Lys Lys Ile Thr His His Trp His Arg Ser
                85                  90

<210> SEQ ID NO 13
```

<211> LENGTH: 433
<212> TYPE: PRT
<213> ORGANISM: Artificial sequence
<220> FEATURE:
<223> OTHER INFORMATION: synthetic

<400> SEQUENCE: 13

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser

<210> SEQ ID NO 14
<211> LENGTH: 433
<212> TYPE: PRT
<213> ORGANISM: Artificial sequence
<220> FEATURE:
<223> OTHER INFORMATION: synthetic

<400> SEQUENCE: 14

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Arg Glu Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Arg Gly Asn Gly Cys Gly Arg Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

```
Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser
```

<210> SEQ ID NO 15
<211> LENGTH: 1299
<212> TYPE: DNA
<213> ORGANISM: Artificial sequence
<220> FEATURE:
<223> OTHER INFORMATION: synthetic

<400> SEQUENCE: 15

```
attaggtgta ttggagtttc taatagagat tttgtggaag gaatgtctgg aggaacttgg      60
gttgatgttg ttcttgaaca tggaggatgt gttactgtta tggctcaaga taagccaact     120
gttgatattg agcttgttac tactactgtt tctaacatgg ctgaggttag gtcttactgt     180
tatgaggctt ctatttctga catggcttct gattcaaggt gtccaactca gggagaggct     240
tatcttgata agcagtctga tactcaatat gtttgtaaga gaactcttgt tgatagagga     300
tggggaaacg gatgtggact tttcggaaag ggatctcttg tgacttgtgc aagttcgct     360
tgttctaaga gatgactgg aaagtctatt cagccagaaa atcttgagta tagaattatg     420
cttttctgttc acggatctca acattctgga atgattgtta acgatactgg acacgaaact     480
gacgagaata gagctaaggt tgaaattact ccaaattctc caagagctga agctactctt     540
ggaggatttg gatctcttgg acttgattgt gagccaagaa ctggacttga tttttctgat     600
ctttattatc ttactatgaa caacaaacat tggcttgttc ataaggaatg gtttcatgat     660
attccacttc cttggcatgc tggagctgat actggaactc cacattggaa caacaaggaa     720
gctcttgttg agttcaagga tgctcatgct aagagacaaa ctgttgttgt tcttggatct     780
caagaaggag ctgttcatac tgctcttgct ggtgctcttg aagctgagat ggatggagct     840
aagggaaggc tttcttctgg acaccttaag tgcagactta agatggacaa acttagactt     900
aagggagttt cttactctct ttgcactgct gctttcactt ttactaagat tccagctgaa     960
actcttcatg gaactgtgac tgtggaagtt caatatgctg gaactgatgg accatgtaag    1020
gttccagctc aaatggctgt ggatatgcag actcttactc cagttggaag gcttattact    1080
gctaacccag ttattactga gtctactgaa aactctaaga tgatgcttga gcttgatcca    1140
ccattcggag attcttacat tgttattgga gttggagaaa agaagattac tcatcattgg    1200
cataggtctg gatctactat tggaaaggct tttgaagcta ctgttagagg agctaagaga    1260
atggctgttc ttggagatac tgcttgggat tttggatct                           1299
```

<210> SEQ ID NO 16
<211> LENGTH: 1335
<212> TYPE: DNA
<213> ORGANISM: Artificial sequence
<220> FEATURE:
<223> OTHER INFORMATION: synthetic

<400> SEQUENCE: 16

```
caccaccacc accaccacat taggtgtatt ggagtttcta atagagattt tgtggaagga      60
atgtctggag gaacttgggt tgatgttgtt cttgaacatg gaggatgtgt tactgttatg     120
gctcaagata agccaactgt tgatattgag cttgttacta ctactgtttc taacatggct     180
gaggttaggt cttactgtta tgaggcttct atttctgaca tggcttctga ttcaaggtgt     240
ccaactcagg gagaggctta tcttgataag cagtctgata ctcaatatgt ttgtaagaga     300
actcttgttg atagaggatg gggaaacgga tgtggacttt cggaaaggg atctcttgtg      360
acttgtgcta gttcgcttg ttctaagaag atgactggaa agtctattca gccagaaaat     420
cttgagtata gaattatgct ttctgttcac ggatctcaac attctggaat gattgttaac     480
gatactggac acgaaactga cgagaataga gctaaggttg aaattactcc aaattctcca     540
agagctgaag ctactcttgg aggatttgga tctcttggac ttgattgtga gccaagaact     600
ggacttgatt tttctgatct ttattatctt actatgaaca caaacattg gcttgttcat      660
aaggaatggt tcatgatat tccacttcct tggcatgctg agctgatac tggaactcca      720
cattggaaca caaggaagc tcttgttgag ttcaaggatg ctcatgctaa gacaaact      780
gttgttgttc ttggatctca agaaggagct gttcatactg ctcttgctgg tgctcttgaa     840
gctgagatgg atggagctaa gggaaggctt tcttctggac accttaagtg cagacttaag     900
atggacaaac ttagacttaa gggagtttct tactctcttt gcactgctgc tttcactttt     960
actaagattc cagctgaaac tcttcatgga actgtgactg tggaagttca atatgctgga    1020
actgatggac catgtaaggt tccagctcaa atggctgtgg atatgcagac tcttactcca    1080
gttgaaggc ttattactgc taacccagtt attactgagt ctactgaaaa ctctaagatg    1140
atgcttgagc ttgatccacc attcggagat tcttacattg ttattggagt tggagaaaag    1200
aagattactc atcattggca taggtctgga tctactattg gaaaggcttt tgaagctact    1260
gttagaggag ctaagagaat ggctgttctt ggagatactg cttgggattt tggatctcat    1320
catcatcatc atcat                                                     1335
```

<210> SEQ ID NO 17
<211> LENGTH: 445
<212> TYPE: PRT
<213> ORGANISM: Artificial sequence
<220> FEATURE:
<223> OTHER INFORMATION: synthetic

<400> SEQUENCE: 17

```
His His His His His His Ile Arg Cys Ile Gly Val Ser Asn Arg Asp
 1               5                  10                  15

Phe Val Glu Gly Met Ser Gly Gly Thr Trp Val Asp Val Val Leu Glu
            20                  25                  30

His Gly Gly Cys Val Thr Val Met Ala Gln Asp Lys Pro Thr Val Asp
        35                  40                  45

Ile Glu Leu Val Thr Thr Thr Val Ser Asn Met Ala Glu Val Arg Ser
    50                  55                  60
```

Tyr Cys Tyr Glu Ala Ser Ile Ser Asp Met Ala Ser Asp Ser Arg Cys
 65                  70                  75                  80

Pro Thr Gln Gly Glu Ala Tyr Leu Asp Lys Gln Ser Asp Thr Gln Tyr
             85                  90                  95

Val Cys Lys Arg Thr Leu Val Asp Arg Gly Trp Gly Asn Gly Cys Gly
                100                 105                 110

Leu Phe Gly Lys Gly Ser Leu Val Thr Cys Ala Lys Phe Ala Cys Ser
        115                 120                 125

Lys Lys Met Thr Gly Lys Ser Ile Gln Pro Glu Asn Leu Glu Tyr Arg
130                 135                 140

Ile Met Leu Ser Val His Gly Ser Gln His Ser Gly Met Ile Val Asn
145                 150                 155                 160

Asp Thr Gly His Glu Thr Asp Glu Asn Arg Ala Lys Val Glu Ile Thr
                165                 170                 175

Pro Asn Ser Pro Arg Ala Glu Ala Thr Leu Gly Gly Phe Gly Ser Leu
            180                 185                 190

Gly Leu Asp Cys Glu Pro Arg Thr Gly Leu Asp Phe Ser Asp Leu Tyr
        195                 200                 205

Tyr Leu Thr Met Asn Asn Lys His Trp Leu Val His Lys Glu Trp Phe
    210                 215                 220

His Asp Ile Pro Leu Pro Trp His Ala Gly Ala Asp Thr Gly Thr Pro
225                 230                 235                 240

His Trp Asn Asn Lys Glu Ala Leu Val Glu Phe Lys Asp Ala His Ala
                245                 250                 255

Lys Arg Gln Thr Val Val Val Leu Gly Ser Gln Glu Gly Ala Val His
            260                 265                 270

Thr Ala Leu Ala Gly Ala Leu Glu Ala Glu Met Asp Gly Ala Lys Gly
        275                 280                 285

Arg Leu Ser Ser Gly His Leu Lys Cys Arg Leu Lys Met Asp Lys Leu
    290                 295                 300

Arg Leu Lys Gly Val Ser Tyr Ser Leu Cys Thr Ala Ala Phe Thr Phe
305                 310                 315                 320

Thr Lys Ile Pro Ala Glu Thr Leu His Gly Thr Val Thr Val Glu Val
                325                 330                 335

Gln Tyr Ala Gly Thr Asp Gly Pro Cys Lys Val Pro Ala Gln Met Ala
            340                 345                 350

Val Asp Met Gln Thr Leu Thr Pro Val Gly Arg Leu Ile Thr Ala Asn
        355                 360                 365

Pro Val Ile Thr Glu Ser Thr Glu Asn Ser Lys Met Met Leu Glu Leu
    370                 375                 380

Asp Pro Pro Phe Gly Asp Ser Tyr Ile Val Ile Gly Val Gly Glu Lys
385                 390                 395                 400

Lys Ile Thr His His Trp His Arg Ser Gly Ser Thr Ile Gly Lys Ala
                405                 410                 415

Phe Glu Ala Thr Val Arg Gly Ala Lys Arg Met Ala Val Leu Gly Asp
            420                 425                 430

Thr Ala Trp Asp Phe Gly Ser His His His His His
        435                 440                 445

VACCINES AGAINST ZIKA VIRUS BASED ON ZIKA STRUCTURE PROTEINS

CROSS-REFERENCE TO RELATED APPLICATIONS

This application is based on, claims a priority benefit from, and incorporates herein by reference, U.S. Provisional Patent Application No. 62/510,396, filed May 24, 2017, and entitled "Vaccines against Zika Virus Based on Zika Structure Proteins."

TECHNOLOGY FIELD

This disclosure relates to vaccine compositions and methods for protecting against ZIKA virus infection.

BACKGROUND

Zika virus (ZIKV) infection in humans used to be described as a self-limiting febrile illness with rash, headache, and myalgia. However, recent ZIKV outbreaks have linked ZIKV to the development of severe fetal abnormalities that include microcephaly and Guillain-Barre' syndrome in adults. Over 1.5 million people were infected with ZIKV in Brazil in 2015 alone and tens of millions more could be infected in American countries in the coming years. Currently, there are no licensed vaccines or therapeutics available to combat this virus. Therefore, there is an urgent call to develop effective and safe vaccines to prevent ZIKV infection.

ZIKV belongs to the genus Flavivirus in the family Flaviviridae, and is closely related to the four serotypes of dengue virus (DENV), West Nile virus (WNV), tick-borne encephalitis virus (TBEV), and yellow fever virus (YFV). Similar to other flaviviruses, the ZIKV Envelope (E) protein is composed of three ectodomains (EDI, EDII, and EDIII) and is responsible to mediate viral assembly, attachment to cellular receptors, and the subsequent membrane fusion involved in viral entry.

SUMMARY

Embodiments of the current disclosure provide a vaccine comprising virus like particles (VLPs) that includes at least a portion of ZIKA virus envelope protein domain III (zDIII) polypeptide, wherein upon administration of said vaccine to a mammal a cytotoxic immune reaction against ZIKV is induced. In other embodiments, the present disclosure relates to a vaccine comprising virus like particles (VLPs) that includes at least a portion of ZIKA virus envelope (E) protein. In yet other embodiments, the present disclosure relates to a vaccine to immunize a subject against ZIKA virus, wherein the vaccine comprises at least a portion of ZIKA virus envelope (E) protein. Furthermore, the portion of ZIKA virus E protein may either be a full-length version of ZIKA virus E protein comprising SEQ ID NO: 13 or a functionally equivalent version of the full-length Zika virus E protein. In addition, the portion of ZIKA virus E protein may be a full-length version of ZIKA virus E protein with its fusion loop (FL) epitope mutated by amino acid substitutions (zE-FL-mutant) or a functionally equivalent version of the full-length zE-FL-mutant. The zE-FL-mutant may comprise a sequence of SEQ ID NO: 14.

In certain embodiments, a method for eliciting an immunological response in a subject against ZIKA virus infection, the method comprising administering to the subject a therapeutically effective amount of a vaccine composition comprising VLPs that includes at least a portion of ZIKA virus envelope protein domain III (zDIII) polypeptide, wherein the VLPs are derived from Hepatitis B virus core antigen (HBcAg) is presented. In some embodiments, the portion of zDIII polypeptide comprises a sequence selected from the group consisting of SEQ ID NO: 1, SEQ ID NO: 7, SEQ ID NO: 8, SEQ ID NO: 9, SEQ ID NO: 10, SEQ ID NO: 11, and SEQ ID NO: 12. In other embodiments, the portion of zDIII polypeptide comprises a sequence of SEQ ID NO: 1. In addition, in certain embodiments, the present disclosure relates to a method for eliciting an immunological response in a subject against ZIKA virus infection, the method comprising administering to the subject a therapeutically effective amount of a vaccine comprising virus like particles (VLPs) that includes at least a portion of ZIKA virus envelope (E) protein. In another embodiment, the method comprises administering to the subject a therapeutically effective amount of a vaccine comprising at least a portion of ZIKA virus envelope (E) protein.

Further, embodiments of the current disclosure provide a method for protecting a subject against ZIKA virus infection, the method comprising administering to the subject a therapeutically effective amount of a vaccine composition comprising VLPs that comprises at least of portion of ZIKA virus envelope protein domain III (zDIII) polypeptide, wherein the VLPs are derived from Hepatitis B virus core antigen (HBcAg). In some embodiments, the portion of zDIII polypeptide comprises a sequence selected from the group consisting of SEQ ID NO: 1, SEQ ID NO: 7, SEQ ID NO: 8, SEQ ID NO: 9, SEQ ID NO: 10, SEQ ID NO: 11, and SEQ ID NO: 12. In other embodiments, the portion of zDIII polypeptide comprises a sequence of SEQ ID NO: 1. Moreover, in certain embodiments, the present disclosure relates to a method for protecting a subject against ZIKA virus infection, the method comprising administering to the subject a therapeutically effective amount of a vaccine comprising virus like particles (VLPs) that includes at least a portion of ZIKA virus envelope (E) protein. In another embodiment, the method comprises administering to the subject a therapeutically effective amount of a vaccine comprising at least a portion of ZIKA virus envelope (E) protein.

Additionally, in certain embodiments, a method for producing a vaccine composition is provided. The method comprises transforming a plasmid vector into an *agrobacterium* strain, wherein the plasmid vector comprises a backbone of tobacco mosaic virus (TMV) based pIC11599, a first polynucleotide encoding a portion of ZIKA virus envelope protein domain III (zDIII) polypeptide; and a second polynucleotide encoding HBcAg defined by SEQ ID NO: 2 and operatively linked to the first polypeptide; overexpressing the *agrobacterium* strain comprising the plasmid vector in a plant; and extracting and purifying the vaccine composition from the plant. In some embodiments, the portion of zDIII polypeptide comprises a sequence selected from the group consisting of SEQ ID NO: 1, SEQ ID NO: 7, SEQ ID NO: 8, SEQ ID NO: 9, SEQ ID NO: 10, SEQ ID NO: 11, and SEQ ID NO: 12. In other embodiments, the portion of zDIII polypeptide comprises a sequence of SEQ ID NO: 1.

In other embodiments, the method for producing a vaccine composition comprises transforming a plasmid vector into an *agrobacterium* strain, wherein the plasmid vector comprises a backbone of tobacco mosaic virus (TMV) based pIC11599, a first polynucleotide encoding at least a portion of ZIKA virus envelope (E) protein, and a second polynucleotide encoding HBcAg defined by SEQ ID NO: 2 and operatively linked to the first polypeptide; overexpressing the *agrobacterium* strain comprising the plasmid vector in a plant; and extracting and purifying the vaccine composition from the plant. In yet other embodiments, the method for producing a vaccine composition comprises transforming a plasmid vector into an *agrobacterium* strain, wherein the plasmid vector comprises a backbone of tobacco mosaic virus (TMV) based pIC11599 and a polynucleotide encoding at least a portion of ZIKA virus envelope (E) protein; overexpressing the *agrobacterium* strain comprising the plasmid vector in a plant; and extracting and purifying the vaccine composition from the plant.

BRIEF DESCRIPTION OF DRAWINGS

The technology disclosed herein will be better understood from a reading of the following detailed description taken in conjunction with the drawings in which like reference designators are used to designate like elements, and in which:

Figure 11:
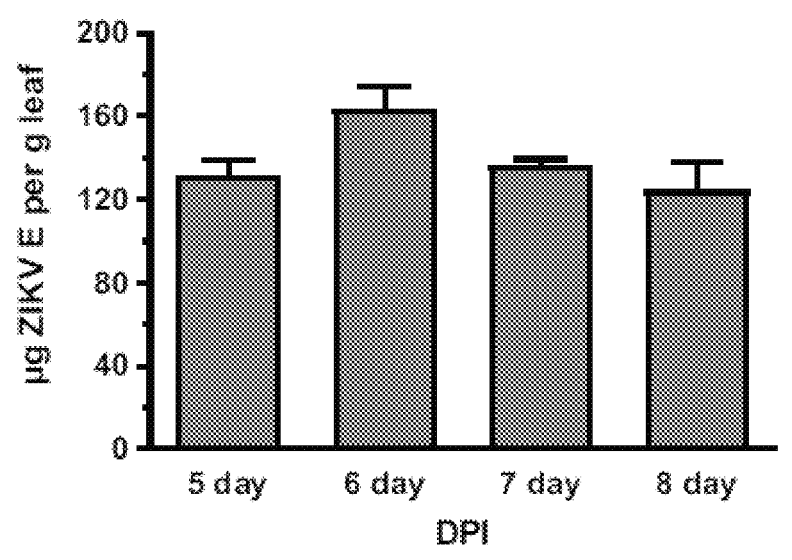

FIG. 11. Time course of PzE accumulation in *Nicotiana benthamiana* leaves. Soluble proteins were extracted from zE construct-agroinfiltrated leaves from 5 to 8 days postinfiltration (DPI). An ELISA was used to examine the levels of PzE in plant extracts. Mean±standard deviation (SD) of protein extracts from three independent infiltration experiments is presented.

DETAILED DESCRIPTION

Figure 1:
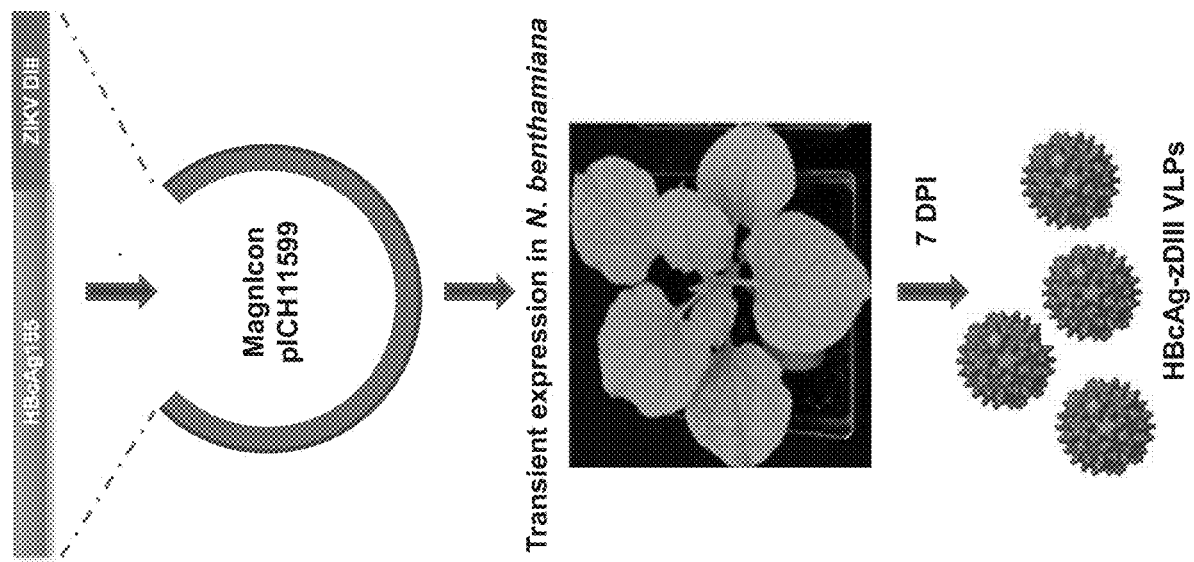
FIG. 1. Expression of HBcAg-zDIII in *N. benthamiana* plants. The coding sequence of zDIII was fused to the 3' of the coding sequence of HBcAg (amino acid 1 to 155) and cloned into the MagnICON-based plant expression vector pICH11599. The *A. tumefaciens* strain that contains pICH11599-HBcAg-zDIII construct were agroinfiltrated into *N. benthamiana* leaves for transient expression. Leaves were harvested at 7 days post agroinfiltration (DPI) for HBcAg-zDIII isolation.

The technology disclosed herein is described in one or more exemplary embodiments in the following description with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present technology disclosed herein. Thus, appearances of the phrases "in one embodiment," "in an embodiment," and similar language throughout this specification may, but do not necessarily, all refer to the same embodiment.

The described features, structures, or characteristics of the technology disclosed herein may be combined in any suitable manner in one or more embodiments. In the following description, numerous specific details are recited to provide a thorough understanding of embodiments of the technology disclosed herein. One skilled in the relevant art will recognize, however, that the technology disclosed herein may be practiced without one or more of the specific details, or with other methods, components, materials, and so forth. In other instances, well-known structures, materials, or operations are not shown or described in detail to avoid obscuring aspects of the technology disclosed herein.

ZIKV E (zE) is a major target of host antibody responses and its EDIII (zDIII) has been found to be targeted by several ZIKV-specific antibodies with strong neutralizing activities. Also, epitopes of potent neutralizing anti-bodies have been mapped to all three zE domains. Since neutralizing antibodies have been shown to be correlated with protection for approved vaccines against YFV and TBEV, and having been demonstrated to play important roles in the protection against infection by many flaviviruses including ZIKV, zDIII is considered a prime candidate of an effective subunit vaccine against ZIKV due to its potential in inducing potent neutralizing antibodies.

The high degree of genetic similarity between ZIKV and DENV poses challenges for vaccine development due to the phenomenon of antibody-dependent enhancement of infection (ADE), which has been implicated for DENV infection. While antibodies generated during a primary infection of DENV can protect the host against the homologous serotype, these antibodies may be non-neutralizing or sub-neutralizing against a heterologous DENV serotype in a secondary infection. Instead, these cross-reactive antibodies can enhance infection of the second DENV serotype in Fc gamma receptor (FcγR)-expressing cells and lead to a potentially lethal shock syndrome through ADE. Since ZIKV and DENV are closely related and co-circulate geographically, ZIKV vaccines that are based on common epitopes of the two viruses may elicit cross-reactive antibodies that augment infection of DENV in vaccinated subjects when they are exposed to DENV secondarily. This hypothesis is supported by the finding that cross-reactive antibodies targeting the highly conserved fusion loop in EDII (EDII-FL) of zE generated during natural ZIKV infection can enhanced DENV infection both in cell culture and in mice. Therefore, vaccine strategies based on antigens that can avoid induction of cross-reactive antibodies should minimize the risk of ADE of DENV infections.

Vaccine candidates based on inactivated virus, and a lipid-nanoparticle-encapsulated nucleoside-modified mRNA (mRNA-LNP), and naked or adenovirus-vectored DNA that expresses ZIKV premembrane (prM) and E protein (prM-E) were recently evaluated and shown to induce neutralizing antibodies that provide protection against ZIKV challenges in both mouse and rhesus monkey models. While these developments are encouraging, hurdles remain to be overcome on the path to further develop these ZIKV vaccine candidates, particularly in regards to safety and cost-effectiveness.

In certain embodiments, a zDIII-based subunit vaccine in the form of zDIII-displaying virus-like particles (VLPs) based on the hepatitis B core antigen (HBcAg) is generated. Unlike DNA-based vaccines, there is no risk of genome insertion or associated oncogenesis by protein-based vaccines. Furthermore, zDIII VLPs are also safer than inactivated virus and viral vector-based vaccines due to the virtual nonexistence of possible incomplete inactivation or unfavorable host responses to viral vectors. The use of zDIII, an antigen containing well-defined neutralizing epitopes but avoiding epitopes with ADE pathological effects, is aimed to further enhance the safety of ZIKV vaccines while maintaining the potency.

In certain embodiments, the use of a VLP carrier to display zDIII and plants as a production platform is explored to increase the immunogenicity, stability, and cost effectiveness of this vaccine candidate. In other embodiments, other production platforms for VLP carrier displaying zDIII can be used, such as, yeast, E. coli, insect cells, or mammalian cells.

Further, in certain embodiments, a zE-based subunit vaccine produced via transient expression in Nicotiana benthamianan plants is generated. In certain embodiments, a zE-based subunit vaccine in the form of zE with its fusion loop epitope (FL) in domain II (zDII) mutated (zE-FL-mutant) is generated. Additionally, in certain embodiments, a zE or zE-FL-mutant-based subunit vaccine in the form of zE/zE-FL-mutant-displaying virus-like particles (VLPs) based on the hepatitis B core antigen (HBcAg) is generated. The plant-derived zE-based subunit vaccine is equal or more potent at inducing strong neutralizing antibody and cellular immune responses. Also, as plant expression systems have shown promise in significantly reducing the cost of biologic production, the plant production of PzE also addresses the affordability of ZIKV vaccines for the developing world, where the majority of ZIKV cases exists.

Vaccines of the Present Disclosure

This disclosure provides vaccine compositions and methods that relate to the use of peptide vaccines for the protecting against ZIKA virus infection. Specifically, embodiments of the vaccine compositions comprise VLPs displaying a portion of zDIII polypeptide. In other embodiments, the vaccine compositions comprise VLPs displaying at least a portion of ZIKA virus envelope (E) protein. In yet other embodiments, the vaccine compositions comprise at least a portion of ZIKA virus envelope (E) protein.

As used herein, the term "vaccine" refers to a composition that serves to stimulate an immune response to ZIKA virus infection. As used herein, the terms "therapeutic amount," "effective amount," and "antigenically effective amount" refer to an amount of antigen or vaccine effective to elicit an immune response against an ZIKA virus antigen present in the composition, thereby preventing ZIKA virus infection upon administration of the composition to a subject in need thereof. The term "ZIKA virus" includes all ZIKA virus strains that invade, colonize, and induce disease in bodily sites.

As used herein, the term "a fragment/portion of zDIII/zE" polypeptide refers to the full-length polypeptide sequence, fragments of the reference sequence, or substitutions, deletions and/or additions to the reference sequences (SEQ ID NO: 1, SEQ ID NO: 13, and SEQ ID NO: 14), so long as the proteins or fragments thereof retain at least zDIII/zE epitope or activity. The term "protect" used herein refer to either (i) the prevention of infection or re-infection, or (ii) the reduction or elimination of symptoms of the disease of interest.

In one embodiment, the vaccine comprises a portion of the zDIII polypeptide, which is the coding sequence of zDIII of ZIKA virus strain PRVABC59 and this amino sequence can be found at Genebank Acc. No. AMC13911.1 (amino acid sequence SEQ ID NO: 1). In some embodiments, the vaccine comprises a portion of the zDIII polypeptide that is a full-length version of SEQ ID NO: 1 (AFTFTKIPAE TLHGTVTVEV QYAGTDGPCK VPAQMAVDMQ TLTPVGRLIT ANPVITESTENSKMMLELDP PFGDSYIVIG VGEKKITHHW HRS) or a functionally equivalent version of the full-length version of SEQ ID NO: 1. As used herein, the term "functionally equivalent" refers to a zDIII polypeptide fragment that retains at least 90% activity of the sequence defined as SEQ ID NO: 1. In other embodiments, the vaccine comprises a zDIII polypeptide fragment that is part of a full-length version of SEQ ID NO: 1 and the zDIII polypeptide fragment retains at least 90% activity of the sequence defined as SEQ ID NO: 1.

It is readily recognizable that zDIII of other ZIKA virus strains, or any of the zDIII's derivatives, equivalents, variants, mutants etc., is suitable for the instant technology, as long as the zDIII or derivatives, equivalents, variants, or mutants thereof is able to induce an immune reaction in the host human or non-human animal substantially similar to that induced by the vaccine compositions comprising zDIII polypeptide defined by SEQ ID NO: 1. The zDIII and full E protein sequences are highly conserved among different Zika virus strains including those from Africa, Asia and South Americas. Among all the strains compared (GenBank Accession no. AY632535, KU321639, KJ776791, KF383115, KF383116, KF383117, KF383118, KF383119, KF268948, KF268949, KF268950, EU545988, KF993678, JN860885, HQ234499, KU501215, KU501216, KU501217), the zDIII sequence have at least about 96% identity (the 3-4 amino acid difference between the recent outbreak strains and the strains during the 1947-1984 outbreaks would not change the efficacy of our vaccine). The exemplary strains listed here are not meant to be limiting. The vaccine compositions comprising zDIII polypeptide defined by SEQ ID NO: 1 may be effective against other strains.

In certain embodiments, the vaccine comprises a portion of the zDIII polypeptide that comprises a sequence selected from the group consisting of SEQ ID NO: 7, SEQ ID NO: 8, SEQ ID NO: 9, SEQ ID NO: 10, SEQ ID NO: 11, and SEQ ID NO: 12 listed in Table 1.

TABLE 1 zDIII amino acid sequences from different strains.

| | (1) | 1 | | | | | | | | | 10 | | | | | |
|---|---|---|---|---|---|---|---|---|---|---|---|---|---|---|---|---|
| PRVABC59/Puerto Rico (SEQ ID NO: 1) | (1) | A | F | T | F | T | K | I | P | A | E | T | L | H | G | T | V |
| Brazil/2016/INMI1 | (1) | A | F | T | F | T | K | I | P | A | E | T | L | H | G | T | V |
| Central African Republic ARB13565 1976 (SEQ ID NO: 7) | (1) | A | F | T | F | T | K | V | P | A | E | T | L | H | G | T | V |
| Nigeria IbH_30656 1968 (SEQ ID NO: 8) | (1) | A | F | T | F | T | K | V | P | A | E | T | L | H | G | T | V |
| Senegal ArD_41519 1984 (SEQ ID NO: 7) | (1) | A | F | T | F | T | K | V | P | A | E | T | L | H | G | T | V |
| Zika virus/A.africanus-tc/SEN/1984/41525-DAK (SEQ ID NO: 7) | (1) | A | F | T | F | T | K | V | P | A | E | T | L | H | G | T | V |
| Zika virus/M.mulatta-tc/UGA/1947/MR-766 (SEQ ID NO: 9) | (1) | A | F | T | F | T | K | V | P | A | E | T | L | H | G | T | V |
| Malaysia P6-740 1966 (SEQ ID NO: 10) | (1) | A | F | T | F | T | K | I | P | A | E | T | L | H | G | T | V |
| CKS63-2014/Cook Islands | (1) | A | F | T | F | T | K | I | P | A | E | T | L | H | G | T | V |
| Dominican Republic/2016/PD2 | (1) | A | F | T | F | T | K | I | P | A | E | T | L | H | G | T | V |
| ESS23-2015/El Salvador | (1) | A | F | T | F | T | K | I | P | A | E | T | L | H | G | T | V |
| F8-GWUH-2016 (SEQ ID NO: 11) | (1) | A | F | T | F | T | K | I | P | A | E | T | L | H | G | T | V |
| French Polynesia H/PF/2013 2013 | (1) | A | F | T | F | T | K | I | P | A | E | T | L | H | G | T | V |
| FS92 2016/Fiji | (1) | A | F | T | F | T | K | I | P | A | E | T | L | H | G | T | V |
| Haiti/1225/2014 | (1) | A | F | T | F | T | K | I | P | A | E | T | L | H | G | T | V |
| MEX/lnDRE/Sm/2016 | (1) | A | F | T | F | T | K | I | P | A | E | T | L | H | G | T | V |
| PLCal_Zv/2013/Canada | (1) | A | F | T | F | T | K | I | P | A | E | T | L | H | G | T | V |
| VS51-2026/Viet Nam | (1) | A | F | T | F | T | K | I | P | A | E | T | L | H | G | T | V |
| Z110S033/Suriname/2015 | (1) | A | F | T | F | T | K | I | P | A | E | T | L | H | G | T | V |
| Zika virus/H.sapiens-tc/THA/2014/SV0127-14 (SEQ ID NO: 12) | (1) | A | F | T | F | T | K | I | P | A | E | T | L | H | G | T | V |
| Zika virus/SZ01/2016/China | (1) | A | F | T | F | T | K | I | P | A | E | T | L | H | G | T | V |
| ZIKV/Hu/Chiba/S36/2016/Japan | (1) | A | F | T | F | T | K | I | P | A | E | T | L | H | G | T | V |
| Consensus | (1) | A | F | T | F | T | K | I | P | A | E | T | L | H | G | T | V |

| | | | 20 | | | | | | | | 30 | | | | |
|---|---|---|---|---|---|---|---|---|---|---|---|---|---|---|---|
| PRVABC59/Puerto Rico (SEQ ID NO: 1) | T | V | E | V | Q | Y | A | G | T | D | G | P | C | K | V | P | A |
| Brazil/2016/INMI1 | T | V | E | V | Q | Y | A | G | T | D | G | P | C | K | V | P | A |
| Central African Republic ARB13565 1976 (SEQ ID NO: 7) | T | V | E | V | Q | Y | A | G | T | D | G | P | C | K | V | P | A |
| Nigeria IbH_30656 1968 (SEQ ID NO: 8) | T | V | E | V | Q | Y | A | G | R | D | G | P | C | K | V | P | A |
| Senegal ArD_41519 1984 (SEQ ID NO: 7) | T | V | E | V | Q | Y | A | G | T | D | G | P | C | K | V | P | A |
| Zika virus/A.africanus-tc/SEN/1984/41525-DAK (SEQ ID NO: 7) | T | V | E | V | Q | Y | A | G | T | D | G | P | C | K | V | P | A |
| Zika virus/M.mulatta-tc/UGA/1947/MR-766 (SEQ ID NO: 9) | T | V | E | V | Q | Y | A | G | T | D | G | P | C | K | I | P | V |
| Malaysia P6-740 1966 (SEQ ID NO: 10) | T | V | E | V | Q | Y | A | G | T | D | G | P | C | K | V | P | A |
| CKS63-2014/Cook Islands | T | V | E | V | Q | Y | A | G | T | D | G | P | C | K | V | P | A |
| Dominican Republic/2016/PD2 | T | V | E | V | Q | Y | A | G | T | D | G | P | C | K | V | P | A |
| ESS23-2015/El Salvador | T | V | E | V | Q | Y | A | G | T | D | G | P | C | K | V | P | A |
| F8-GWUH-2016 (SEQ ID NO: 11) | T | V | E | V | Q | Y | A | G | T | D | G | P | C | K | V | P | A |
| French Polynesia H/PF/2013 2013 | T | V | E | V | Q | Y | A | G | T | D | G | P | C | K | V | P | A |
| FS92 2016/Fiji | T | V | E | V | Q | Y | A | G | T | D | G | P | C | K | V | P | A |
| Haiti/1225/2014 | T | V | E | V | Q | Y | A | G | T | D | G | P | C | K | V | P | A |
| MEX/lnDRE/Sm/2016 | T | V | E | V | Q | Y | A | G | T | D | G | P | C | K | V | P | A |
| PLCal_Zv/2013/Canada | T | V | E | V | Q | Y | A | G | T | D | G | P | C | K | V | P | A |
| VS51-2026/Viet Nam | T | V | E | V | Q | Y | A | G | T | D | G | P | C | K | V | P | A |
| Z110S033/Suriname/2015 | T | V | E | V | Q | Y | A | G | T | D | G | P | C | K | V | P | A |
| Zika virus/H.sapiens-tc/THA/2014/SV0127-14 (SEQ ID NO: 12) | T | V | E | V | Q | Y | A | G | T | D | G | P | C | K | V | P | A |
| Zika virus/SZ01/2016/China | T | V | E | V | Q | Y | A | G | T | D | G | P | C | K | V | P | A |
| ZIKV/Hu/Chiba/S36/2016/Japan | T | V | E | V | Q | Y | A | G | T | D | G | P | C | K | V | P | A |
| Consensus | T | V | E | V | Q | Y | A | G | T | D | G | P | C | K | V | P | A |

TABLE 1 -continued zDIII amino acid sequences from different strains.

| | | | | | 40 | | | | | 46 | (47) | 47 | | | | |
|---|---|---|---|---|---|---|---|---|---|---|---|---|---|---|---|---|
| PRVABC59/Puerto Rico (SEQ ID NO: 1) | Q | M | A | V | D | M | Q | T | L | T | P | V | G | (47) | R | L |
| Brazil/2016/INMI1 | Q | M | A | V | D | M | Q | T | L | T | P | V | G | (47) | R | L |
| Central African Republic ARB13565 1976 (SEQ ID NO: 7) | Q | M | A | V | D | M | Q | T | L | T | P | V | G | (47) | R | L |
| Nigeria IbH_30656 1968 (SEQ ID NO: 8) | Q | M | A | V | D | M | Q | T | L | T | P | V | G | (47) | R | L |
| Senegal ArD_41519 1984 (SEQ ID NO: 7) | Q | M | A | V | D | M | Q | T | L | T | P | V | G | (47) | R | L |
| Zika virus/A.africanus-tc/SEN/1984/41525-DAK (SEQ ID NO: 7) | Q | M | A | V | D | M | Q | T | L | T | P | V | G | (47) | R | L |
| Zika virus/M.mulatta-tc/UGA/1947/MR-766 (SEQ ID NO: 9) | Q | M | A | V | D | M | Q | T | L | T | P | V | G | (47) | R | L |
| Malaysia P6-740 1966 (SEQ ID NO: 10) | Q | M | A | V | D | M | Q | T | L | T | P | V | G | (47) | R | L |
| CKS63-2014/Cook Islands | Q | M | A | V | D | M | Q | T | L | T | P | V | G | (47) | R | L |
| Dominican Republic/2016/PD2 | Q | M | A | V | D | M | Q | T | L | T | P | V | G | (47) | R | L |
| ESS23-2015/El Salvador | Q | M | A | V | D | M | Q | T | L | T | P | V | G | (47) | R | L |
| F8-GWUH-2016 (SEQ ID NO: 11) | Q | M | A | V | D | M | Q | T | L | T | P | V | G | (47) | R | L |
| French Polynesia H/PF/2013 2013 | Q | M | A | V | D | M | Q | T | L | T | P | V | G | (47) | R | L |
| FS92 2016/Fiji | Q | M | A | V | D | M | Q | T | L | T | P | V | G | (47) | R | L |
| Haiti/1225/2014 | Q | M | A | V | D | M | Q | T | L | T | P | V | G | (47) | R | L |
| MEX/lnDRE/Sm/2016 | Q | M | A | V | D | M | Q | T | L | T | P | V | G | (47) | R | L |
| PLCal_Zv/2013/Canada | Q | M | A | V | D | M | Q | T | L | T | P | V | G | (47) | R | L |
| VS51-2026/Viet Nam | Q | M | A | V | D | M | Q | T | L | T | P | V | G | (47) | R | L |
| Z110S033/Suriname/2015 | Q | M | A | V | D | M | Q | T | L | T | P | V | G | (47) | R | L |
| Zika virus/H.sapiens-tc/THA/2014/SV0127-14 (SEQ ID NO: 12) | Q | M | A | V | D | M | Q | T | L | T | P | V | G | (47) | R | L |
| Zika virus/SZ01/2016/China | Q | M | A | V | D | M | Q | T | L | T | P | V | G | (47) | R | L |
| ZIKV/Hu/Chiba/S36/2016/Japan | Q | M | A | V | D | M | Q | T | L | T | P | V | G | (47) | R | L |
| Consensus | Q | M | A | V | D | M | Q | T | L | T | P | V | G | (47) | R | L |

| | | 50 | | | | | | | | 60 | | | | | | |
|---|---|---|---|---|---|---|---|---|---|---|---|---|---|---|---|---|
| PRVABC59/Puerto Rico (SEQ ID NO: 1) | I | T | A | N | P | V | I | T | E | S | T | E | N | S | K | M |
| Brazil/2016/INMI1 | I | T | A | N | P | V | I | T | E | S | T | E | N | S | K | M |
| Central African Republic ARB13565 1976 (SEQ ID NO: 7) | I | T | A | N | P | V | I | T | E | S | T | E | N | S | K | M |
| Nigeria IbH_30656 1968 (SEQ ID NO: 8) | I | T | A | N | P | V | I | T | E | S | T | E | N | S | K | M |
| Senegal ArD_41519 1984 (SEQ ID NO: 7) | I | T | A | N | P | V | I | T | E | S | T | E | N | S | K | M |
| Zika virus/A.africanus-tc/SEN/1984/41525-DAK (SEQ ID NO: 7) | I | T | A | N | P | V | I | T | E | S | T | E | N | S | K | M |
| Zika virus/M.mulatta-tc/UGA/1947/MR-766 (SEQ ID NO: 9) | I | T | A | N | P | V | I | T | E | S | T | E | N | S | K | M |
| Malaysia P6-740 1966 (SEQ ID NO: 10) | I | T | A | N | P | V | I | T | E | S | T | E | N | S | K | M |
| CKS63-2014/Cook Islands | I | T | A | N | P | V | I | T | E | S | T | E | N | S | K | M |
| Dominican Republic/2016/PD2 | I | T | A | N | P | V | I | T | E | S | T | E | N | S | K | M |
| ESS23-2015/El Salvador | I | T | A | N | P | V | I | T | E | S | T | E | N | S | K | M |
| F8-GWUH-2016 (SEQ ID NO: 11) | I | T | A | N | P | V | I | T | E | S | T | E | N | S | K | M |
| French Polynesia H/PF/2013 2013 | I | T | A | N | P | V | I | T | E | S | T | E | N | S | K | M |
| FS92 2016/Fiji | I | T | A | N | P | V | I | T | E | S | T | E | N | S | K | M |
| Haiti/1225/2014 | I | T | A | N | P | V | I | T | E | S | T | E | N | S | K | M |
| MEX/lnDRE/Sm/2016 | I | T | A | N | P | V | I | T | E | S | T | E | N | S | K | M |
| PLCal_Zv/2013/Canada | I | T | A | N | P | V | I | T | E | S | T | E | N | S | K | M |
| VS51-2026/Viet Nam | I | T | A | N | P | V | I | T | E | S | T | E | N | S | K | M |
| Z110S033/Suriname/2015 | I | T | A | N | P | V | I | T | E | S | T | E | N | S | K | M |
| Zika virus/H.sapiens-tc/THA/2014/SV0127-14 (SEQ ID NO: 12) | I | T | A | N | P | V | I | T | E | G | T | E | N | S | K | M |
| Zika virus/SZ01/2016/China | I | T | A | N | P | V | I | T | E | S | T | E | N | S | K | M |
| ZIKV/Hu/Chiba/S36/2016/Japan | I | T | A | N | P | V | I | T | E | S | T | E | N | S | K | M |
| Consensus | I | T | A | N | P | V | I | T | E | S | T | E | N | S | K | M |

TABLE 1 -continued zDIII amino acid sequences from different strains.

| | | | | | 70 | | | | | | | | | 80 | |
|---|---|---|---|---|---|---|---|---|---|---|---|---|---|---|---|
| PRVABC59/Puerto Rico (SEQ ID NO: 1) | M | L | E | L | D | P | P | F | G | D | S | Y | I | V | I | G |
| Brazil/2016/INMI1 | M | L | E | L | D | P | P | F | G | D | S | Y | I | V | I | G |
| Central African Republic ARB13565 1976 (SEQ ID NO: 7) | M | L | E | L | D | P | P | F | G | D | S | Y | I | V | I | G |
| Nigeria IbH_30656 1968 (SEQ ID NO: 8) | M | L | E | L | D | P | P | F | G | D | S | Y | I | V | I | G |
| Senegal ArD_41519 1984 (SEQ ID NO: 7) | M | L | E | L | D | P | P | F | G | D | S | Y | I | V | I | G |
| Zika virus/A.africanus-tc/SEN/1984/41525-DAK (SEQ ID NO: 7) | M | L | E | L | D | P | P | F | G | D | S | Y | I | V | I | G |
| Zika virus/M.mulatta-tc/UGA/1947/MR-766 (SEQ ID NO: 9) | M | L | E | L | D | P | P | F | G | D | S | Y | I | V | I | G |
| Malaysia P6-740 1966 (SEQ ID NO: 10) | M | L | E | L | D | P | P | F | G | D | S | Y | I | V | I | G |
| CKS63-2014/Cook Islands | M | L | E | L | D | P | P | F | G | D | S | Y | I | V | I | G |
| Dominican Republic/2016/PD2 | M | L | E | L | D | P | P | F | G | D | S | Y | I | V | I | G |
| ESS23-2015/El Salvador | M | L | E | L | D | P | P | F | G | D | S | Y | I | V | I | G |
| F8-GWUH-2016 (SEQ ID NO: 11) | M | L | E | L | D | P | P | F | G | D | S | Y | I | V | I | G |
| French Polynesia H/PF/2013 2013 | M | L | E | L | D | P | P | F | G | D | S | Y | I | V | I | G |
| FS92 2016/Fiji | M | L | E | L | D | P | P | F | G | D | S | Y | I | V | I | G |
| Haiti/1225/2014 | M | L | E | L | D | P | P | F | G | D | S | Y | I | V | I | G |
| MEX/lnDRE/Sm/2016 | M | L | E | L | D | P | P | F | G | D | S | Y | I | V | I | G |
| PLCal_Zv/2013/Canada | M | L | E | L | D | P | P | F | G | D | S | Y | I | V | I | G |
| VS51-2026/Viet Nam | M | L | E | L | D | P | P | F | G | D | S | Y | I | V | I | G |
| Z110S033/Suriname/2015 | M | L | E | L | D | P | P | F | G | D | S | Y | I | V | I | G |
| Zika virus/H.sapiens-tc/THA/2014/SV0127-14 (SEQ ID NO: 12) | M | L | E | L | D | P | P | F | G | D | S | Y | I | V | I | G |
| Zika virus/SZ01/2016/China | M | L | E | L | D | P | P | F | G | D | S | Y | I | V | I | G |
| ZIKV/Hu/Chiba/S36/2016/Japan | M | L | E | L | D | P | P | F | G | D | S | Y | I | V | I | G |
| Consensus | M | L | E | L | D | P | P | F | G | D | S | Y | I | V | I | G |

| | | | | | | | 90 | | 93 | | |
|---|---|---|---|---|---|---|---|---|---|---|---|
| PRVABC59/Puerto Rico (SEQ ID NO: 1) | V | G | E | K | K | I | T | H | H | W | H | R | S |
| Brazil/2016/INMI1 | V | G | E | K | K | I | T | H | H | W | H | R | S |
| Central African Republic ARB13565 1976 (SEQ ID NO: 7) | V | G | D | K | K | I | T | H | H | W | H | R | S |
| Nigeria IbH_30656 1968 (SEQ ID NO: 8) | V | G | D | K | K | I | T | H | H | W | H | R | S |
| Senegal ArD_41519 1984 (SEQ ID NO: 7) | V | G | D | K | K | I | T | H | H | W | H | R | S |
| Zika virus/A.africanus-tc/SEN/1984/41525-DAK (SEQ ID NO: 7) | V | G | D | K | K | I | T | H | H | W | H | R | S |
| Zika virus/M.mulatta-tc/UGA/1947/MR-766 (SEQ ID NO: 9) | V | G | D | K | K | I | T | H | H | W | H | R | S |
| Malaysia P6-740 1966 (SEQ ID NO: 10) | V | G | D | K | K | I | T | H | H | W | X | R | S |
| CKS63-2014/Cook Islands | V | G | E | K | K | I | T | H | H | W | H | R | S |
| Dominican Republic/2016/PD2 | V | G | E | K | K | I | T | H | H | W | H | R | S |
| ESS23-2015/El Salvador | V | G | E | K | K | I | T | H | H | W | H | R | S |
| F8-GWUH-2016 (SEQ ID NO: 11) | I | G | E | K | K | I | T | H | H | W | H | R | S |
| French Polynesia H/PF/2013 2013 | V | G | E | K | K | I | T | H | H | W | H | R | S |
| FS92 2016/Fiji | V | G | E | K | K | I | T | H | H | W | H | R | S |
| Haiti/1225/2014 | V | G | E | K | K | I | T | H | H | W | H | R | S |
| MEX/lnDRE/Sm/2016 | V | G | E | K | K | I | T | H | H | W | H | R | S |
| PLCal_Zv/2013/Canada | V | G | E | K | K | I | T | H | H | W | H | R | S |
| VS51-2026/Viet Nam | V | G | E | K | K | I | T | H | H | W | H | R | S |
| Z110S033/Suriname/2015 | V | G | E | K | K | I | T | H | H | W | H | R | S |
| Zika virus/H.sapiens-tc/THA/2014/SV0127-14 (SEQ ID NO: 12) | V | G | E | K | K | I | T | H | H | W | H | R | S |
| Zika virus/SZ01/2016/China | V | G | E | K | K | I | T | H | H | W | H | R | S |
| ZIKV/Hu/Chiba/S36/2016/Japan | V | G | E | K | K | I | T | H | H | W | H | R | S |
| Consensus | V | G | E | K | K | I | T | H | H | W | H | R | S |

TABLE 2

Full E protein amino acid sequences from different strains.

| | | (1) | 1          10          29 |
|---|---|---|---|
| PRVABC59/Puerto Rico | | (1) | IRCIGVSNRDFVEGMSGGTWVDVVLEHGG |
| Brazil/2016/INMI1 | | (1) | IRCIGVSNRDFVEGMSGGTWVDVVLEHGG |
| Central African Republic ARB13565 1976 | | (1) | IRCIGVSNRDFVEGMSGGTWVDVVLEHGG |
| Nigeria IbH_30656 1968 | | (1) | IRCIGVSNRDFVEGMSGGTWVDVVLEHGG |
| Senegal ArD_41519 1984 | | (1) | IRCIGVSNRDFVEGMSGGTWVDVVLEHGG |
| Zika virus/A. africanus-tc/SEN/1984/41525-DAK | | (1) | IRCIGVSNRDFVEGMSGGTWVDVVLEHGG |
| Zika virus/M. mulatta-tc/UGA/1947/MR-766 | | (1) | IRCIGVSNRDFVEGMSGGTWVDVVLEHGG |
| Malaysia P6-740 1966 | | (1) | IRCIGVSNRDFVEGMSGGTWVDVVLEHGG |
| CKS63-2014/Cook Islands | | (1) | IRCIGVSNRDFVEGMSGGTWVDVVLEHGG |
| Dominican Republic/2016/PD2 | | (1) | IRCIGVSNRDFVEGMSGGTWVDVVLEHGG |
| ESS23-2015/El Salvador | | (1) | IRCIGVSNRDFVEGMSGGTWVDVVLEHGG |
| FB-GWUH-2016 | | (1) | IRCIGVSNRDFVEGMSGGTWVDVVLEHGG |
| French Polynesia H/PF/2013 2013 | | (1) | IRCIGVSNRDFVEGMSGGTWVDVVLEHGG |
| FS92-2016/Fiji | | (1) | IRCIGVSNRDFVEGMSGGTWVDVVLEHGG |
| Haiti/1225/2014 | | (1) | IRCIGVSNRDFVEGMSGGTWVDVVLEHGG |
| MEX/InDRE/Sm/2016 | | (1) | IRCIGVSNRDFVEGMSGGTWVDVVLEHGG |
| PLCal_Zv/2013/Canada | | (1) | IRCIGVSNRDFVEGMSGGTWVDVVLEHGG |
| VS51-2016/Viet Nam | | (1) | IRCIGVSNRDFVEGMSGGTWVDVVLEHGG |
| Z1106033/Suriname/2015 | | (1) | IRCIGVSNRDFVEGMSGGTWVDVVLEHGG |
| Zika virus/H. sapiens-tc/THA/2014/SV0127-14 | | (1) | IRCIGVSNRDFVEGMSGGTWVDVVLEHGG |
| Zika virus/SZ01/2016/China | | (1) | IRCIGVSNRDFVEGMSGGTWVDVVLEHGG |
| ZIKV/Hu/Chiba/S36/2016/Japan | | (1) | IRCIGVSNRDFVEGMSGGTWVDVVLEHGG |
| Consensus | | (1) | IRCIGVSNRDFVEGMSGGTWVDVVLEHGG |
| | | (30) | 30          40          58 |
| PRVABC59/Puerto Rico | | (30) | CVTWMAQDKPTVDIELVTTTVSNMAEVRS |
| Brazil/2016/INMI1 | | (30) | CVTWMAQDKPTVDIELVTTTVSNMAEVRS |
| Central African Republic ARB13565 1976 | | (30) | CVTWMAQDKPTVDIELVTTTVSNMAEVRS |
| Nigeria IbH_30656 1968 | | (30) | CVTWMAQDKPTVDIELVTTTVSNMAEVRS |
| Senegal ArD_41519 1984 | | (30) | CVTWMAQDKPTVDIELVTTTVSNMAEVRS |
| Zika virus/A. africanus-tc/SEN/1984/41525-DAK | | (30) | CVTWMAQDKPTVDIELVTTTVSNMAEVRS |
| Zika virus/M. mulatta-tc/UGA/1947/MR-766 | | (30) | CVTWMAQDKPTVDIELVTTTVSNMAEVRS |
| Malaysia P6-740 1966 | | (30) | CVTWMAQDKPTVDIELVTTTVSNMAEVRS |
| CKS63-2014/Cook Islands | | (30) | CVTWMAQDKPTVDIELVTTTVSNMAEVRS |
| Dominican Republic/2016/PD2 | | (30) | CVTWMAQDKPTVDIELVTTTVSNMAEVRS |
| ESS23-2015/El Salvador | | (30) | CVTWMAQDKPTVDIELVTTTVSNMAEVRS |
| FB-GWUH-2016 | | (30) | CVTWMAQDKPTVDIELVTTTVSNMAEVRS |
| French Polynesia H/PF/2013 2013 | | (30) | CVTWMAQDKPTVDIELVTTTVSNMAEVRS |
| FS92-2016/Fiji | | (30) | CVTWMAQDKPTVDIELVTTTVSNMAEVRS |
| Haiti/1225/2014 | | (30) | CVTWMAQDKPTVDIELVTTTVSNMAEVRS |
| MEX/InDRE/Sm/2016 | | (30) | CVTWMAQDKPTVDIELVTTTVSNMAEVRS |
| PLCal_Zv/2013/Canada | | (30) | CVTWMAQDKPTVDIELVTTTVSNMAEVRS |
| VS51-2016/Viet Nam | | (30) | CVTWMAQDKPTVDIELVTTTVSNMAEVRS |
| Z1106033/Suriname/2015 | (30) | (30) | CVTWMAQDKPTVDIELVTTTVSNMAEVRS |
| Zika virus/H. sapiens-tc/THA/2014/SV0127-14 | | (30) | CVTWMAQDKPTVDIELVTTTVSNMAEVRS |
| Zika virus/SZ01/2016/China | | (30) | CVTWMAQDKPTVDIELVTTTVSNMAEVRS |
| ZIKV/Hu/Chiba/S36/2016/Japan | | (30) | CVTWMAQDKPTVDIELVTTTVSNMAEVRS |
| Consensus | | (30) | CVTWMAQDKPTVDIELVTTTVSNMAEVRS |

TABLE 2 -continued

Full E protein amino acid sequences from different strains.

| | | 59　　　　　　70　　　　　　87 |
|---|---|---|
| | (59) | |
| PRVABC59/Puerto Rico | (59) | YCYEASISDMASDSRCPTQGEAYLDKQSD |
| Brazil/2016/INMI1 | (59) | YCYEASISDMASDSRCPTQGEAYLDKQSD |
| Central African Republic ARB13565 1976 | (59) | YCYEASISDMASDSRCPTQGEAYLDKQSD |
| Nigeria IbH_30656 1968 | (59) | YCYEASISDMASDSRCPTQGEAYLDKQSD |
| Senegal ArD_41519 1984 | (59) | YCYEASISDMASDSRCPTQGEAYLDKQSD |
| Zika virus/A. africanus-tc/SEN/1984/41525-DAK | (59) | YCYEASISDMASDSRCPTQGEAYLDKQSD |
| Zika virus/M. mulatta-tc/UGA/1947/MR-766 | (59) | YCYEASISDMASDSRCPTQGEAYLDKQSD |
| Malaysia P6-740 1966 | (59) | YCYEASISDMASDSRCPTQGEAYLDKQSD |
| CKS63-2014/Cook Islands | (59) | YCYEASISDMASDSRCPTQGEAYLDKQSD |
| Dominican Republic/2016/PD2 | (59) | YCYEASISDMASDSRCPTQGEAYLDKQSD |
| ESS23-2015/El Salvador | (59) | YCYEASISDMASDSRCPTQGEAYLDKQSD |
| FB-GWUH-2016 | (59) | YCYEASISDMASDSRCPTQGEAYLDKQSD |
| French Polynesia H/PF/2013 2013 | (59) | YCYEASISDMASDSRCPTQGEAYLDKQSD |
| FS92-2016/Fiji | (59) | YCYEASISDMASDSRCPTQGEAYLDKQSD |
| Haiti/1225/2014 | (59) | YCYEASISDMASDSRCPTQGEAYLDKQSD |
| MEX/InDRE/Sm/2016 | (59) | YCYEASISDMASDSRCPTQGEAYLDKQSD |
| PLCal_Zv/2013/Canada | (59) | YCYEASISDMASDSRCPTQGEAYLDKQSD |
| VS51-2016/Viet Nam | (59) | YCYEASISDMASDSRCPTQGEAYLDKQSD |
| Z1106033/Suriname/2015 | (59) | YCYEASISDMASDSRCPTQGEAYLDKQSD |
| Zika virus/H. sapiens-tc/THA/2014/SV0127-14 | (59) | YCYEASISDMASDSRCPTQGEAYLDKQSD |
| Zika virus/SZ01/2016/China | (59) | YCYEASISDMASDSRCPTQGEAYLDKQSD |
| ZIKV/Hu/Chiba/S36/2016/Japan | (59) | YCYEASISDMASDSRCPTQGEAYLDKQSD |
| Consensus | (59) | YCYEASISDMASDSRCPTQGEAYLDKQSD |
| | | 88　　　　　100　　　　　116 |
| | (88) | |
| PRVABC59/Puerto Rico | (88) | TQYVCKRTLVDRGWGNGCGLFGKGSLVTC |
| Brazil/2016/INMI1 | (88) | TQYVCKRTLVDRGWGNGCGLFGKGSLVTC |
| Central African Republic ARB13565 1976 | (88) | TQYVCKRTLVDRGWGNGCGLFGKGSLVTC |
| Nigeria IbH_30656 1968 | (88) | TQYVCKRTLVDRGWGNGCGLFGKGSLVTC |
| Senegal ArD_41519 1984 | (88) | TQYVCKRTLVDRGWGNGCGLFGKGSLVTC |
| Zika virus/A. africanus-tc/SEN/1984/41525-DAK | (88) | TQYVCKRTLVDRGWGNGCGLFGKGSLVTC |
| Zika virus/M. mulatta-tc/UGA/1947/MR-766 | (88) | TQYVCKRTLVDRGWGNGCGLFGKGSLVTC |
| Malaysia P6-740 1966 | (88) | TQYVCKRTLVDRGWGNGCGLFGKGSLVTC |
| CKS63-2014/Cook Islands | (88) | TQYVCKRTLVDRGWGNGCGLFGKGSLVTC |
| Dominican Republic/2016/PD2 | (88) | TQYVCKRTLVDRGWGNGCGLFGKGSLVTC |
| ESS23-2015/El Salvador | (88) | TQYVCKRTLVDRGWGNGCGLFGKGSLVTC |
| FB-GWUH-2016 | (88) | TQYVCKRTLVDRGWGNGCGLFGKGSLVTC |
| French Polynesia H/PF/2013 2013 | (88) | TQYVCKRTLVDRGWGNGCGLFGKGSLVTC |
| FS92-2016/Fiji | (88) | TQYVCKRTLVDRGWGNGCGLFGKGSLVTC |
| Haiti/1225/2014 | (88) | TQYVCKRTLVDRGWGNGCGLFGKGSLVTC |
| MEX/InDRE/Sm/2016 | (88) | TQYVCKRTLVDRGWGNGCGLFGKGSLVTC |
| PLCal_Zv/2013/Canada | (88) | TQYVCKRTLVDRGWGNGCGLFGKGSLVTC |
| VS51-2016/Viet Nam | (88) | TQYVCKRTLVDRGWGNGCGLFGKGSLVTC |
| Z1106033/Suriname/2015 | (88) | TQYVCKRTLVDRGWGNGCGLFGKGSLVTC |
| Zika virus/H. sapiens-tc/THA/2014/SV0127-14 | (88) | TQYVCKRTLVDRGWGNGCGLFGKGSLVTC |
| Zika virus/SZ01/2016/China | (88) | TQYVCKRTLVDRGWGNGCGLFGKGSLVTC |
| ZIKV/Hu/Chiba/S36/2016/Japan | (88) | TQYVCKRTLVDRGWGNGCGLFGKGSLVTC |
| Consensus | (88) | TQYVCKRTLVDRGWGNGCGLFGKGSLVTC |

TABLE 2 -continued

Full E protein amino acid sequences from different strains.

| Strain | | |
|---|---|---|
| | (117) | 117　　　　　　130　　　　　　145 |
| PRVABC59/Puerto Rico | (117) | AKFACSKKMTGKSIQPENLEYRIMLSVHG |
| Brazil/2016/INMI1 | (117) | AKFACSKKMTGKSIQPENLEYRIMLSVHG |
| Central African Republic ARB13565 1976 | (117) | AKFTCSKKMTGKSIQPENLEYRIMLSVHG |
| Nigeria IbH_30656 1968 | (117) | AKFTCSKKMTGKSIQPENLEYRIMLSVHG |
| Senegal ArD_41519 1984 | (117) | AKFTCSKKMTGKSIQPENLEYRIMLSVHG |
| Zika virus/A. africanus-tc/SEN/1984/41525-DAK | (117) | AKFTCSKKMTGKSIQPENLEYRIMLSVHG |
| Zika virus/M. mulatta-tc/UGA/1947/MR-766 | (117) | AKFTCSKKMTGKSIQPENLEYRIMLSVHG |
| Malaysia P6-740 1966 | (117) | AKFACSKKMTGKSIQPENLEYRIMLSVHG |
| CKS63-2014/Cook Islands | (117) | AKFACSKKMTGKSIQPENLEYRIMLSVHG |
| Dominican Republic/2016/PD2 | (117) | AKFACSKKMTGKSIQPENLEYRIMLSVHG |
| ESS23-2015/El Salvador | (117) | AKFACSKKMTGKSIQPENLEYRIMLSVHG |
| FB-GWUH-2016 | (117) | AKFACSKKMTGKSIQPENLEYRIMLSVHG |
| French Polynesia H/PF/2013 2013 | (117) | AKFACSKKMTGKSIQPENLEYRIMLSVHG |
| FS92-2016/Fiji | (117) | AKFACSKKMTGKSIQPENLEYRIMLSVHG |
| Haiti/1225/2014 | (117) | AKFACSKKMTGKSIQPENLEYRIMLSVHG |
| MEX/InDRE/Sm/2016 | (117) | AKFACSKKMTGKSIQPENLEYRIMLSVHG |
| PLCal_ZV/2013/Canada | (117) | AKFACSKKMTGKSIQPENLEYRIMLSVHG |
| VS51-2016/Viet Nam | (117) | AKFACSKKMTGKSIQPENLEYRIMLSVHG |
| Z1106033/Suriname/2015 | (117) | AKFACSKKMTGKSIQPENLEYRIMLSVHG |
| Zika virus/H. sapiens-tc/THA/2014/SV0127-14 | (117) | AKFACSKKMTGKSIQPENLEYRIMLSVHG |
| Zika virus/SZ01/2016/China | (117) | AKFACSKKMTGKSIQPENLEYRIMLSVHG |
| ZIKV/Hu/Chiba/S36/2016/Japan | (117) | AKFACSKKMTGKSIQPENLEYRIMLSVHG |
| Consensus | (117) | AKFACSKKMTGKSIQPENLEYRIMLSVHG |
| | (146) | 146　　　　　　160　　　　　　174 |
| PRVABC59/Puerto Rico | (146) | SQHSGMIVNDTGHETDENRAKVEITPNSP |
| Brazil/2016/INMI1 | (146) | SQHSGMIVNDTGHETDENRAKVEITPNSP |
| Central African Republic ARB13565 1976 | (146) | SQHSGMIVNDIGHETDENRAKVEVTPNSP |
| Nigeria IbH_30656 1968 | (146) | SQHSGMIG----YETDENRAKVEVTPNSP |
| Senegal ArD_41519 1984 | (146) | SQHSGMIVNDTGHETDENRAKVEVTPNSP |
| Zika virus/A. africanus-tc/SEN/1984/41525-DAK | (146) | SQHSGMIVNDTGHETDENRAKVEVTPNSP |
| Zika virus/M. mulatta-tc/UGA/1947/MR-766 | (146) | SQHSGMIVN----DENR--AKVEVTPNSP |
| Malaysia P6-740 1966 | (146) | SQHSGMIVNDXGHETDENRAKVEITPNSP |
| CKS63-2014/Cook Islands | (146) | SQHSGMIVNDTGHETDENRAKVEITPNSP |
| Dominican Republic/2016/PD2 | (146) | SQHSGMIVNDTGHETDENRAKVEITPNSP |
| ESS23-2015/El Salvador | (146) | SQHSGMIVNDTGHETDENRAKVEITPNSP |
| FB-GWUH-2016 | (146) | SQHSGMIVNDTGHETDENRAKVEITPNSP |
| French Polynesia H/PF/2013 2013 | (146) | SQHSGMIVNDTGHETDENRAKVEITPNSP |
| FS92-2016/Fiji | (146) | SQHSGMIVNDTGHETDENRAKVEITPNSP |
| Haiti/1225/2014 | (146) | SQHSGMIVNDTGHETDENRAKVEITPNSP |
| MEX/InDRE/Sm/2016 | (146) | SQHSGMIVNDTGHETDENRAKVEITPNSP |
| PLCal_ZV/2013/Canada | (146) | SQHSGMIVNDTGHETDENRAKVEITPNSP |
| VS51-2016/Viet Nam | (146) | SQHSGMIVNDTGHETDENRAKVEITPNSP |
| Z1106033/Suriname/2015 | (146) | SQHSGMIVNDTGHETDENRAKVEITPNSP |
| Zika virus/H. sapiens-tc/THA/2014/SV0127-14 | (146) | SQHSGMIVNDTGHETDENRAKVEITPNSP |
| Zika virus/SZ01/2016/China | (146) | SQHSGMIVNDTGHETDENRAKVEITPNSP |
| ZIKV/Hu/Chiba/S36/2016/Japan | (146) | SQHSGMIVNDTGHETDENRAKVEITPNSP |
| Consensus | (146) | SQHSGMIVNDTGHETDENRAKVEITPNSP |

TABLE 2 -continued

Full E protein amino acid sequences from different strains.

| | | 175    180         190        203 |
|---|---|---|
| PRVABC59/Puerto Rico | (175) | RAEATLGGFGSLGLDCEPRTGLDFSDLYY |
| Brazil/2016/INMI1 | (175) | RAEATLGGFGSLGLDCEPRTGLDFSDLYY |
| Central African Republic ARB13565 1976 | (175) | RAEATLGGFGSLGLDCEPRTGLDFSDLYY |
| Nigeria IbH_30656 1968 | (175) | RAEATLGGFGSLGLDCEPRTGLDFSDLYY |
| Senegal ArD_41519 1984 | (175) | RAEATLGGFGSLGLDCEPRTGLDFSDLYY |
| Zika virus/A. africanus-tc/SEN/1984/41525-DAK | (175) | RAEATLGGFGSLGLDCEPRTGLDFSDLYY |
| Zika virus/M. mulatta-tc/UGA/1947/MR-766 | (175) | RAEATLGGFGSLGLDCEPRTGLDFSDLYY |
| Malaysia P6-740 1966 | (175) | RAEATLGGFGSLGLDCEPRTGLDFSDLYY |
| CKS63-2014/Cook Islands | (175) | RAEATLGGFGSLGLDCEPRTGLDFSDLYY |
| Dominican Republic/2016/PD2 | (175) | RAEATLGGFGSLGLDCEPRTGLDFSDLYY |
| ESS23-2015/El Salvador | (175) | RAEATLGGFGSLGLDCEPRTGLDFSDLYY |
| FB-GWUH-2016 | (175) | RAEATLGGFGSLGLDCEPRTGLDFSDLYY |
| French Polynesia H/PF/2013 2013 | (175) | RAEATLGGFGSLGLDCEPRTGLDFSDLYY |
| FS92-2016/Fiji | (175) | RAEATLGGFGSLGLDCEPRTGLDFSDLYY |
| Haiti/1225/2014 | (175) | RAEATLGGFGSLGLDCEPRTGLDFSDLYY |
| MEX/InDRE/Sm/2016 | (175) | RAEATLGGFGSLGLDCEPRTGLDFSDLYY |
| PLCal_Zv/2013/Canada | (175) | RAEATLGGFGSLGLDCEPRTGLDFSDLYY |
| VS51-2016/Viet Nam | (175) | RAEATLGGFGSLGLDCEPRTGLDFSDLYY |
| Z1106033/Suriname/2015 | (175) | RAEATLGGFGSLGLDCEPRTGLDFSDLYY |
| Zika virus/H. sapiens-tc/THA/2014/SV0127-14 | (175) | RAEATLGGFGSLGLDCEPRTGLDFSDLYY |
| Zika virus/SZ01/2016/China | (175) | RAEATLGGFGSLGLDCEPRTGLDFSDLYY |
| ZIKV/Hu/Chiba/S36/2016/Japan | (175) | RAEATLGGFGSLGLDCEPRTGLDFSDLYY |
| Consensus | (175) | RAEATLGGFGSLGLDCEPRTGLDFSDLYY |

| | | 204       210        220        232 |
|---|---|---|
| PRVABC59/Puerto Rico | (204) | LTMNNKHWLVHKEWFHDIPLPWHAGADTG |
| Brazil/2016/INMI1 | (204) | LTMNNKHWLVHKEWFHDIPLPWHAGADTG |
| Central African Republic ARB13565 1976 | (204) | LTMNNKHWLVHKEWFHDIPLPWHAGADTG |
| Nigeria IbH_30656 1968 | (204) | LTMNNKHWLVHKEWFHDIPLPWHAGADTG |
| Senegal ArD_41519 1984 | (204) | LTMNNKHWLVHKEWFHDIPLPWHAGADTG |
| Zika virus/A. africanus-tc/SEN/1984/41525-DAK | (204) | LTMNNKHWLVHKEWFHDIPLPWHAGADTG |
| Zika virus/M. mulatta-tc/UGA/1947/MR-766 | (204) | LTMNNKHWLVHKEWFHDIPLPWHAGADTE |
| Malaysia P6-740 1966 | (204) | LTMNNKHWLVHKEWFHDIPLPWHSGADTG |
| CKS63-2014/Cook Islands | (204) | LTMNNKHWLVHKEWFHDIPLPWHAGADTG |
| Dominican Republic/2016/PD2 | (204) | LTMNNKHWLVHKEWFHDIPLPWHTGADTG |
| ESS23-2015/El Salvador | (204) | LTMNNKHWLVHKEWFHDIPLPWHAGADTG |
| FB-GWUH-2016 | (204) | LTMNNKHWLVHKEWFHDIPLPWHAGADTG |
| French Polynesia H/PF/2013 2013 | (204) | LTMNNKHWLVHKEWFHDIPLPWHAGADTG |
| FS92-2016/Fiji | (204) | LTMNNKHWLVHKEWFHDIPLPWHAGADTG |
| Haiti/1225/2014 | (204) | LTMNNKHWLVHKEWFHDIPLPWHAGADTG |
| MEX/InDRE/Sm/2016 | (204) | LTMNNKHWLVHKEWFHDIPLPWHAGADTG |
| PLCal_Zv/2013/Canada | (204) | LTMNNKHWLVHKEWFHDIPLPWHAGADTG |
| VS51-2016/Viet Nam | (204) | LTMNNKHWLVHKEWFHDIPLPWHAGADTG |
| Z1106033/Suriname/2015 | (204) | LTMNNKHWLVHKEWFHDIPLPWHAGADTG |
| Zika virus/H. sapiens-tc/THA/2014/SV0127-14 | (204) | LTMNNKHWLVHKEWFHDIPLPWHAGADTG |
| Zika virus/SZ01/2016/China | (204) | LTMNNKHWLVHKEWFHDIPLPWHAGADTG |
| ZIKV/Hu/Chiba/S36/2016/Japan | (204) | LTMNNKHWLVHKEWFHDIPLPWHAGADTG |
| Consensus | (204) | LTMNNKHWLVHKEWFHDIPLPWHAGADTG |

TABLE 2 -continued

Full E protein amino acid sequences from different strains.

| | | |
|---|---|---|
| | (233) | 233 240 250 261 |
| PRVABC59/Puerto Rico | (233) | TPHWNNKEALVEFKDAHAKRQTVVVLGSQ |
| Brazil/2016/INMI1 | (233) | TPHWNNKEALVEFKDAHAKRQTVVVLGSQ |
| Central African Republic ARB13565 1976 | (233) | TPHWNNKEALVEFKDAHAKRQTVVVLGSQ |
| Nigeria IbH_30656 1968 | (233) | TPHWNNKEALVEFKDAHAKRQTVVVLGSQ |
| Senegal ArD_41519 1984 | (233) | TPHWNNKEALVEFKDAHAKRQTVVVLGSQ |
| Zika virus/A. africanus-tc/SEN/1984/41525-DAK | (233) | TPHWNNKEALVEFKDAHAKRQTVVVLGSQ |
| Zika virus/M. mulatta-tc/UGA/1947/MR-766 | (233) | TPHWNNKEALVEFKDAHAKRQTVVVLGSQ |
| Malaysia P6-740 1966 | (233) | TPHWNNKEALVEFKDAHAKRQTVVVLGSQ |
| CKS63-2014/Cook Islands | (233) | TPHWNNKEALVEFKDAHAKRQTVVVLGSQ |
| Dominican Republic/2016/PD2 | (233) | TPHWNNKEALVEFKDAHAKRQTVVVLGSQ |
| ESS23-2015/El Salvador | (233) | TPHWNNKEALVEFKDAHAKRQTVVVLGSQ |
| FB-GWUH-2016 | (233) | TPHWNNKEALVEFKDAHAKRQTVVVLGSQ |
| French Polynesia H/PF/2013 2013 | (233) | TPHWNNKEALVEFKDAHAKRQTVVVLGSQ |
| FS92-2016/Fiji | (233) | TPHWNNKEALVEFKDAHAKRQTVVVLGSQ |
| Haiti/1225/2014 | (233) | TPHWNNKEALVEFKDAHAKRQTVVVLGSQ |
| MEX/InDRE/Sm/2016 | (233) | TPHWNNKEALVEFKDAHAKRQTVVVLGSQ |
| PLCal_Zv/2013/Canada | (233) | TPHWNNKEALVEFKDAHAKRQTVVVLGSQ |
| VS51-2016/Viet Nam | (233) | TPHWNNKEALVEFKDAHAKRQTVVVLGSQ |
| Z1106033/Suriname/2015 | (233) | TPHWNNKEALVEFKDAHAKRQTVVVLGSQ |
| Zika virus/H. sapiens-tc/THA/2014/SV0127-14 | (233) | TPHWNNKEALVEFKDAHAKRQTVVVLGSQ |
| Zika virus/SZ01/2016/China | (233) | TPHWNNKEALVEFKDAHAKRQTVVVLGSQ |
| ZIKV/Hu/Chiba/S36/2016/Japan | (233) | TPHWNNKEALVEFKDAHAKRQTVVVLGSQ |
| Consensus | (233) | TPHWNNKEALVEFKDAHAKRQTVVVLGSQ |
| | (262) | 262 270 260 290 |
| PRVABC59/Puerto Rico | (262) | EGAVHTALAGALEAEMDGAKGRLSSGHLK |
| Brazil/2016/INMI1 | (262) | EGAVHTALAGALEAEMDGAKGRLSSGHLK |
| Central African Republic ARB13565 1976 | (262) | EGAVHTALAGALEAEMDGAKGRLFSGHLK |
| Nigeria IbH_30656 1968 | (262) | EGAVHTALAGALEAEMDGAKGRLFSGHLK |
| Senegal ArD_41519 1984 | (262) | EGAVHTALAGALEAEMDGAKGRLFSGHLK |
| Zika virus/A. africanus-tc/SEN/1984/41525-DAK | (262) | EGAVHTALAGALEAEMDGAKGRLFSGHLK |
| Zika virus/M. mulatta-tc/UGA/1947/MR-766 | (262) | EGAVHTALAGALEAEMDGAKGRLSSGHLK |
| Malaysia P6-740 1966 | (262) | EGAVHTALAGALEAEMDGAKGRLSSGHLK |
| CKS63-2014/Cook Islands | (262) | EGAVHTALAGALEAEMDGAKGRLSSGHLK |
| Dominican Republic/2016/PD2 | (262) | EGAVHTALAGALEAEMDGAKGRLSSGHLK |
| ESS23-2015/El Salvador | (262) | EGAVHTALAGALEAEMDGAKGRLSSGHLK |
| FB-GWUH-2016 | (262) | EGAVHTALAGALEAEMDGAKGRLSSGHLK |
| French Polynesia H/PF/2013 2013 | (262) | EGAVHTALAGALEAEMDGAKGRLSSGHLK |
| FS92-2016/Fiji | (262) | EGAVHTALAGALEAEMDGAKGRLSSGHLK |
| Haiti/1225/2014 | (262) | EGAVHTALAGALEAEMDGAKGRLSSGHLK |
| MEX/InDRE/Sm/2016 | (262) | EGAVHTALAGALEAEMDGAKGRLSSGHLK |
| PLCal_Zv/2013/Canada | (262) | EGAVHTALAGALEAEMDGAKGRLSSGHLK |
| VS51-2016/Viet Nam | (262) | EGAVHTALAGALEAEMDGAKGRLSSGHLK |
| Z1106033/Suriname/2015 | (262) | EGAVHTALAGALEAEMDGAKGRLSSGHLK |
| Zika virus/H. sapiens-tc/THA/2014/SV0127-14 | (262) | EGAVHTALAGALEAEMDGAKGRLSSGHLK |
| Zika virus/SZ01/2016/China | (262) | EGAVHTALAGALEAEMDGAKGRLSSGHLK |
| ZIKV/Hu/Chiba/S36/2016/Japan | (262) | EGAVHTALAGALEAEMDGAKGRLSSGHLK |
| Consensus | (262) | EGAVHTALAGALEAEMDGAKGRLSSGHLK |

TABLE 2 -continued

Full E protein amino acid sequences from different strains.

| Strain | | Sequence |
|---|---|---|
| | (291) | 291        300           319 |
| PRVABC59/Puerto Rico | (291) | CRLKMDKLRLKGVSYSLCTAAFTFTKIPA |
| Brazil/2016/INMI1 | (291) | CRLKMDKLRLKGVSYSLCTAAFTFTKIPA |
| Central African Republic ARB13565 1976 | (291) | CRLKMDKLRLKGVSYSLCTAAFTFTKVPA |
| Nigeria IbH_30656 1968 | (291) | CRLKMDKLRLKGVSYSLCTAAFTFTKVPA |
| Senegal ArD_41519 1984 | (291) | CRLKMDKLRLKGVSYSLCTAAFTFTKVPA |
| Zika virus/A. africanus-tc/SEN/1984/41525-DAK | (291) | CRLKMDKLRLKGVSYSLCTAAFTFTKVPA |
| Zika virus/M. mulatta-tc/UGA/1947/MR-766 | (291) | CRLKMDKLRLKGVSYSLCTAAFTFTKVPA |
| Malaysia P6-740 1966 | (291) | CRLKMDKLRLKGVSYSLCTAAFTFTKIPA |
| CKS63-2014/Cook Islands | (291) | CRLKMDKLRLKGVSYSLCTAAFTFTKIPA |
| Dominican Republic/2016/PD2 | (291) | CRLKMDKLRLKGVSYSLCTAAFTFTKIPA |
| ESS23-2015/El Salvador | (291) | CRLKMDKLRLKGVSYSLCTAAFTFTKIPA |
| FB-GWUH-2016 | (291) | CRLKMDKLRLKGVSYSLCTAAFTFTKIPA |
| French Polynesia H/PF/2013 2013 | (291) | CRLKMDKLRLKGVSYSLCTAAFTFTKIPA |
| FS92-2016/Fiji | (291) | CRLKMDKLRLKGVSYSLCTAAFTFTKIPA |
| Haiti/1225/2014 | (291) | CRLKMDKLRLKGVSYSLCTAAFTFTKIPA |
| MEX/InDRE/Sm/2016 | (291) | CRLKMDKLRLKGVSYSLCTAAFTFTKIPA |
| PLCal_Zv/2013/Canada | (291) | CRLKMDKLRLKGVSYSLCTAAFTFTKIPA |
| VS51-2016/Viet Nam | (291) | CRLKMDKLRLKGVSYSLCTAAFTFTKIPA |
| Z1106033/Suriname/2015 | (291) | CRLKMDKLRLKGVSYSLCTAAFTFTKIPA |
| Zika virus/H. sapiens-tc/THA/2014/SV0127-14 | (291) | CRLKMDKLRLKGVSYSLCTAAFTFTKIPA |
| Zika virus/SZ01/2016/China | (291) | CRLKMDKLRLKGVSYSLCTAAFTFTKIPA |
| ZIKV/Hu/Chiba/S36/2016/Japan | (291) | CRLKMDKLRLKGVSYSLCTAAFTFTKIPA |
| Consensus | (291) | CRLKMDKLRLKGVSYSLCTAAFTFTKIPA |
| | (320) | 320       330            348 |
| PRVABC59/Puerto Rico | (320) | ETLHGTVTVELQYAGTDGPCKVPAQMAVD |
| Brazil/2016/INMI1 | (320) | ETLHGTVTVEVQYAGTDGPCKVPAQMAVD |
| Central African Republic ARB13565 1976 | (320) | ETLHGTVTVEVQYAGTDGPCKVPAQMAVD |
| Nigeria IbH_30656 1968 | (320) | ETLHGTVTVEVQYAGTDGPCKIPVQMAVD |
| Senegal ArD_41519 1984 | (320) | ETLHGTVTVEVQYAGTDGPCKVPAQMAVD |
| Zika virus/A. africanus-tc/SEN/1984/41525-DAK | (320) | ETLHGTVTVEVQYAGTDGPCKVPAQMAVD |
| Zika virus/M. mulatta-tc/UGA/1947/MR-766 | (320) | ETLHGTVTVEVQYAGRDGPCKVPAQMAVD |
| Malaysia P6-740 1966 | (320) | ETLHGTVTVEVQYAGTDGPCKVPAQMAVD |
| CKS63-2014/Cook Islands | (320) | ETLHGTVTVEVQYAGTDGPCKVPAQMAVD |
| Dominican Republic/2016/PD2 | (320) | ETLHGTVTVEVQYAGTDGPCKVPAQMAVD |
| ESS23-2015/El Salvador | (320) | ETLHGTVTVEVQYAGTDGPCKVPAQMAVD |
| FB-GWUH-2016 | (320) | ETLHGTVTVEVQYAGTDGPCKVPAQMAVD |
| French Polynesia H/PF/2013 2013 | (320) | ETLHGTVTVEVQYAGTDGPCKVPAQMAVD |
| FS92-2016/Fiji | (320) | ETLHGTVTVEVQYAGTDGPCKVPAQMAVD |
| Haiti/1225/2014 | (320) | ETLHGTVTVEVQYAGTDGPCKVPAQMAVD |
| MEX/InDRE/Sm/2016 | (320) | ETLHGTVTVEVQYAGTDGPCKVPAQMAVD |
| PLCal_Zv/2013/Canada | (320) | ETLHGTVTVEVQYAGTDGPCKVPAQMAVD |
| VS51-2016/Viet Nam | (320) | ETLHGTVTVEVQYAGTDGPCKVPAQMAVD |
| Z1106033/Suriname/2015 | (320) | ETLHGTVTVEVQYAGTDGPCKVPAQMAVD |
| Zika virus/H. sapiens-tc/THA/2014/SV0127-14 | (320) | ETLHGTVTVEVQYAGTDGPCKVPAQMAVD |
| Zika virus/SZ01/2016/China | (320) | ETLHGTVTVEVQYAGTDGPCKVPAQMAVD |
| ZIKV/Hu/Chiba/S36/2016/Japan | (320) | ETLHGTVTVEVQYAGTDGPCKVPAQMAVD |
| Consensus | (320) | ETLHGTVTVEVQYAGTDGPCKVPAQMAVD |

TABLE 2 -continued

Full E protein amino acid sequences from different strains.

| | | |
|---|---|---|
| | (349) | 349        360         377 |
| PRVABC59/Puerto Rico | (349) | MQTLTPVGRLITANPVITESTENSKMMLE |
| Brazil/2016/INMI1 | (349) | MQTLTPVGRLITANPVITESTENSKMMLE |
| Central African Republic ARB13565 1976 | (349) | MQTLTPVGRLITANPVITESTENSKMMLE |
| Nigeria IbH_30656 1968 | (349) | MQTLTPVGRLITANPVITESTENSKMMLE |
| Senegal ArD_41519 1984 | (349) | MQTLTPVGRLITANPVITESTENSKMMLE |
| Zika virus/A. africanus-tc/SEN/1984/41525-DAK | (349) | MQTLTPVGRLITANPVITESTENSKMMLE |
| Zika virus/M. mulatta-tc/UGA/1947/MR-766 | (349) | MQTLTPVGRLITANPVITESTENSKMMLE |
| Malaysia P6-740 1966 | (349) | MQTLTPVGRLITANPVITESTENSKMMLE |
| CKS63-2014/Cook Islands | (349) | MQTLTPVGRLITANPVITEGTENSKMMLE |
| Dominican Republic/2016/PD2 | (349) | MQTLTPVGRLITANPVITESTENSKMMLE |
| ESS23-2015/El Salvador | (349) | MQTLTPVGRLITANPVITESTENSKMMLE |
| FB-GWUH-2016 | (349) | MQTLTPVGRLITANPVITESTENSKMMLE |
| French Polynesia H/PF/2013 2013 | (349) | MQTLTPVGRLITANPVITESTENSKMMLE |
| FS92-2016/Fiji | (349) | MQTLTPVGRLITANPVITESTENSKMMLE |
| Haiti/1225/2014 | (349) | MQTLTPVGRLITANPVITESTENSKMMLE |
| MEX/InDRE/Sm/2016 | (349) | MQTLTPVGRLITANPVITESTENSKMMLE |
| PLCal_Zv/2013/Canada | (349) | MQTLTPVGRLITANPVITESTENSKMMLE |
| VS51-2016/Viet Nam | (349) | MQTLTPVGRLITANPVITESTENSKMMLE |
| Z1106033/Suriname/2015 | (349) | MQTLTPVGRLITANPVITESTENSKMMLE |
| Zika virus/H. sapiens-tc/THA/2014/SV0127-14 | (349) | MQTLTPVGRLITANPVITESTENSKMMLE |
| Zika virus/SZ01/2016/China | (349) | MQTLTPVGRLITANPVITESTENSKMMLE |
| ZIKV/Hu/Chiba/S36/2016/Japan | (349) | MQTLTPVGRLITANPVITESTENSKMMLE |
| Consensus | (349) | MQTLTPVGRLITANPVITESTENSKMMLE |
| | (378) | 378        390         406 |
| PRVABC59/Puerto Rico | (378) | LDPPFGDSYIVIGVGEKKITHHWHRSGST |
| Brazil/2016/INMI1 | (378) | LDPPFGDSYIVIGVGEKKITHHWHRSGST |
| Central African Republic ARB13565 1976 | (378) | LDPPFGDSYIVIGVGDKKITHHWHRSGST |
| Nigeria IbH_30656 1968 | (378) | LDPPFGDSYIVIGVGDKKITHHWHRSGST |
| Senegal ArD_41519 1984 | (378) | LDPPFGDSYIVIGVGDKKITHHWHRSGST |
| Zika virus/A. africanus-tc/SEN/1984/41525-DAK | (378) | LDPPFGDSYIVIGVGDKKITHHWHRSGST |
| Zika virus/M. mulatta-tc/UGA/1947/MR-766 | (378) | LDPPFGDSYIVIGVGDKKITHHWHRSGSI |
| Malaysia P6-740 1966 | (378) | LDPPFGDSYIVIGVGDKKITHHWXRSGST |
| CKS63-2014/Cook Islands | (378) | LDPPFGDSYIVIGVGEKKITHHWHRSGST |
| Dominican Republic/2016/PD2 | (378) | LDPPFGDSYIVIGVGEKKITHHWHRSGST |
| ESS23-2015/El Salvador | (378) | LDPPFGDSYIVIGVGEKKITHHWHRSGST |
| FB-GWUH-2016 | (378) | LDPPFGDSYIVIGVGEKKITHHWHRSGST |
| French Polynesia H/PF/2013 2013 | (378) | LDPPFGDSYIVIGVGEKKITHHWHRSGST |
| FS92-2016/Fiji | (378) | LDPPFGDSYIVIGIGEKKITHHWHRSGST |
| Haiti/1225/2014 | (378) | LDPPFGDSYIVIGVGEKKITHHWHRSGST |
| MEX/InDRE/Sm/2016 | (378) | LDPPFGDSYIVIGVGEKKITHHWHRSGST |
| PLCal_Zv/2013/Canada | (378) | LDPPFGDSYIVIGVGEKKITHHWHRSGST |
| VS51-2016/Viet Nam | (378) | LDPPFGDSYIVIGVGEKKITHHWHRSGST |
| Z1106033/Suriname/2015 | (378) | LDPPFGDSYIVIGVGEKKITHHWHRSGST |
| Zika virus/H. sapiens-tc/THA/2014/SV0127-14 | (378) | LDPPFGDSYIVIGVGEKKITHHWHRSGST |
| Zika virus/SZ01/2016/China | (378) | LDPPFGDSYIVIGVGEKKITHHWHRSGST |
| ZIKV/Hu/Chiba/S36/2016/Japan | (378) | LDPPFGDSYIVIGVGEKKITHHWHRSGST |
| Consensus | (378) | LDPPFGDSYIVIGVGEKKITHHWHRSGST |

TABLE 2 -continued

Full E protein amino acid sequences from different strains.

| | | 407 | 420 | 435 |
|---|---|---|---|---|
| PRVABC59/Puerto Rico | (407) | IGKAFEATVRGAKRMAVLGDTAWDFGSVG | | |
| Brazil/2016/INMI1 | (407) | IGKAFEATVRGAKRMAVLGDTAWDFGSVG | | |
| Central African Republic ARB13565 1976 | (407) | IGKAFEATVRGAKRMAVLGDTAWDFGSVG | | |
| Nigeria IbH_30656 1968 | (407) | IGKAFEATVRGAKRMAVLGDTAWDFGSVG | | |
| Senegal ArD_41519 1984 | (407) | IGKAFEATVRGAKRMAVLGDTAWDFGSVG | | |
| Zika virus/A. africanus-tc/SEN/1984/41525-DAK | (407) | IGKAFEATVRGAKRMAVLGDTAWDFGSVG | | |
| Zika virus/M. mulatta-tc/UGA/1947/MR-766 | (407) | IGKAFEATVRGAKRMAVLGDTAWDFGSVG | | |
| Malaysia P6-740 1966 | (407) | IGKAFEATVRGAKRMAVLGDTAWDFGSVG | | |
| CKS63-2014/Cook Islands | (407) | IGKAFEATVRGAKRMAVLGDTAWDFGSVG | | |
| Dominican Republic/2016/PD2 | (407) | IGKAFEATVRGAKRMAVLGDTAWDFGSVG | | |
| ESS23-2015/El Salvador | (407) | IGKAFEATVRGAKRMAVLGDTAWDFGSVG | | |
| FB-GWUH-2016 | (407) | IGKAFEATVRGAKRMAVLGDTAWDFGSVG | | |
| French Polynesia H/PF/2013 2013 | (407) | IGKAFEATVRGAKRMAVLGDTAWDFGSVG | | |
| FS92-2016/Fiji | (407) | IGKAFEATVRGAKRMAVLGDTAWDFGSVG | | |
| Haiti/1225/2014 | (407) | IGKAFEATVRGAKRMAVLGDTAWDFGSVG | | |
| MEX/InDRE/Sm/2016 | (407) | IGKAFEATVRGAKRMAVLGDTAWDFGSVG | | |
| PLCal_Zv/2013/Canada | (407) | IGKAFEATVRGAKRMAVLGDTAWDFGSVG | | |
| VS51-2016/Viet Nam | (407) | IGKAFEATVRGAKRMAVLGDTAWDFGSVG | | |
| Z1106033/Suriname/2015 | (407) | IGKAFEATVRGAKRMAVLGDTAWDFGSVG | | |
| Zika virus/H. sapiens-tc/THA/2014/SV0127-14 | (407) | IGKAFEATVRGAKRMAVLGDTAWDFGSVG | | |
| Zika virus/SZ01/2016/China | (407) | IGKAFEATVRGARRMAVLGDTAWDFGSVG | | |
| ZIKV/Hu/Chiba/S36/2016/Japan | (407) | IGKAFEATVRGAKRMAVLGDTAWDFGSVG | | |
| Consensus | (407) | IGKAFEATVRGAKRMAVLGDTAWDFGSVG | | |

| | | 436 | 450 | 464 |
|---|---|---|---|---|
| PRVABC59/Puerto Rico | (436) | GALNSLGKGIHQIFGAAFKSLFGGMSWFS | | |
| Brazil/2016/INMI1 | (436) | GALNSLGKGIHQIFGAAFKSLFGGMSWFS | | |
| Central African Republic ARB13565 1976 | (436) | GVFNSLGKGVHQIFGAAFKSLFGGMSWFS | | |
| Nigeria IbH_30656 1968 | (436) | GVFNSLGKGIHQIFGAAFKSLFGGMSWFS | | |
| Senegal ArD_41519 1984 | (436) | GVFNSLGKGIHQIFGAAFKSLFGGMSWFS | | |
| Zika virus/A. africanus-tc/SEN/1984/41525-DAK | (436) | GVFNSLGKGIHQIFGAAFKSLFGGMSWFS | | |
| Zika virus/M. mulatta-tc/UGA/1947/MR-766 | (436) | GVFNSLGKGIHQIFGAAFKSLFGGMSWFS | | |
| Malaysia P6-740 1966 | (436) | GALNSLGKGIHQIFGAAFKSLFGGMSWFS | | |
| CKS63-2014/Cook Islands | (436) | GVLNSLGKGIHQIFGAAFKSLFGGMSWFS | | |
| Dominican Republic/2016/PD2 | (436) | GALNSLGKGIHQIFGAAFKSLFGGMSWFS | | |
| ESS23-2015/El Salvador | (436) | GALNSLGKGIHQIFGAAFKSLFGGMSWFS | | |
| FB-GWUH-2016 | (436) | GALNSLGKGIHQIFGAAFKSLFGGMSWFS | | |
| French Polynesia H/PF/2013 2013 | (436) | GALNSLGKGIHQIFGAAFKSLFGGMSWFS | | |
| FS92-2016/Fiji | (436) | GALNSLGKGIHQIFGAAFKSLFGGMSWFS | | |
| Haiti/1225/2014 | (436) | GALNSLGKGIHQIFGAAFKSLFGGMSWFS | | |
| MEX/InDRE/Sm/2016 | (436) | GALNSLGKGIHQIFGAAFKSLFGGMSWFS | | |
| PLCal_Zv/2013/Canada | (436) | GALNSLGKGIHQIFGAAFKSLFGGMSWFS | | |
| VS51-2016/Viet Nam | (436) | GALNSLGKGIHQIFGAAFKSLFGGMSWFS | | |
| Z1106033/Suriname/2015 | (436) | GALNSLGKGIHQIFGAAFKSLFGGMSWFS | | |
| Zika virus/H. sapiens-tc/THA/2014/SV0127-14 | (436) | GALNSLGKGIHQIFGAAFKSLFGGMSWFS | | |
| Zika virus/SZ01/2016/China | (436) | GALNSLGKGIHQIFGAAFKSLFGGMSWFS | | |
| ZIKV/Hu/Chiba/S36/2016/Japan | (436) | GALNSLGKGIHQIFGAAFKSLFGGMSWFS | | |
| Consensus | (436) | GALNSLGKGIHQIFGAAFKSLFGGMSWFS | | |

TABLE 2 -continued

Full E protein amino acid sequences from different strains.

| | (465) | 465 470 480 493 |
|---|---|---|
| PRVABC59/Puerto Rico | (465) | QILIGTLIMWLGLNTKNGSISLMCLALGG |
| Brazil/2016/INMI1 | (465) | QILIGTLLMWLGLNTKNGSISLMCLALGG |
| Central African Republic ARB13565 1976 | (465) | QILIGTLLVWLGLNTKNGSISLTCLALGG |
| Nigeria IbH_30656 1968 | (465) | QILIGTLLVWLGLNTKNGSISLTCLALGG |
| Senegal ArD_41519 1984 | (465) | QILIGTLLVWLGLNTKNGSISLTCLALGG |
| Zika virus/A. africanus-tc/SEN/1984/41525-DAK | (465) | QILIGTLLVWLGLNTKNGSISLTCLALGG |
| Zika virus/M. mulatta-tc/UGA/1947/MR-766 | (465) | QILIGTLLVWLGLNTKNGSISLTCLALGG |
| Malaysia P6-740 1966 | (465) | QILIGTLLVWLGLNTKNGSISLTCLALGG |
| CKS63-2014/Cook Islands | (465) | QILIGTLLVWLGLNTKNGSISLTCLALGG |
| Dominican Republic/2016/PD2 | (465) | QILIGTLLMWLGLNTKNGSISLMCLALGG |
| ESS23-2015/El Salvador | (465) | QILIGTLLMWLGLNTKNGSISLMCLALGG |
| FB-GWUH-2016 | (465) | QILIGTLLMWLGLNTKNGSISLMCLALGG |
| French Polynesia H/PF/2013 2013 | (465) | QILIGTLLMWLGLNTKNGSISLMCLALGG |
| FS92-2016/Fiji | (465) | QILIGTLLMWLGLNTKNGSISLMCLALGG |
| Haiti/1225/2014 | (465) | QILIGTLLMWLGLNTKNGSISLMCLALGG |
| MEX/InDRE/Sm/2016 | (465) | QILIGTLLMWLGLNTKNGSISLMCLALGG |
| PLCal_Zv/2013/Canada | (465) | QILIGTLLMWLGLNTKNGSISLMCLALGG |
| VS51-2016/Viet Nam | (465) | QILIGTLLMWLGLNTKNGSISLMCLALGG |
| Z1106033/Suriname/2015 | (465) | QILIGTLLMWLGLNTKNGSISLMCLALGG |
| Zika virus/H. sapiens-tc/THA/2014/SV0127-14 | (465) | QILIGTLLMWLGLNAKNGSISLMCLALGG |
| Zika virus/SZ01/2016/China | (465) | QILIGTLLMWLGLNTKNGSISLMCLALGG |
| ZIKV/Hu/Chiba/S36/2016/Japan | (465) | QILIGTLLMWLGLNTKNGSISLMCLALGG |
| Consensus | (465) | QILIGTLLMWLGLNTKNGSISLMCLALGG |

| | (494) | 494 504 |
|---|---|---|
| PRVABC59/Puerto Rico | (494) | VLIFLSTAVSA |
| Brazil/2016/INMI1 | (494) | VLIFLSTAVSA |
| Central African Republic ARB13565 1976 | (494) | VMIFLSTAVSA |
| Nigeria IbH_30656 1968 | (494) | VMIFLSTAVSA |
| Senegal ArD_41519 1984 | (494) | VMIFLSTAVSA |
| Zika virus/A. africanus-tc/SEN/1984/41525-DAK | (494) | VMIFLSTAVSA |
| Zika virus/M. mulatta-tc/UGA/1947/MR-766 | (494) | VMIFLSTAVSA |
| Malaysia P6-740 1966 | (494) | VLIFLSTAVSA |
| CKS63-2014/Cook Islands | (494) | VLIFLSTAVSA |
| Dominican Republic/2016/PD2 | (494) | VLIFLSTAVSA |
| ESS23-2015/El Salvador | (494) | VLIFLSTAVSA |
| FB-GWUH-2016 | (494) | VLIFLSTAVSA |
| French Polynesia H/PF/2013 2013 | (494) | VLIFLSTAVSA |
| FS92-2016/Fiji | (494) | VLIFLSTAVSA |
| Haiti/1225/2014 | (494) | VLIFLSTAVSA |
| MEX/InDRE/Sm/2016 | (494) | VLIFLSTAVSA |
| PLCal_Zv/2013/Canada | (494) | VLIFLSTAVSA |
| VS51-2016/Viet Nam | (494) | VLIFLSTAVSA |
| Z1106033/Suriname/2015 | (494) | VLIFLSTAVSA |
| Zika virus/H. sapiens-tc/THA/2014/SV0127-14 | (494) | VLIFLSTAVSA |
| Zika virus/SZ01/2016/China | (494) | VLIFLSTAVSA |
| ZIKV/Hu/Chiba/S36/2016/Japan | (494) | VLIFLSTAVSA |
| Consensus | (494) | VLIFLSTAVSA |

In another embodiment, the vaccine comprises a zE polypeptide that is a full-length version of the ZIKA E protein. In some embodiments, the vaccine comprises a sequence of SEQ ID NO: 13, which can be found at Genebank Acc. No. AMC13911.1 (amino acid 291-723), or a functionally equivalent version of the full-length version of SEQ ID NO: 13 (IRCIGVSNRDFVEG-MSGGTWVDVVLEHGGCVTVMAQDKPTVDIELVTTT VSNMAEVR SYCYEASISDMASDSRCPTQGEAY-LDKQSDTQYVCKRTLVDRGWGNGCGLFGKGSLVT CAKFACSKKMTGKSIQPENLEYRIMLSVHGSQHSG-MIVNDTGHETDENRAKVEITPNSP RAEATLGGFGSLGLDCEPRTGLDFSD- LYYLTMNNKHWLVHKEWFHDIPLPWHAGADT GTPHWNNKEALVEFKDA-HAKRQTVVVLGSQEGAVHTALAGALEAEMD-GAKGRLSSG HLKCRLKMDKLRLKGVSYSLCTAAF-TFTKIPAETLHGTVTVEVQYAGTDGPCKVPAQM AVDMQTLTPVGRLITANPVITESTENSKM-MLELDPPFGDSYIVIGVGEKKITHHWHRSGS TIGKAFEATVRGAKRMAVLGDTAWDFGS). As used herein, the term "functionally equivalent" refers to a zE polypeptide fragment that retains at least 90% activity of the sequence defined as SEQ ID NO: 13. In yet another embodiment, the vaccine comprises a zE polypeptide fragment that is a part of a full-length version of SEQ ID NO: 13 and the zE polypeptide fragment retains at least 90% activity of the sequence defined as SEQ ID NO: 13.

In another embodiment, the vaccine comprises a zE polypeptide that is a full-length version of ZIKA E protein, but with its FL epitope mutated by substitutions of amino acids (zE-FL-mutant). In some embodiment, the vaccine comprises a zE-FL-mutant having a sequence of SEQ ID NO: 14 (IRCIGVSNRDFVEG-MSGGTWVDVVLEHGGCVTVMAQDKPTVDIELVTTT VSNMAEVR SYCYEASISDMASDSRCPREGEAY-LDKQSDTQYVCKRTLVDRGRGNGCGRFGKGSLVT CAKFACSKKMTGKSIQPENLEYRIMLSVHGSQHSG-MIVNDTGHETDENRAKVEITPNSP RAEATLGGFGSLGLDCEPRTGLDFSD-LYYLTMNNKHWLVHKEWFHDIPLPWHAGADT GTPHWNNKEALVEFKDA-HAKRQTVVVLGSQEGAVHTALAGALEAEMD-GAKGRLSSG HLKCRLKMDKLRLKGVSYSLCTAAF-TFTKIPAETLHGTVTVEVQYAGTDGPCKVPAQM AVDMQTLTPVGRLITANPVITESTENSKM-MLELDPPFGDSYIVIGVGEKKITHHWHRSGS TIGKAFEATVRGAKRMAVLGDTAWDFGS). The mutations include but not limited to substitutions of threonine (T) at position 76 by arginine (R) (T76R), glutamine (Q) at position 77 by glutamic acid (E) (Q77E), tryptophan (W) at position 101 by arginine (R) (W101R) and leucine (L) at position 107 by R (L107R). These mutations in FL epitope are not meant to be limiting. Indeed, the zE-FL-mutant may comprises other suitable mutations in the FL epitope that are able to reduce the likelihood of inducing cross-reactive FL-specific antibodies. In yet other embodiments, the vaccine comprises a zE-FL-mutant polypeptide fragment that is a part of a full-length version of SEQ ID NO: 14 and the zE-FL-mutant polypeptide fragment retains at least 90% activity of the sequence defined as SEQ ID NO: 14.

As used herein, "VLPs" resemble viruses, but are non-infectious because they contain no viral genetic material. The expression of viral structural proteins, such as Envelope or Capsid, can result in the self-assembly of virus like particles (VLPs). VLPs have been produced from components of a wide variety of virus families including Parvoviridae (e.g. adeno-associated virus), Retroviridae (e.g. HIV), Flaviviridae (e.g. Hepatitis C virus) and bacteriophages (e.g. Q3, AP205). VLPs can be produced in multiple cell culture systems including bacteria, mammalian cell lines, insect cell lines, yeast, and plant cells. VLPs are useful as vaccines. VLPs contain repetitive, high density displays of viral surface proteins that present conformational viral epitopes that can elicit strong T cell and B cell immune responses. Since VLPs cannot replicate, they provide a safer alternative to attenuated viruses. In an exemplary embodiment, VLPs are derived from Hepatitis B virus core antigen (HBcAg) comprising amino acid sequence of SEQ ID NO:2 or a functionally equivalent version of SEQ ID NO:2 (MDIDPYKEFGATVELLSFLPSDFFPSVRDLLD-TASALYREALESPEHCSPHHTALRQAIL CWGELMT-LATWVGNNLEDPASRDLVVNYVNTNVGLKIRQLL-WFHISCLTFGRETVLEY LVSFGVWIRTPPAYRPPNAPILSTLPETTVVRRRDRG). SEQ ID NO: 2 is not meant to be limiting.

In certain embodiments, vaccines provided herein can be formed by incorporating one or more VLPs displaying a portion of zDIII polypeptide into pharmaceutically acceptable formulations. In other embodiments, vaccines provided herein can be formed by incorporating one or more VLPs displaying at least a portion of zE protein into pharmaceutically acceptable formulations. In yet other embodiments, vaccines provided herein can be formed by incorporating a portion of zE protein into pharmaceutically acceptable formulations. The formulations may contain pharmaceutically acceptable adjuvants (such as oils, surfactants, alum), immunostimulating agents (such as phospholipids, glycolipids, glycans, glycopeptides, or lipopeptides), and one or more diluents ("excipients"). Examples of diluents suitable for use are water, phosphate buffered saline, 0.15 M sodium chloride solution, dextrose, glycerol, mannitol, sorbitol, dilute ethanol, and mixtures thereof. Pharmaceutically acceptable unit dosage forms of the vaccines can be formulated as solutions, emulsions, dispersions, tablets, or capsules.

In certain embodiments, a vaccine composition of the current technology further comprises an immunological adjuvant. The terms "immunological adjuvant" and "adjuvant" refer to an agent which acts in a nonspecific manner to increase an immune response to a particular antigen or combination of antigens, thus reducing the quantity of antigen necessary in any given vaccine and/or the frequency of injection necessary in order to generate an adequate immune response to the antigen of interest. Such adjuvants and their use are known and available to those who practice in the art and can include, for example, emulsifiers, muramyl dipeptides, avridine, aqueous adjuvants such as aluminum hydroxide, chitosan-based adjuvants, and any of the various saponins, oils, and other substances known in the art, such as Amphigen, LPS, bacterial cell wall extracts, bacterial DNA, synthetic oligonucleotides and combinations thereof (e.g., Schijns et al., *Curr. Opi. Immunol.* (2000) 12:456 (2000)). Compounds that can serve as emulsifiers herein include natural and synthetic emulsifying agents, as well as anionic, cationic and nonionic compounds. Among the synthetic compounds, anionic emulsifying agents include, for example, the potassium, sodium and ammonium salts of lauric and oleic acid, the calcium, magnesium and aluminum salts of fatty acids (i.e., metallic soaps), and organic sulfonates such as sodium lauryl sulfate.

Further, in certain embodiments, the vaccine composition of the current technology may comprise other suitable agents that stabilize the formulations. For example, an approach for stabilizing solid protein formulations of the current technology is to increase the physical stability of purified, e.g., lyophilized, protein. This will inhibit aggregation via hydrophobic interactions as well as via covalent pathways that may increase as proteins unfold. Stabilizing formulations in this context may often include polymer-based formulations, for example a biodegradable hydrogel formulation/delivery system. The critical role of water in protein structure, function, and stability is well known. Typically, proteins are relatively stable in the solid state with bulk water removed. However, solid therapeutic protein formulations may become hydrated upon storage at elevated humidities or during delivery from a sustained release composition or device. The stability of proteins generally drops with increasing hydration. Water may also play a significant role in solid protein aggregation, for example, by increasing protein flexibility resulting in enhanced accessibility of reactive groups, by providing a mobile phase for reactants, and by serving as a reactant in several deleterious processes such as beta-elimination and hydrolysis.

An effective method for stabilizing peptides and proteins against solid-state aggregation for delivery may be to control the water content in a solid formulation and maintain the water activity in the formulation at optimal levels. This level depends on the nature of the protein, but in general, proteins maintained below their "monolayer" water coverage will exhibit superior solid-state stability.

Moreover, methods for preventing ZIKA virus infection are provided. In certain embodiments, the present disclosure provides a method for eliciting an immunological response in a subject comprising administering to the subject a therapeutically effective amount of a vaccine composition as discussed above.

Methods for protecting a subject against ZIKA virus infection is also disclosed. In certain embodiments, the present disclosure provides a method for eliciting an immunological response in a subject comprising administering to the subject a therapeutically effective amount of a vaccine composition as discussed above.

In addition, a method for producing a vaccine composition is provides. In certain embodiments, the method comprises the steps of transforming a plasmid vector into an *agrobacterium* strain, wherein the plasmid vector comprises a backbone of tobacco mosaic virus (TMV) based pIC11599, a first polynucleotide encoding a portion of ZIKA virus envelope protein domain III (zDIII) polypeptide comprising a sequence selected from the group consisting of SEQ ID NO: 1, SEQ ID NO: 7, SEQ ID NO: 8, SEQ ID NO: 9, SEQ ID NO: 10, SEQ ID NO: 11, and SEQ ID NO: 12; and a second polynucleotide encoding HBcAg comprising a sequence of SEQ ID NO: 2 and operatively linked to the first polypeptide; overexpressing the *agrobacterium* strain comprising the plasmid vector in a plant; and extracting and purifying the vaccine composition. In other embodiments, the method for producing a vaccine composition comprises transforming a plasmid vector into an *agrobacterium* strain, wherein the plasmid vector comprises a backbone of tobacco mosaic virus (TMV) based pIC11599, a first polynucleotide encoding a portion of ZIKA virus envelope (E) protein defined by SEQ ID NO: 13 or SEQ ID NO: 14, and a second polynucleotide encoding HBcAg defined by SEQ ID NO: 2 and operatively linked to the first polypeptide; overexpressing the *agrobacterium* strain comprising the plasmid vector in a plant; and extracting and purifying the vaccine composition from the plant. In yet other embodiments, the method for producing a vaccine composition comprises transforming a plasmid vector into an *agrobacterium* strain, wherein the plasmid vector comprises a backbone of tobacco mosaic virus (TMV) based pIC11599 and a polynucleotide encoding a portion ZIKA virus envelope (E) protein defined by SEQ ID NO: 13 or SEQ ID NO: 14; overexpressing the *agrobacterium* strain comprising the plasmid vector in a plant; and extracting and purifying the vaccine composition from the plant.

Once this vaccine formulation solution has been achieved, the formulation may be separated into vials or other suitable containers. The vaccine formulation herein described may then be packaged in individual or multi-dose ampoules, or be subsequently lyophilized (freeze-dried) before packaging in individual or multi-dose ampoules. The vaccine formulation herein contemplated also includes the lyophilized version. The lyophilized vaccine formulation may be stored for extended periods of time without loss of viability at ambient temperatures. The lyophilized vaccine may be reconstituted by the end user, and administered to a patient.

The vaccine of the present disclosure may be either in a solid form or in a liquid form. Preferably, the vaccine of the present disclosure may be in a liquid form. Further, the vaccine of the present technology may be administered by intranasal delivery or intramuscular administration, e.g., needle injection.

Example 1

Material and Methods
Construction of DIII Expression Vectors

The coding DNA sequence of ZIKV E protein of strain PRVABC59 (amino acid 291-723, Genbank Acc. No. AMC13911.1) was synthesized with optimized *N. benthamiana* codons (Integrated DNA Technologies, IA). The coding sequences of zDIII and HBcAg (amino acid 1-155) were amplified by PCR with primer pairs (SEQ ID NO: 3—GTTTCTTACTCTCTTTGC) and (SEQ ID NO. 4—AGGAGCTCTCAAGATCCAAAATCCCAAGC) and with (SEQ ID NO: 5—ACCATGGACATTGACCCTTAC) and (SEQ ID NO. 6—GCAAAGAGAGTAAGAAACACCCCTGTCCCTTCT TCG), respectively. The DNA sequence of zDIII was fused to the 3' of HBcAg sequence by overlapping PCR with primer ACCATGGACATTGACCCTTAC (SEQ ID NO. 5) and AGGAGCTCTCAAGATCCAAAATCCCAAGC (SEQ ID NO. 4). The coding sequence of HBcAg-zDIII fusion protein was then cloned into the TMV-based expression vector pIC11599 of the MagnICON system (MilliporeSigma, MA) (FIG. 1). The coding sequence of HBcAg was also cloned into pIC11599 for producing the HBcAg reference standard.

Expression of HBcAg-zDIII in *N. benthamiana* Leaves

Plant expression vectors were transformed into *A. tumefaciens* GV3101 by electroporation as previously described. *N. benthamiana* plants were grown and co-agroinfiltrated with the GV3101 strain containing the HBcAg-zDIII 3' module (pICH11599-HBcAg-zDIII) or the HBcAg 3' module (pICH11599-HBcAg) along with its 5' TMV module (pICH20999 for ER targeting) and an integrase construct (pICH14011) as described previously. Leuzinger, K. et al. Efficient Agroinfiltration of Plants for High-level Transient Expression of Recombinant Proteins. Journal of Visualized Experiments. doi:10.3791/50521 (2013), Chen, Q. et al. Agroinfiltration as an Effective and Scalable Strategy of Gene Delivery for Production of Pharmaceutical Proteins. Advanced Technology in Biology and Medicine 1, 103-112 (2013), and Chen, Q. In Molecular Vaccines, Vol. 1. (ed. M. Giese) 153-181 (Springer, doi:10.1007/978-3-7091-1419-3_8, Vienna; 2013) are incorporated herein.

Extraction and Purification of HBcAg-zDIII VLP from *N. benthamiana* Leaves

Agroinfiltrated *N. benthamiana* leaves were harvested 5-8 dpi for evaluating HBcAg-zDIII VLP expression. Leaves were harvested 7 dpi for other protein analysis. Leaves were homogenized in extraction buffer (1× saline buffer (PBS), pH 5.2, 1 mM EDTA, 2 mM PMSF (Sigma, Germany) at 1.5 ml/g LFW). The extract was clarified by centrifugation at 15,000×g for 30 min at 4° C. The supernatant was incubated for 12 hr at 4° C., and then spun at 15,000×g for 30 min at 4° C. The supernatant was recovered and pH adjusted to 7.0. The supernatant was then subjected to a sucrose gradient sedimentation as described previously. Briefly, clarified plant extracts (4 ml) were layered onto linear 28 ml 10-70% sucrose gradients dissolved in PBS (pH 7.0). After centrifugation at 175,000×g for 12 h at 4° C., 32 fractions (1 ml each) were collected and assayed for HBcAg and zDIII content, and VLP assembly by ELISA, SDS-PAGE, and electron microscopy. The parent HBcAg VLP was also extracted and purified in parallel with HBcAg-DIII VLP.

SDS-PAGE, Western Blot, and ELISAs

Samples containing HBcAg-zDIII were subjected to 10% SDS-PAGE under a reducing (5% v/v β-mercaptoethanol) condition as described previously. Gels were either stained with Coomassie blue or used to transfer proteins onto PVDF membranes (MilliporeSigma, MA). Membranes were first incubated with either ZV54, a zDIII-specific mouse mAb (a gift from Dr. M. Diamond, Washington University) or an HBcAg-specific mouse mAb (Abcam, MA) to detect the zDIII and HBcAg component of the fusion protein, respectively. Membranes were subsequently incubated with a goat anti-mouse IgG conjugated with horseradish peroxidase (HRP) (Southern Biotech, AL). Specific bindings were detected using an "ECL" Western blot detection system (Thermo Fisher, IL). The purity of HBcAg-zDIII VLP was quantitated using a densitometer to analyze protein bands stained with Coomassie blue on SDS-PAGE as described previously.

The temporal expression pattern of HBcAg-zDIII was examined by ELISA that detected the fusion protein that contains both HBcAg and zDIII components. Briefly, plates were coated with ZV54 mAb and incubated with the plant protein extract. An HRP-conjugated anti-HBcAg mAb (Abcam, MA) was used as the detection antibody. Purified HBcAg was used as a reference standard. The plates were then developed with Tetramethylbenzidine (TMB) substrate and read at 450 nm (KPL Inc, MA).

The specific recognition of HBcAg VLP-displayed zDIII by mAbs that bind to ZIKV DIII-specific conformational epitopes was determined by ELISA as described previously. Purified HBcAg-zDIII VLP was immobilized on microtiter plates and incubated with ZV54, a mAb that only binds a lateral ridge conformational epitope on zDIII. An HRP-conjugated goat anti-mouse-IgG antibody (Southern Biotech, AL) was used to detect bound antibodies. A mAb that recognizes the equivalent epitope on the DIII of WNV (E16) was used as a negative control.

ELISAs were also used to determine the titers of zDIII-specific total IgG and the IgG1 and IgG2a subtypes in mouse serum as previously described. The titers of zDIII-specific total IgG was determined by coating the microtiter plates with zDIII, blocking with PBS with 1% bovine serum albumin (BSA), and incubating with a serial dilution of serum. The plates were then incubated with an HRP-conjugated goat anti-mouse IgG (Southern Biotech, AL), washed with PBS, developed with TMB substrate, and read at 450 nm. For determining the IgG1 and IgG2a subtypes, the same ELISA procedure was performed except HRP-conjugated subtype specific antibodies, i.e. a goat anti-mouse IgG1 (Santa Cruz Biotech, TX) and anti-mouse IgG2a (Santa Cruz Biotech, TX) were used as detection antibodies in place of a goat anti-mouse IgG antibody. All ELISA measurements were repeated at least three times with each sample in triplicate. Endpoint titers were defined as the highest reciprocal serum dilution that yielded an $OD_{450}$ >2-fold over background values. Geometric mean titer (GMT) was calculated for each group at various time points, and was used to express the titers of the zDIII-specific total IgG or IgG subtypes.

Electron Microscopy

Purified HBcAg-zDIII VLPs was subjected to negative staining with 0.5% aqueous uranyl acetate, and transmission electron microscopy was performed with a Philips CM-12S microscope as described previously.

Neutralization Assay

ZIKV-specific neutralizing antibodies were measured with a plaque reduction neutralization test (PRNT) as previously described. Briefly, ZIKV (PRVABC59, ATCC #VR-1843) was diluted in Opti-MEM medium to a working concentration of 100 plaque-forming units (PFU) per well. ZIKV was then added to the two-fold serially diluted serum and incubated for 1 hr at 37° C. Virus/serum mixture was subsequently transferred to 12-well plates containing confluent Vero cells (ATCC #CCL-81) and incubated for 1 hr at 37° C. After removing the virus/serum-containing medium, cells were overlaid with fresh MEM medium containing 5% FBS and 0.8% agarose (Invitrogen, CA), incubated for an additional 3 days at 37° C., fixed in 4% paraformaldehyde (PFA, MilliporeSigma, MA), and then stained with 0.2% crystal violet to visualize plaques. Percent (%) neutralization was calculated as: [(number of ZIKV plaque per well without anti-zDIII serum)−(number of ZIKV plaque per well of diluted anti-zDIII serum)/(number of ZIKV plaque per well without anti-zDIII serum)×100]. Neutralizing antibody titers were expressed as the reciprocal of the highest dilution of serum that neutralized ≥50% of ZIKV. Experiments were repeated at least three times.

Antibody-Dependent Enhancement Assay

Sera from vaccinated mice were pooled and total IgG was isolated using IgG purification kits (GE Healthcare, PA). DENV-2 (ATCC #VR-1584) was mixed with each of eight 3-fold serial dilutions of IgG or an anti-DENV-2 E domain II mAb (4G2) as positive control, respectively. The antibody-DENV-2 mixtures were incubated at 37° C. for one hour before added to FcgRIIA+K562 cells (ATCC #CCL-2243) at an MOI of 1.0. The K562 cells were then incubated at 37° C. with 5% C02 for 48 hr. DENV-2 infected cells were collected, fixed and permeabilized then fluorescently labeled. The percentage of infected cells was determined by flow cytometry as described in Dent et al, 2016.

Mouse Immunization

All animal work was approved by the institutional animal care and use committee and carried out in accordance with its guidelines for the care and use of laboratory animals. Six-week old female C57BL/6 mice were divided into 4 groups (n=6 per group). Mice in group 1 received PBS with aluminum hydroxide gel (alum)+poly I:C (InvivoGen, CA) as mock immunized control. Groups 2, 3, and 4 received 50 μg of HBcAg-zDIII VLP per dosage with poly I:C (InvivoGen, CA), alum, and poly I:C+alum as adjuvant, respectively. On Day 0, each mouse was injected subcutaneously with 100 μl of material containing saline or 50 μg purified HBcAg-zDIII VLP in PBS in the indicated adjuvant. Mice were boosted on days 21 and 42 using the same dosage of antigen as in the 1st immunization but without any adjuvant. Blood samples were collected from the retro-orbital vein on days 14 (2 week), 35 (5 week) and 56 (8 week) after the 1st immunization. Pre-immune serum samples were also collected on Day −7 before the immunization. Mice were euthanized on day 63 (9 week) and the spleens were aseptically removed for in vitro splenocyte cultures.

Cytokine Production Measurement in Spleen Cell Culture

A mechanical dissociation method was used to prepare single-cell suspension of the spleens from immunized mice as published previously. Splenocytes were resuspended to $5\times10^6$ cells/ml in RPMI 1640 medium with 10% heat-inactivated FBS (Invitrogen, CA) and subsequently stimulated with 10 μg/ml of zDIII protein, T cell mitogen Con A (5 μg/ml, MilliporeSigma, MA) (positive control), and RPMI 1640 medium (negative control), respectively. The supernatant of splenocyte cultures was collected 48 hr after stimulation to determine IFN-γ production by using ELISA MAX (Deluxe Set) mouse ELISA kits (BioLegend, CA) as instructed by the manufacturer's protocol. Experiments were performed in triplicates and repeated at least twice independently.

Statistical Analyses GraphPad Prism software version 7.0 (GraphPad, CA) was used to perform the analysis of biochemical and immunological data. Non-linear regression analysis using a one-site binding model was used to determine the Kd of zDIII binding to ZV54. Comparisons of zDIII-specific total IgG, IgG1 and IgG2a titers, cytokine concentrations, and neutralization potency between groups was performed using t-tests. Comparison of total IgG, IgG1/IgG2a ratio between samples collected at various time points was performed by two-way ANOVA. A p value of <0.05 indicated statistically significant differences.

Results

HBcAg-zDIII Expression in N. benthamiana Plants

Figure 2:
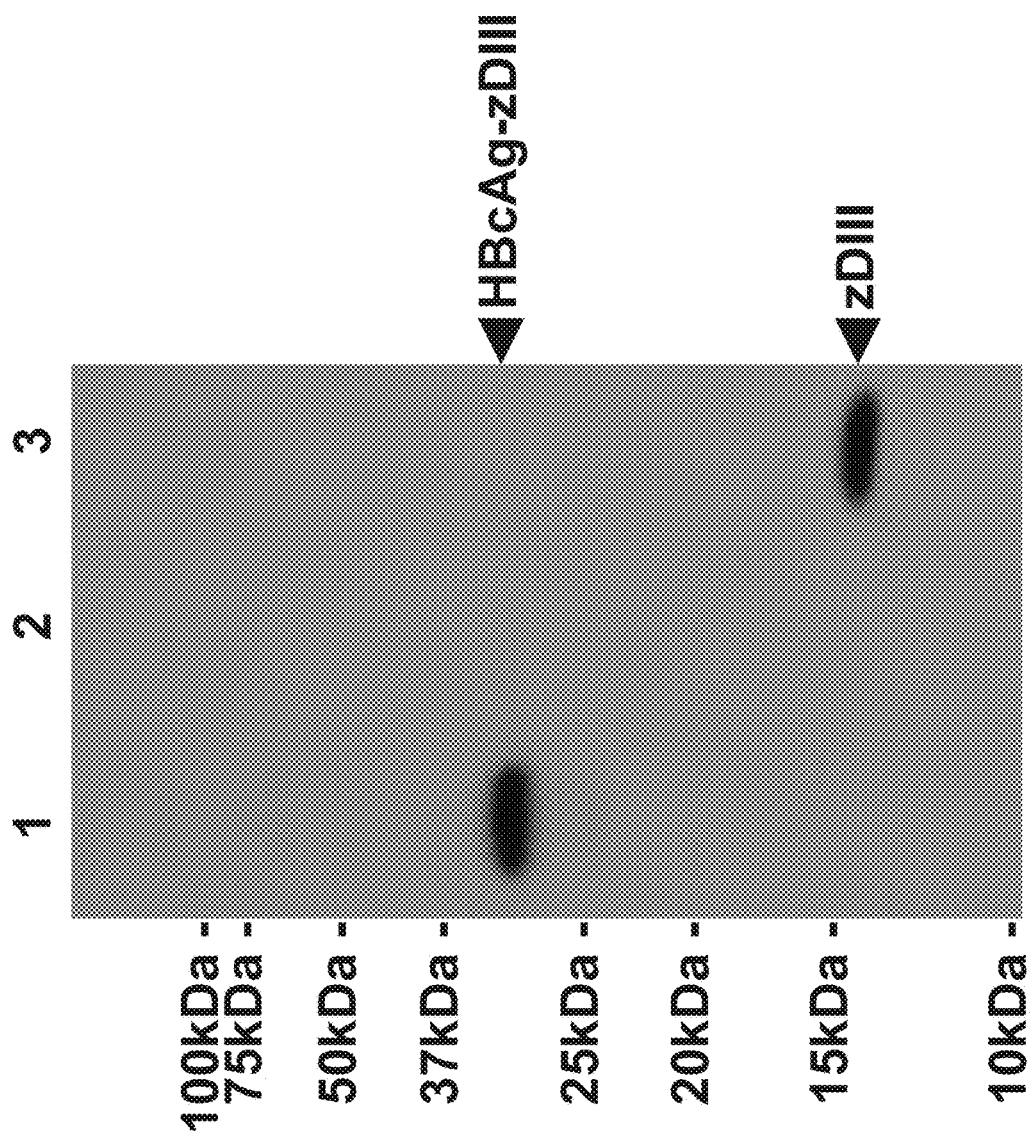
FIG. 2. Western blot analysis of HBcAg-zDIII. Leaf protein extracts were separated on 4-20% SDS-PAGE gradient gels under reducing condition and blotted onto PVDF membranes. The membranes were incubated with a mouse anti-zDIII antibody to detect the HBcAg-zDIII fusion protein. Lane 1, Extract from leaves infiltrated with HBcAg-zDIII construct; lane 2, Extracted from un-infiltrated leaves as a negative control; lane 3, zDIII positive control.
Figure 3:
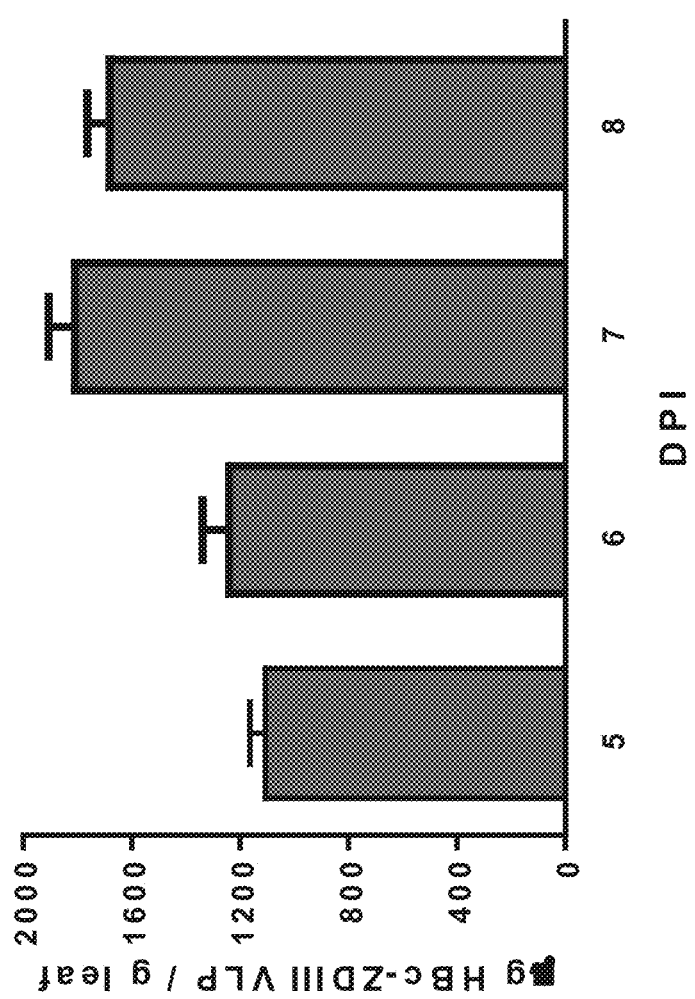
FIG. 3. Temporal accumulation pattern of HBcAg-zDIII in *N. benthamiana* plants. Total proteins from HBcAg-zDIII construct-infiltrated *N. benthamiana* leaves were isolated on days 5 to 8 post agroinfiltration (DPI) and analyzed with an ELISA that detects HBcAg-zDIII. Mean±standard deviation (SD) of samples from three independent infiltration experiments are presented.

The coding sequence of zDIII (amino acid 303 to 433 of E protein) was fused to the 3' of the coding sequence of HBcAg (amino acid 1 to 155) and cloned into a MagnICON-based plant expression vectors (FIG. 1). The A. tumefaciens strain that contains HBcAg-zDIII construct were agroinfiltrated into N. benthamiana leaves. Western blot analysis was performed to evaluate the expression of HBcAg-zDIII. As shown in FIG. 2, a positive band with the predicted molecular weight for HBcAg-zDIII fusion protein (31.7 Kda) was detected with antibodies that specifically recognize zDIII (FIG. 2, Lane 1) or HBcAg zDIII (data not shown), indicating the expression of the fusion protein. The lack of positive band in the negative control leaf samples (FIG. 2, Lane 2) confirmed the specificity of the HBcAg-zDIII band. An ELISA was used to quantify the expression of HBcAg-zDIII, which showed that HBcAg-zDIII reached the highest level of production 7 days post agroinfiltration (DPI), with an average accumulation of 1,824 µg/g leaf fresh weight (LFW) (FIG. 3). This high level of expression is similar to that previously reported for HBcAg VLPs produced in plants, representing one of the highest expression levels of recombinant proteins in plants.

Plant-Expressed HBcAg-zDIII Assembled into VLPs

Figure 4:
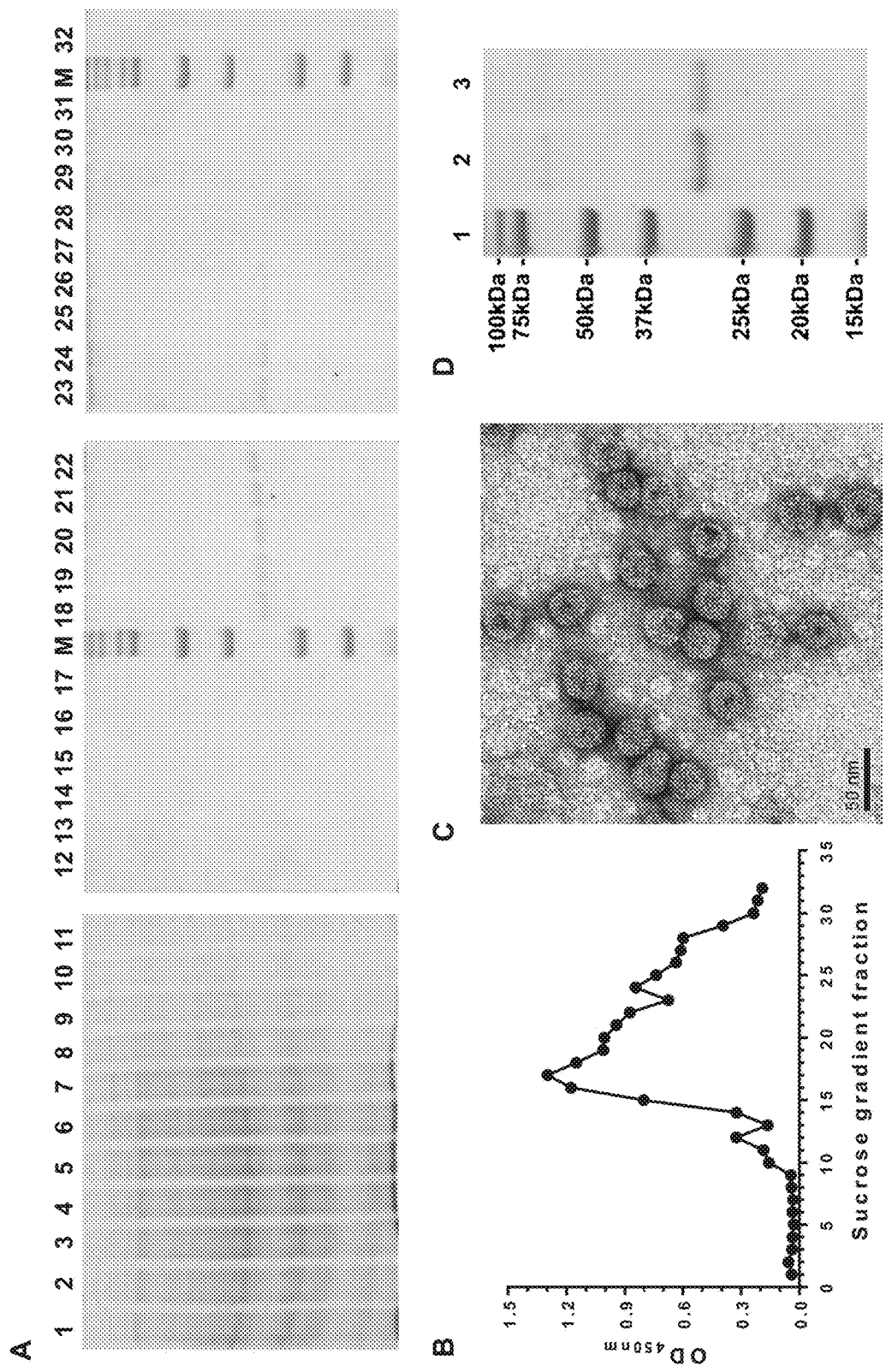
FIG. 4. Characterization of plant-expressed HBcAg-zDIII. HBcAg-zDIII expressing leaf protein extract was subjected to sucrose gradient sedimentation. A: SDS-PAGE analysis of sucrose gradient fractions. Sedimentation is left to right. B: ELISA of sucrose gradient fractions. An anti-HBcAg antibody was used to detect HBcAg. C: Electron microscopy of HBcAg-zDIII from peak fractions of (B) negatively stained with 0.5% uranyl acetate. One representative field is shown. Bar=50 nm. D: SDS-PAGE analysis of HBcAg-zDIII from peak fractions of the sucrose gradient. Lanes 2 and 3: 5 and 2 µg HBcAg-zDIII.
Figure 5:
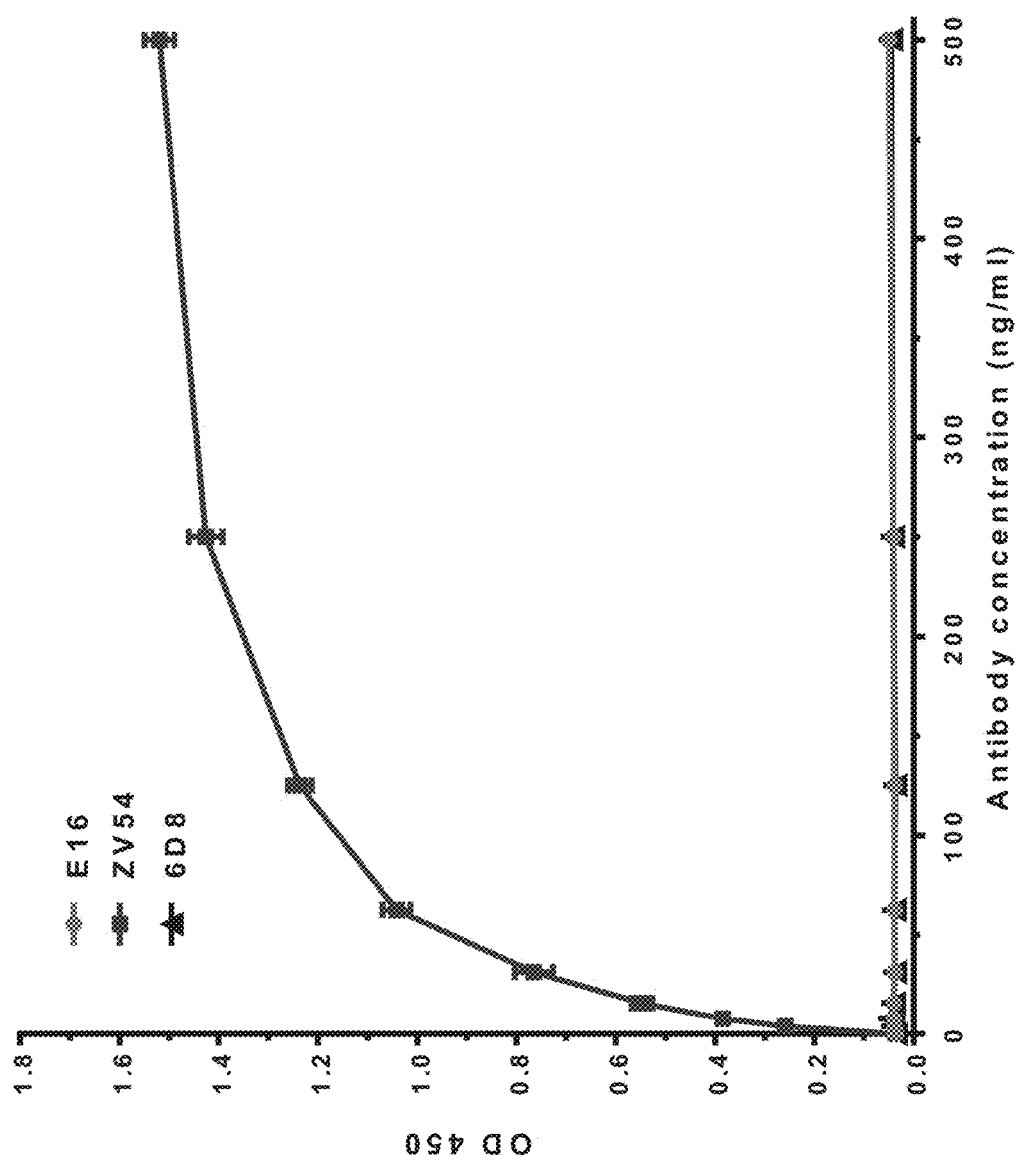
FIG. 5. Specific binding of HBcAg VLP-displayed zDIII by monoclonal antibodies that recognize EDIII conformational epitopes. Serial dilutions of ZV54 and E16 mAbs that recognize a lateral ridge conformational epitope on EDIII of ZIKV and WNV, respectively, were incubated in microtiter wells coated with HBcAg-zDIII VLPs and detected with an HRP-conjugated goat anti-mouse IgG antibody. Mean±SD of samples from three independent experiments is presented.

Clarified plant extracts were subjected to sucrose gradient sedimentation and SDS-PAGE and ELISA analysis of gradient fractions showed that HBcAg-zDIII was detected in the particulate fractions (FIGS. 4A and B). When compared with HBcAg which is known to assemble into VLPs, HBcAg-zDIII was distributed in the same fractions as the parent HBcAg molecule regardless whether anti-HBcAg or anti-zDIII antibodies were used for detection in ELISA (FIG. 4B) or western blotting (data not shown). Examination of the HBcAg-zDIII peak sucrose gradient fractions by electron microscopy conclusively confirmed the presence of typical HBcAg VLPs with a diameter of ~30 nm (FIG. 4C). The availability of an efficient purification scheme is an essential for HBcAg-zDIII VLP to become a viable vaccine candidate. Indeed, the one-step sucrose gradient centrifugation process efficiently removed most plant host proteins (FIG. 4A, Lanes 1-10) and purified HBcAg-zDIII to greater than 95% homogeneity (FIG. 4D).

zDIII displayed by HBcAg-zDIII VLPs retained the proper folding of the native zDIII To confirm the authentic folding of zDIII displayed by the VLPs, the specific recognition of HBcAg-zDIII by two specific mAbs, i.e. ZV54 mAb and E16 mAb, was examined. E16 was generated against WNV DIII and has been shown to be WNV specific and only bind a conformational epitope on the lateral ridge of WNV DIII. In contrast, ZV54 is ZIKV specific and binds a lateral ridge conformational epitope on zDIII that consists of 4 discontinuous structural elements of the native zDIII. Therefore, recognition of a recombinant HBcAg-zDIII VLP by ZV54 will be indicative of the proper folding of its zDIII moiety. Indeed, a specific and high affinity (Kd=0.2 nM) binding of HBcAg-zDIII VLP to ZV54 was demonstrated by ELISA analysis (FIG. 5). In contrast, HBcAg-zDIII VLP did not show any binding to E16 or 6D8, an anti-Ebola IgG isotype control (FIG. 5). Thus, these results indicated that zDIII was displayed on HBcAg-zDIII VLPs in a conformation that resembles the native viral zDIII on the surface of ZIKV, suggesting the preservation of ZIKV neutralization determinants of zDIII.

Figure 6:
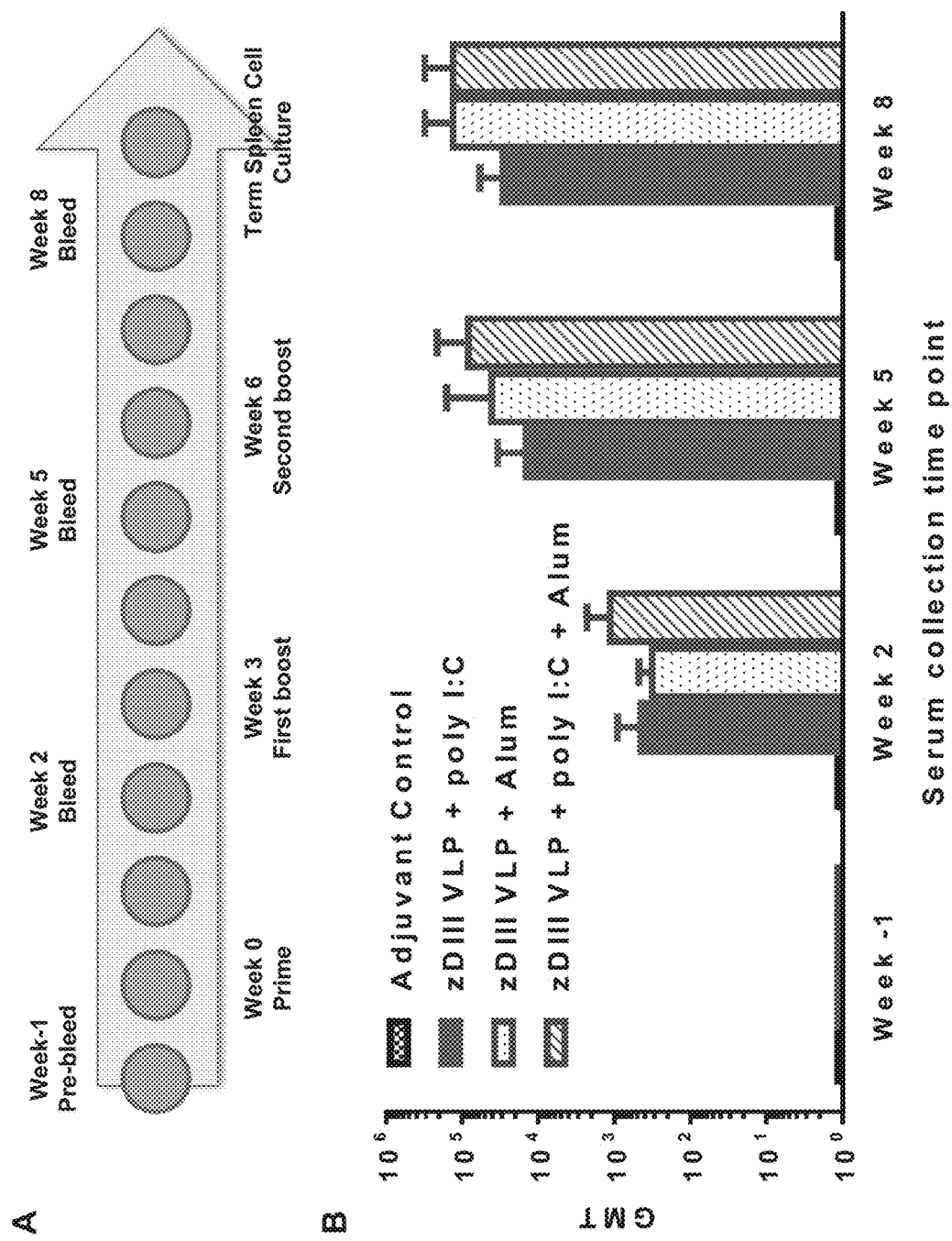
FIG. 6. zDIII-specific IgG responses in mice upon delivery of recombinant HBcAg-zDIII VLPs. C57BL/6 mice (n=6 per group) were immunized subcutaneously with three doses of HBcAg-zDIII VLP over an 8-week time period (A). Antigen was injected on weeks 0, 3, and 6 with 50 µg HBcAg-zDIII. The indicated adjuvant was used in only in the prime injection, but not in the subsequent booster injections. Blood samples were collected on weeks −1 (preimmune bleed), 2, 5, and 8 (2 weeks after each antigen injection) and serum zDIII-specific antibody was measured by ELISA (B). The y axis shows the geometric mean titers (GMT) and the error bars show the 95% level of confidence of the mean.

HBcAg-zDIII VLPs Evoked Potent and Neutralizing Antibody Immune Response in Mice C57BL/6 mice were divided into 4 groups (n=6 per group) and received three doses of 50 µg HBcAg-zDIII VLPs subcutaneously (FIG. 6A). Mice in group 1 (the negative control group) were injected with PBS with poly I:C+alum adjuvant. Groups 2, 3 and 4 were injected with the same amount of HBcAg-zDIII VLP but with different adjuvant of poly I:C (group 2), alum (group 3) or poly I:C+alum (group 4). Adjuvant was only used in the prime injection but not in the subsequent booster injections. zDIII-specific antibody responses from individual mouse were measured and GMT was calculated for each group. The presence of anti-zDIII IgG was not detected in sera from the control adjuvant group throughout the immunization course or in pre-immune serum samples for all groups collected prior to the first immunization (titer <10) (FIG. 6B). The delivery of HBcAg-zDIII VLPs elicited strong zDIII-specific antibody response in all groups after the first administration (week 2, log titers >2.55-3.1) and IgG titers reached its peak at week 5, two weeks after the first boost immunization (log titers >4.2-4.9) (FIG. 6B). Antibody titers at week 8 (two weeks after the second boost) were similar to those of week 5 for all groups that have received HBcAg-zDIII VLPs (p=0.44) (FIG. 6B), suggesting that the last immunization did not significantly further boost the zDIII-specific IgG response. Among different adjuvant groups, the IgG titers in the poly I:C group are lower than that of the alum and poly I:C+alum groups, especially at weeks 5 and 8 (p=0.005 poly I:C compared with alum; p=0.003 poly I:c compared with alum+poly I:C) (FIG. 6B). The amplitude of the zDIII-specific IgG response did not differ significantly between the alum and poly I:C+alum groups throughout the immunization scheme (p=0.87) (FIG. 6B).

Figure 7:
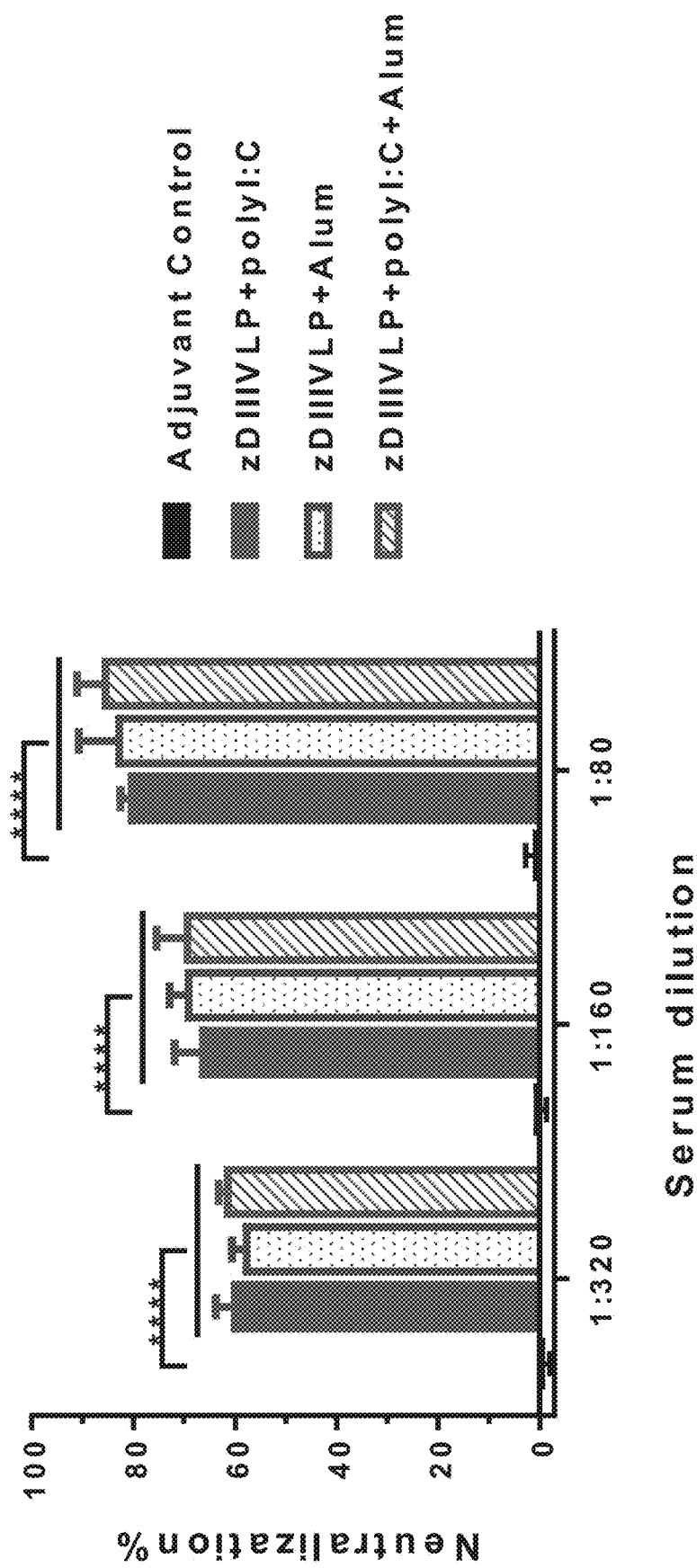
FIG. 7. Neutralization of ZIKV by anti-HBcAg-zDIII serum. Pooled sera from week 5 of mice received PBS+ Adjuvant or 50 µg of HBcAg-zDIII+indicated adjuvant were serially diluted and incubated with 100 PFU of ZIKV prior to infection of Vero cells. A PRNT assay was performed as described in Materials and Methods to assess ZIKV-specific neutralizing antibodies in the sera. Mean neutralization % and SD from three independent experiments with technical triplicates for each sample are presented. **** indicates p values <0.0001 of HBcAg-zDIII-immunized serum compared to that of PBS+adjuvant control, which were determined by 2-way ANOVA.

A plaque reduction neutralization test (PRNT) assay was performed to evaluate the ability of HBcAg-zDIII VLP-induced antibodies in conferring protection against ZIKV infection. As shown in FIG. 7, there was no reduction of ZIKV infection by sera from mice inoculated with PBS+ adjuvant. (FIG. 7). In contrast, anti-HBcAg-zDIII serum (Week 5, for all three adjuvant combinations) conferred potent neutralizing effects against ZIKV infection (p<0.0001 comparing anti-HBcAg-zDIII sera versus adjuvant alone sera) (FIG. 7). For example, greater than 60% and 80% of ZIKV infection was reduced by incubating with sera of 1/320 and 1/80 dilutions from HBcAg-zDIII VLP injected mice, respectively (FIG. 7). No significant difference of neutralization titer was observed for sera among mouse groups received different adjuvants (p=0.42).

HBcAg-zDIII VLPs Also Elicited Potent Cellular Immune Responses in Mice

Figure 8:
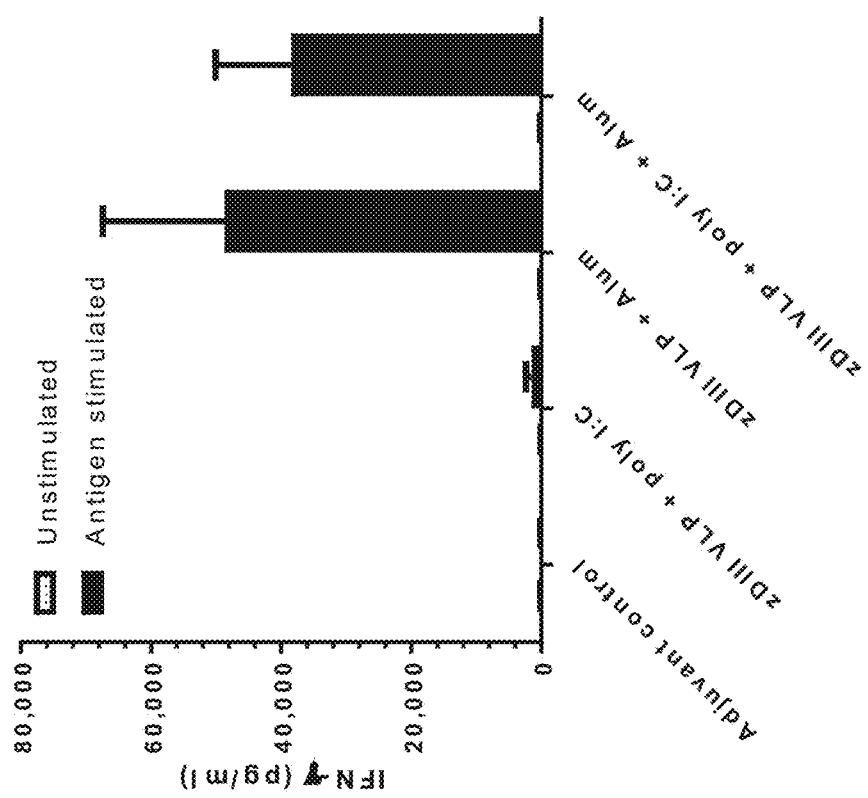
FIG. 8. IFN-γ production by splenocytes from Immunized mice. Spleen cells from mice immunized with PBS+adjuvant or HBcAg-zDIII VLP with indicated adjuvant were stimulated with zDIII for 48 hr. The production of IFN-γ was quantitated by ELISA. Mean concentration (pg/ml) and SD from three independent experiments with technical triplicates are presented.

The ability of HBcAg-zDIII VLPs in inducing cellular immune response was investigated by measuring the production of cytokines by splenocytes from immunized mice after in vitro antigen stimulation. The robust production of cytokines by stimulation with CoA (positive control) indicated the competency of splenocytes in producing cytokines upon stimulation in vitro. Splenocytes of mice receiving PBS+adjuvant did not produce significant IFN-γ titers after in vitro stimulation with zDIII (FIG. 8). In contrast, significant levels of IFN-γ were produced by splenocytes from HBcAg-zDIII-injected mice (FIG. 8). Among the three adjuvant combinations, alum and alum+poly I:C induced strong zDIII-specific cellular immune responses as splenocytes from mice received HBcAg-zDIII VLPs with both of these adjuvant combinations produced similar high levels of IFN-γ (p=0.66), reaching a mean concentration of 48,736 pg/ml (alum adjuvant) and 38,496 pg/ml (alum+poly I:C adjuvant), respectively, 48 hr after re-stimulation. In contrast, splenocytes from mice that received HBcAg-zDIII VLPs with poly I:C as adjuvant produced lower levels of IFN-γ (1,522 pg/ml) (p=0.02 compared to alum or poly I:C+alum as adjuvant). Similar results were also obtained for IL-6 and IL-4 (data not shown). These results demonstrated that HBcAg-zDIII VLPs can induce potent cellular immune responses when appropriate adjuvants are used.

Figure 9:
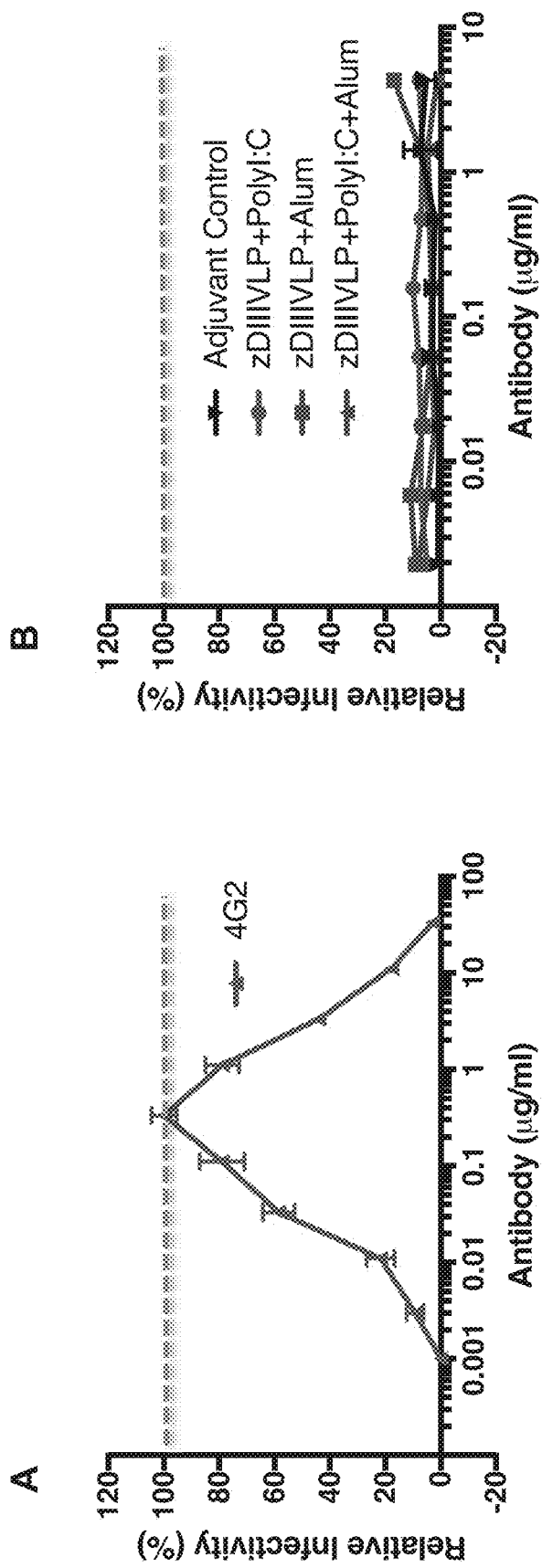
FIG. 9. Lack of enhancement of DENV infection by antibodies in anti-HBcAg-zEDIII serum. IgGs were isolated from week 5 pooled sera of mice received PBS+Adjuvant (adjuvant control) or HBcAg-zDIII+indicated adjuvant. Serial dilutions of IgGs were mixed with DENV-2 and incubated with FcγR expressing K562 cells. Forty-eight hr. later, cells were fixed, permeabilized and analyzed by flow cytometry for DENV infection. Anti-DENV-2 E mAb 4G2 was used as an ADE positive control with its maximum infectivity defined as 100%. Enhancement by IgGs from anti-HBcAg-zEDIII sera is expressed as a % relative to that of the 4G2.

HBcAg-zDIII VLPs Circumvent Induction of Antibodies with ADE Activity for Dengue Virus Infection One of the challenges of vaccine development for ZIKV is the risk of ADE of heterologous flavivirus (e.g. DENV) infection. As such, the inventors investigated if the zDIII-based antigen would avoid or have diminished ability to induce cross-reactive antibodies. Dilutions of IgGs isolated from sera of HBcAg-zDIII VLP-immunized mice were incubated with DENV-2 to evaluate their ability to infect K562 cells that express the human FcγR IIA. IgGs from mice received WNV E protein and 4G2, an anti-DENV-2 E domain II (DII) mAb that cross-reactive with E of other flaviviruses, efficiently promoted ADE of DENV-2 infection of K562 cells (FIG. 9A). In contrast, IgGs isolated from HBcAg-zDIII VLP-injected mice (week 5, all three adjuvant combinations) displayed no significant ADE activity for DENV-2 similar to IgGs from the negative control mice that received PBS and adjuvant (FIG. 9B). To ensure the lack of ADE was not caused by insufficient amount of anti-HBcAg-zDIII VLP IgGs in the assay, PRNT analysis was performed to demonstrate that IgGs at high concentrations used in the assay had neutralizing activity against ZIKV. Thus, our HBcAg-zDIII VLP-based vaccine has a diminished ability to elicit the production of enhancing antibodies against DENV as demonstrated by this in vitro assay.

Discussion

There are challenges that need to be addressed particularly in regards to ZIKA vaccines' safety and cost-effectiveness. For example, risk factors associated with incomplete inactivation of live ZIKV, unfavorable host responses to viral vectors, and the potential of ADE of heterologous flavivirus infection urge the development of safer ZIKV vaccines, particularly for pregnant women. The potential wide-spread epidemics also call for a production platform that can rapidly produce ZIKV vaccines in large-scale and at an affordable cost.

Here, it has been demonstrated for the first time that immunization of recombinant HBcAg-zDIII VLP evoked a potent zDIII-specific response with a ZIKV neutralization titer that is significantly higher than the threshold that correlates with protective immunity in mice against both Brazil (Brazil ZKV 2015) and Puerto Rico (PRVABC59) strains of ZIKV. It has recently been shown that zDIII is the E protein domain that contains epitopes of potently neutralizing antibodies. Zhao, H. et al. Structural Basis of Zika Virus-Specific Antibody Protection. Cell 166, 1016-1027 (2016) is incorporated herein. These anti-zDIII antibodies potently neutralize African, Asian and American strains of ZIKV and many of them protect mice against lethal ZIKV challenges. Importantly, these antibodies are ZIKV specific and, therefore, forego their ability to bind and enhance heterologous flavivirus infection through ADE. These findings and the ability of DIII of flaviviruses to independently fold into a functional domain suggest the promise of zDIII as an appealing vaccine candidate. In this study, the possibility of producing zDIII in the form of a VLP was explored and characterized its immunogenicity and safety in mice. The inventors also tested the ability of plants as a production platform for zDIII VLP-based vaccines aiming to address the scalability and cost issues. HBcAg-zDIII fusion protein was found to produce at very high levels in $N.$ $benthamiana$ leaves 7 days after the infiltration of HBcAg-zDIII construct. HBcAg-zDIII was found to assemble into VLPs by both sucrose gradient centrifugation and electron microscopic analyses. Importantly, zDIII was found to fold properly on the surface of the VLPs as it was specifically recognized by an anti-zDIII mAb that binds a large conformational epitope spanning 4 distinct regions of zDIII. Furthermore, HBcAg-zDIII VLPs can be purified to >95% homogeneity by a simple purification scheme.

The proof-of-principle of inducing protective immunity against ZIKV by vaccination was first demonstrated in mice by immunization with inactivated ZIKV or a plasmid DNA that drives the expression of ZIKV prM-E proteins. This study established that protection of mice against various ZIKV strains including those from Brazil (Brazil ZKV2015) and Puerto Rico (PRVABC59) can be mediated by vaccine-evoked anti-zE IgG alone, and protective efficacy correlate with E-specific antibody titers (log titers >2.35-3.2) and neutralization antibody titers (>10, established against strain PRVABC59). The same ZIKV E-specific IgG-mediated protective mechanism was later confirmed in a rhesus monkey model. Our results reveal that HBcAg-zDIII VLPs also elicited potent zE-specific humoral response, as well as ZIKV-neutralizing antibody response. Specifically, HBcAg-zDIII VLPs induced high antigen-specific IgG titers at week 2 (log titer >2.5-3.1) and week 5 (log titer >4.2-4.9) with all three adjuvant combinations. The HBcAg-zDIII-specific IgG titer (log titer) and ZIKV neutralization titer which was established with the same ZIKV PRVABC59 strain as in previous studies were minimally >4.2 and >320, respectively at week 5, exceeding the threshold of zE-specific and neutralizing antibody titers required for protection against various ZIKV strains in the mouse model. Our results suggest that zDIII-VLPs with poly I:C or alum as adjuvant can be potent in evoking humoral response against ZIKV and may also provide protective immunity in mice.

These results also demonstrate that HBcAg-zDIII VLPs can induce robust cellular responses in mice, indicating the potential of this vaccine for the clearance of ZIKV infection, as well as providing sterilizing immunity. In this study, alum and poly I:C were explored as adjuvant in three formats: alum alone, poly I:C alone, and poly I:C+alum. Alum has been approved as an adjuvant for human applications and poly I:C is a synthetic analog of double-stranded RNA and a ligand of Toll-like receptor 3 (TLR3). It has been shown that TLR3 activation is important for promoting immunity and protection against flavivirus infection. Our results indicate that co-delivery of HBcAg-zDIII VLPs with alum or poly I:C+alum induced significantly higher titers of zDIII-specific antibodies and cytokines than with poly I:C alone, although all three adjuvant combinations evoked ZIKV-neutralizing antibody titers that are higher than that required for protection against multiple ZIKV strains. The ability of HBcAg-zDIII VLPs with alum as adjuvant in inducing strong neutralizing humoral and cellular responses suggests the potential human application of zDIII-based VLP vaccines.

The use of zDIII-VLP based ZIKV vaccines offers several advantages over the published DNA, inactivated virus, adenovirus vector, or mRNA-LNP-based vaccine candidates. First, HBcAg-zDIII VLPs, a protein-based vaccine, will have the best safety profile compared with other vaccine platforms due to the virtual nonexistence of possible incomplete inactivation, oncogenesis by genome insertion, or unfavorable host responses to viral vectors. Additionally, the inventors carefully chose zDIII as the antigen to target well-defined neutralizing epitopes but avoid epitopes with pathological effects. This measure is particularly crucial for vaccine development against ZIKV and other flaviviruses due to the risk of ADE. For example, individuals who were infected or vaccinated against one serotype of DENV are at a higher risk of developing dengue hemorrhagic fever/dengue shock syndrome (DHF/DSS) when they are later exposed to another serotype of DENV. This enhancement of disease severity is most likely caused by ADE because many antibodies generated against the first DENV serotype are cross-reactive but sub-neutralizing against the second serotype of DENV. As a result, the new serotype forms complexes with these antibodies that bind to FcγR-bearing myeloid cells, promoting viral uptake and infection. Due to their common mosquito vectors and geographical distributions, ZIKV and DENV will continue to co-circulate in many areas of the world. Importantly, antibodies against DENV and ZIKV have been found to enhance the replication of each other in vitro, strongly indicating ADE may occur between these two closely-related viral diseases. As such, minimizing the ADE risk of heterologous flavivirus infection should be an important consideration for ZIKV vaccine development. Recent studies reveal that the fusion loop and the adjacent region of ZIKV EDII (zDII) contain the majority of the exposed residues conserved between ZIKV and other flavivirus E proteins. Correspondingly, the majority of DENV cross-reactive but subneutralizing antibodies in human humoral response to ZIKV E protein are targeted to epitopes on zEDII or domain I (zEDI), which is consistent with the findings in other flaviviruses. In contrast, antibodies against zDIII epitopes are overall ZIKV-specific, have potent neutralizing activity, and are protective against ZIKV challenge in mice. Notably, zDIII-specific antibodies did not show ADE activity for DENV infection while zEDI/zEDII-specific antibodies enhanced DENV infection both in vitro and in vivo. Excitingly, our results directly demonstrated that antibodies elicited by zDIII VLPs did not enhance DENV infection. These results indicate that the current zDIII-based vaccine may provide additional safety advantages over other candidates based on inactivated virus, DNA, or adenovirus vector, which all contain zDI/zDII and can potentially induce zDI/zDII-targeted subneutralizing antibodies and enhance DENV infection in vaccinated subjects. This safety issue is particularly important for ZIKV vaccines as pregnant women are the target population.

While the potential issue of pre-existing immunity against hepatitis B virus may render HBcAg-displayed vaccines less effective in exposed populations, this challenge can be addressed by using BcAg derived from nonhuman hepadnaviruses. For example, several core VLPs derived from the rodent hepadnaviruses have been found as immunogenic as the human-derived HBcAg VLPs but are not burdened by the problem of pre-existing immunity or immune tolerance to a human pathogen. Our results indicate that zDIII was displayed on the surface of HBcAg VLPs with a conformation similar to that on its native virus. Moreover, HBcAg-zDIII VLPs are indeed highly immunogenic and induced strong humoral and cellular immune responses specific to zDIII antigen.

The successful production of HBcAg-zDIII VLPs in plants also helps to address the economic issues of vaccines. Since the production of plant biomass and plant-derived proteins can be scaled-up without high-capital investments of cell-culture facilities or bioreactors and expensive tissue culture media, the cost of plant-produced biologics can be greatly reduced. Indeed, recent case studies have confirmed the long-held belief that plant-produced biologics is more cost effective than traditional platforms. For example, it was shown that plant-based platforms can substantially reduce the upstream production cost of biologics to as low as $1.00-2.00 per kilogram of protein. Our results showed that HBcAg-zDIII VLPs were accumulated rapidly at a high level of ~1.8 mg/g LFW in *N. benthamiana* leaves, which is considered more than sufficient for vaccine manufacturing. This expression level at a laboratory condition can be further increased by process optimization of plant growth conditions. The level of HBcAg-zDIII was found to assemble into VLPs by both sucrose gradient centrifugation and electron microscopic analyses. Plant-produced HBcAg-zDIII VLPs were readily extracted and purified from leaves with a two-step purification process, which has been shown to be compliant to current Good Manufacturing Practice (cGMP) regulations and are broadly used for the production of VLP-based vaccines. Thus, the quick and high-level accumulation of HBcAg-zDIII VLPs and their facile purification indicates the potential of plants as a feasible platform for producing HBcAg-zDIII VLPs and other subunit vaccines with favorable cost and scalability. Thus, production of ZIKV vaccines in plants will markedly enhance cost-efficiency so that it is economically feasible to produce them for the developing world, where the majority of ZIKV cases exists.

In summary, the robust production of HBcAg-zDIII VLP has been demonstrated, its effective display of zDIII antigen and facile purification, its potent immunogenicity that correlates with protective immunity against ZIKV, and the lack of ADE for DENV infection. To our knowledge, this is the first report of protein-based VLP ZIKV vaccine that induces neutralizing immunity but circumvents induction of antibodies with ADE activity for DENV infection. Together, our study has provided the proof of principle and suggested the feasibility for the further development of recombinant protein-based subunit vaccines against ZIKV with potency, affordability, and potentially enhanced safety.

Example 2

Experimental Procedures
Construction of zE Expression Vectors
Zika virus E protein DNA coding sequence (SEQ ID NO: 15—ATTAGGTGTATTGGAGTTTCTAATAGAGAT-
TTTGTGGAAGGAATGTCTGGAGGAACT TGGGTT-
GATGTTGTTCTTGAACATGGAGGATGTGTTACTGT-
TATGGCTCAAGATAAG
CCAACTGTTGATATTGAGCTTGTTACTAC-
TACTGTTTCTAACATGGCTGAGGTTAGGT
CTTACTGTTATGAGGCTTCTATTTCTGA-
CATGGCTTCTGATTCAAGGTGTCCAACTCA
GGGAGAGGCTTATCTTGATAAGCAGTCTGATACT-
CAATATGTTTGTAAGAGAACTCT TGTTGATAGAG-
GATGGGGAAACGGATGTGGACTTTCGGAAAGG-
GATCTCTTGTGA CTTGTGCTAAGTTCGCTTGTTCTAAGAAGATGACTGGAAAGTCTATTCAGCCAGAAA ATCTTGAGTATAGAATTATGCTTTCTGTTCACGGATCTCAACATTCTGGAATGATTGT TAACGATACTGGACACGAAACTGACGAGAATAGAGCTAAGGTTGAAATTACTCCAA ATTCTCCAAGAGCTGAAGCTACTCTTGGAGGATTTGGATCTCTTGGACTTGATTGTG AGCCAAGAACTGGACTTGATTTTTCTGATCTTTATTATCTTACTATGAACAACAAAC ATTGGCTTGTTCATAAGGAATGGTTTCATGATATTCCACTTCCTTGGCATGCTGGAGC TGATACTGAACTCCACATTGGAACAACAAGGAAGCTCTTGTTGAGTTCAAGGATGC TCATGCTAAGAGACAAACTGTTGTTGTTCTTGGATCTCAAGAAGGAGCTGTTCATAC TGCTCTTGCTGGTGCTCTTGAAGCTGAGATGGATGGAGCTAAGGGAAGGCTTTCTTC TGGACACCTTAAGTGCAGACTTAAGATGGACAAACTTAGACTTAAGGGAGTTTCTTA CTCTCTTTGCACTGCTGCTTTCACTTTTACTAAGATTCCAGCTGAAACTCTTCATGGA ACTGTGACTGTGGAAGTTCAATATGCTGGAACTGATGGAC CATGTAAGGTTCCAGCT CAAATGGCTGTGGATATGCAGACTCTTACTCCAGTTGGAAGGCTTATTACTGCTAAC CCAGTTATTACTGAGTCTACTGAAAACTCTAAGATGATGCTTGAGCTTGATCCACCA TTCGGAGATTCTTACATTGTTATTGGAGTTGGAGAAAAGAAGATTACTCATCATTGG CATAGGTCTGGATCTACTATTGGAAAGGCTTTTGAAGCTACTGTTAGAGGAGCTAAG AGAATGGCTGTTCTTGGAGATACTGCTTGGGATTTTGGATCT) was synthesized (Integrated DNA Technologies, Coralville, Iowa) using the sequence from strain PRV-ABC59 (am liporeSigma, MA). Mem-branes were incubated with His-Detector™ Ni-HRP conjugate, and specific binding to the PzE-His6 fusion protein was detected using the LumiGLO HRP Chemiluminescent Substrate (KPL Inc, Milford, Mass.). The purity of PzE was quantitated by scanning SDS-PAGE gels with a Bio-Rad ChemiDoc Imager and analysing the band intensity using Quantity One software (Bio-Rad, Hercules, Calif.) as described previously.

The time course of PzE accumulation pattern was examined by an ELISA. Briefly, plates were coated with the plant protein extract and an anti-zE mAb (from Dr. M. Diamond, Washington University Medical School) was used as the primary detection antibody. The plates were then incubated with a HRP-conjugated goat anti-mouse secondary antibody (Southern Biotech, Bermingham, Ala.), developed with tetramethylbenzidine (TMB) substrate, and read at 450 nm (KPL Inc, MA). Purified zE was used as a reference standard.

Figure 10:
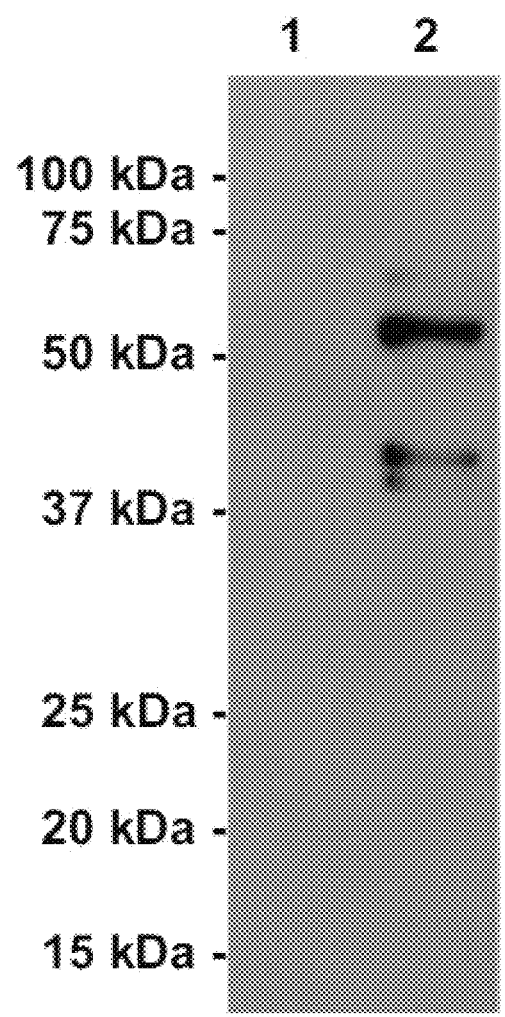
FIG. 10. Western blot analysis of plant-produced zE. Total soluble protein was extracted from leaves and separated on 12% SDS-PAGE gels under reducing condition. Proteins were then blotted onto PVDF membranes. PzE-His6 was detected by incubating the membrane with HisDetector™ Ni-HRP conjugate. Lane 1: extract from uninfiltrated leaves as a negative control; Lane 2: extracted from leaves agroinfiltrated with zE construct.

To evaluate the conformational folding of PzE, an ELISA was performed with mAbs that recognize conformational epitopes on various domains of zE as described previously. PzE purified from plant extracts was immobilized on microtitre plates and incubated with ZV1 and ZV54, mAbs that have been shown to specifically bind conformational epitopes on zEDII and zEDIII, respectively, followed by an HRP-conjugated goat anti-mouse-IgG antibody (Southern Biotech). E16, a WNV EDIII-specific mAb that recognizes the equivalent epitope of ZV54 was used as a negative control.

The inventors also used ELISAs to determine the titres of zE and zEDIII-specific antibodies in mouse serum as previously described. A serial dilution of serum from immunized mice was incubated with PzE immobilized on microtitre plates. The plates were then incubated with an HRP-conjugated goat anti-mouse IgG antibody (Southern Biotech) and developed with TMB substrate. For anti-zEDIII titres, zEDIII was coated on microtitre plates in place of PzE. The highest reciprocal serum dilution that yielded an OD450 >2-fold over background was defined as the endpoint titre. GMT was used to express the endpoint titres of the zE- and zEDIII-specific total IgG.

As C57BL/6 mice express the IgG2c subtype instead of IgG2a, the IgG1 and IgG2c subtype levels were determined in zE-specific IgGs from mouse sera. In place of an anti-mouse total IgG antibody, IgG subtype-specific anti-bodies, that is an HRP-conjugated goat anti-mouse IgG1 or anti-mouse IgG2c (Abcam, Cambridge, Mass.), were used as the detection antibody. Experiments were repeated at least three times independently with each sample in triplicate for all ELISA measurements.

Neutralization Assay

A PRNT assay was performed as previously described to measure the potency of ZIKV-specific neutralizing antibodies in mouse sera. Briefly, ZIKV (PRVABC59, ATCC #VR-1843) was added to twofold serially diluted mouse sera at a concentration of 100 plaque-forming units (PFU) per well. Virus/serum mixture was incubated at 37° C. for 1 h before transferred to 12-well plates containing a confluent monolayer of Vero cells (ATCC #CCL-81). After incubation for 1 h at 37° C., the virus/serum-containing medium was removed and cells were overlaid with fresh MEM medium containing 5% FBS and 0.8% agarose (Invitrogen, Carlsbad, Calif.) and incubated for an additional 3 days at 37° C. On day 4, infected VERO cells were fixed in 4% paraformaldehyde (PFA; MilliporeSigma, MA) and then stained with 0.2% crystal violet to visualize ZIKV plaques. Percent (%) neutralization was calculated as: [(number of ZIKV plaque per well without anti-zE serum)−(number of ZIKV plaque per well of diluted anti-zE serum)/(number of ZIKV plaque per well without anti-zE serum)×100]. Neutralizing antibody titers were expressed as the reciprocal of the highest dilution of serum that neutralized 50% of ZIKV. Experiments were repeated at least three times independently.

Mouse Immunization

All animal work was performed in accordance with the guidelines of National Institutes of Health (NIH) for the care and use of laboratory animals and approved by the institutional animal care and use committee of Arizona State University. Female C57BL/6 mice (Jackson Lab, Bar harbor, ME) at 6 weeks old were divided into two groups (n=6 per group). Mice in group 1 each received 100 lL PBS with aluminium hydroxide gel (alum; InvivoGen, San Diego, Calif.) as mock immunized control. Each mouse in group 2 received 50 lg of PzE per dosage in PBS with alum as adjuvant. Mice were first immunized on day 0 and boosted on days 21 and 42 with the same dosage but without any adjuvant. Blood samples were collected from the retro-orbital vein at three time points (days 14, 35 and 56) after the first immunization. Blood samples were also collected on day 7 (week −1) before the first immunization. Mice were euthanized on day 63 (week 9), final blood samples were collected, and spleens were aseptically removed for in vitro splenocyte cultures. This immunization scheme has been shown to be effective for flavivirus vaccine development and aimed to provide data that would be comparable in antigen delivery or sample collection intervals to available results from other ZIKV vaccine candidates at the time of the experiment design.

Spleen Cell Culture and Cytokine Production

The inventors used a previously published mechanical dissociation method to prepare single-cell suspension of the spleens from immunized mice. Cultures of splenocytes at 5 9 106 cells/mL were stimulated with 10 μg/mL of PzE. T cell mitogen Con A (5 μg/mL, MilliporeSigma, MA) and culture medium were used as the positive and negative controls, respectively, to stimulate the splenocyte. The supernatant from splenocyte cultures was collected 48 h after stimulation, and aliquots were stored at −80° C. Cytokine analysis was performed using mouse IFN-c, IL-6 and IL-4 ELISA Deluxe Set kits (BioLegend, San Diego, Calif.) following the manufacturer's protocol. Each cytokine was measured in triplicate with two independent experiments.

Statistical Analyses

All biochemical and immunological data were analyzed by GraphPad Prism version 7.0 (GraphPad, La Jolla, Calif.). Two-way ANOVA was used to compare zE- and zEDIII-specific IgG titers, cytokine concentrations, and neutralization potency between groups or between samples collected at various time points. A P value of less than 0.05 or lower indicated statistically significant differences.

Results

Expression of Zika virus envelop protein in *Nicotiana benthamiana* plants

The coding sequence of zE was fused to that of hexahistidine tags (His6) and cloned into a MagnICON-based plant expression vector. zE was then transiently expressed in *N. benthamiana* plants by infiltrating the zE-His6 construct-containing *Agrobacterium tumefaciens* strain into leaves. Western blot analysis detected a positive band with the expected molecular weight of the zE-His6 protein (52.7 Kda) in the sample from zE-His6 construct-infiltrated leaves (FIG. 10, Lane 2), while no positive signal was detected in the negative control leaf sample (FIG. 10, Lane 1), indicating the specificity of the zE band and confirming the expression of the target protein. A smaller cross-reactive band was also detected below the full-length E protein (FIG. 10, Lane 2), suggestive of a potential degradation product or a truncated zE protein. An ELISA was used to monitor the temporal expression pattern of zE in leaves, which revealed that zE was produced rapidly and accumulated to the peak level of >160 lg per gram of leaf fresh weight (LFW) 6 days postagroinfiltration (DPI) (FIG. 11).

Purification of zE from *Nicotiana benthamiana* Leaves

Figure 12:
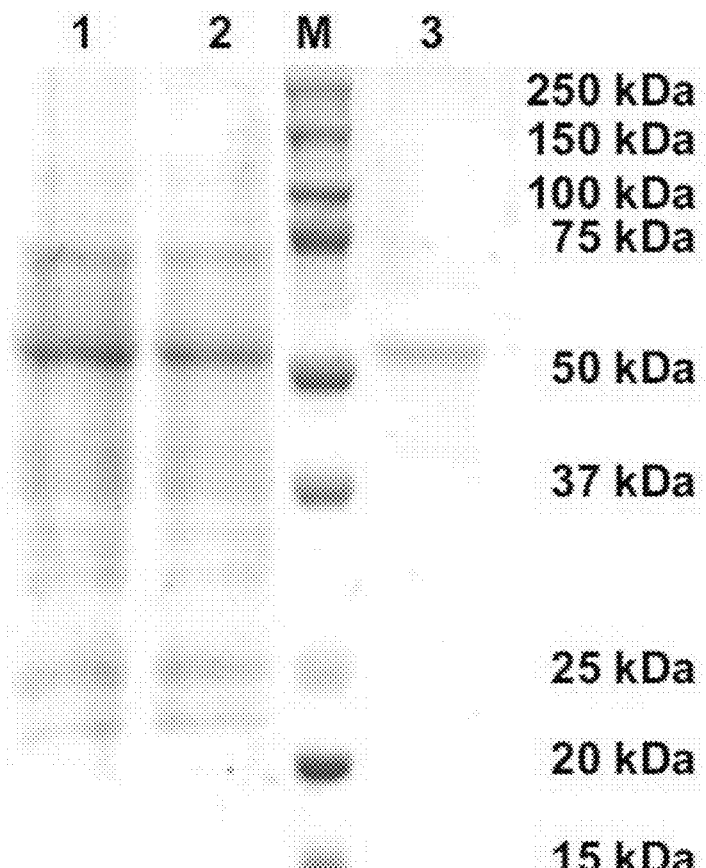
FIG. 12. Purification of PzE from *Nicotiana benthamiana* plants. Total leaf protein was extracted from *N. benthamiana* leaves, and PzE was purified by $Ni^{2+}$ immobilized metal anion chromatography (IMAC). Chromatographic fractions were analysed on 12% SDS-PAGE gels and visualized with Coomassie blue staining. Lane 1: total leaf protein loaded on $Ni^{2+}$ IMAC columns; Lane 2: $Ni^{2+}$ IMAC flow through; Lane 3: $Ni^{2+}$ IMAC elute; M: protein molecular weight marker. All lanes are from the same gel with irrelevant lanes removed.

To demonstrate that plant-produced zE (PzE) has the potential to become a viable vaccine, an effective purification procedure was developed to recover PzE from leaves. This is a one-step scheme in which clarified plant extract is subjected to Ni2+-based immobilized metal anion chromatography (IMAC) as zE was tagged with His6 tags. SDS-PAGE analysis indicates that Ni2+ affinity chromatography was effective in removing *N. benthamiana* host proteins and was able to enrich PzE to >90% purity (FIG. 12).

Figure 13:
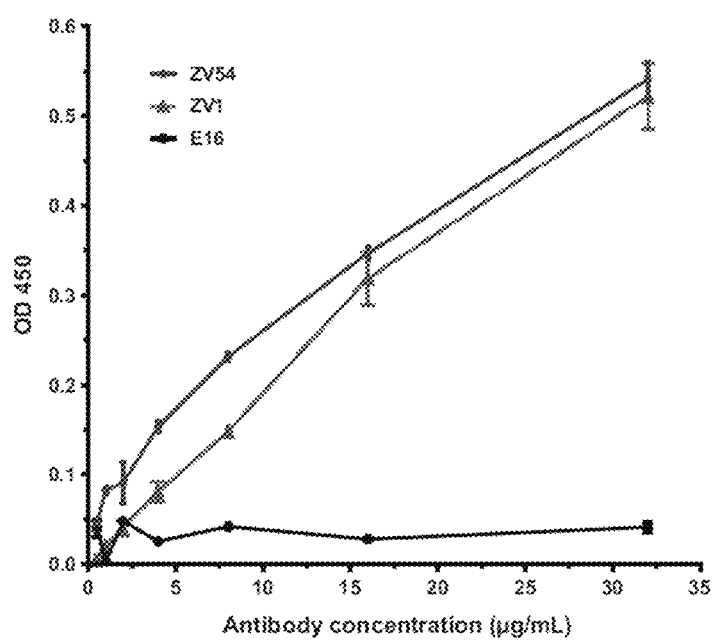
FIG. 13. Specific binding of PzE by monoclonal antibodies that recognize zE conformational epitopes. PzE was coated in microtiter plates and incubated with serial dilutions of ZV1 or ZV54 mAb. E16, a West Nile virus EDIII-specific mAb was used as a negative control. The specific binding between various mAb and PzE was detected by an HRP-conjugated goat anti-mouse IgG antibody. Mean±SD of samples from three independent experiments is presented.

Specific Binding of Plant-Produced zE by Antibodies that Recognize zE Conformational Epitopes The proper folding of PzE was investigated by examining its specific recognition by monoclonal antibodies (mAbs) that target zE conformational epitopes. ELISA results showed that PzE was specifically recognized by ZV1 and ZV54, mAbs that recognize conformational epitopes on ZIKV EDII (zEDII) and EDIII (zEDIII), respectively (FIG. 13). In contrast, no specific recognition was detected between PzE and E16, a mAb that has been shown to be WNV specific and only binds a conformational epitope in the lateral ridge of WNV EDIII. This indicates the preservation of the folding conformation in/near the fusion loop of zEDII and the lateral ridge of zEDIII that are targeted by ZV1 and ZV54, respectively, and suggest the overall proper folding of PzE.

Plant-Produced zE Induced Potent Antibody Immune Response in C57BL/6 Mice

Figure 14:
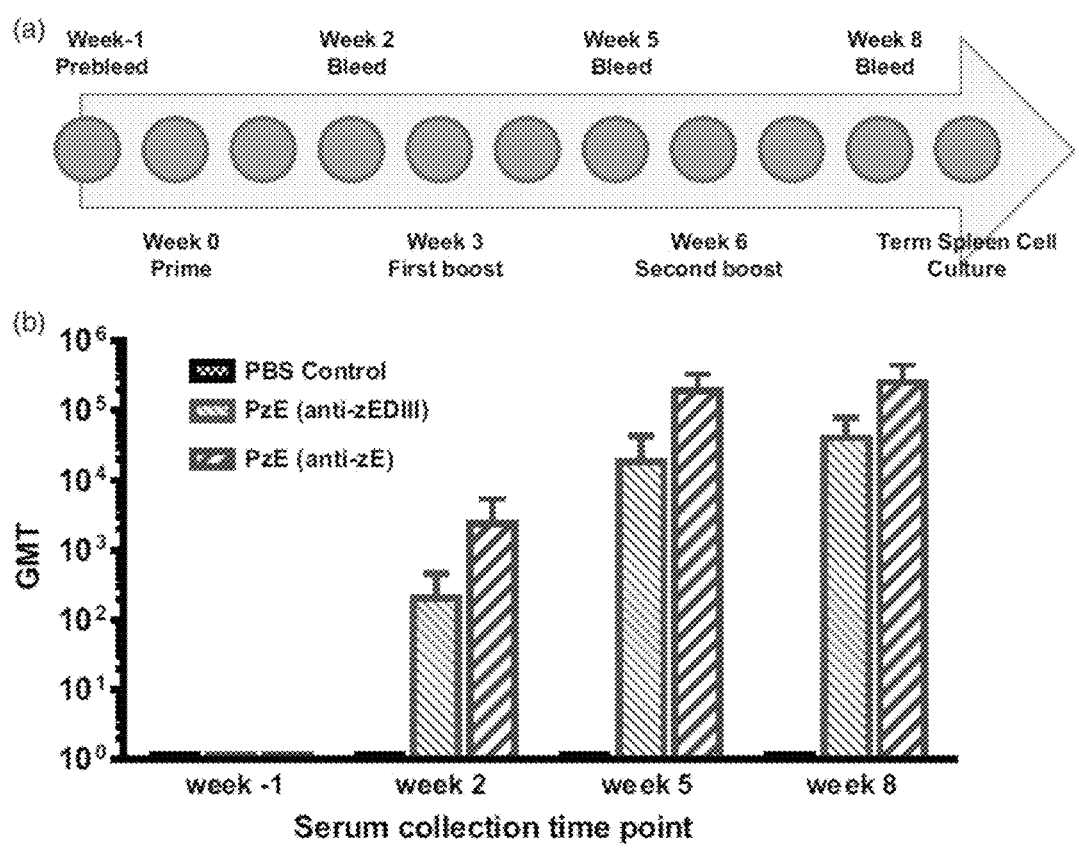
FIG. 14. Antigen-specific antibody responses in PzE-immunized mice. C57BL/6 mice were inoculated subcutaneously with three doses of PzE or PBS (on weeks 0, 3 and 6) over an 8-week period (a). The adjuvant alum was used only in the prime injection. Blood samples were collected on week −1 (pre-immune bleed), 2, 5, and 8 (2 weeks after each antigen injection) and serum zE-specific (anti-zE) and zEDIII-specific (anti-zEDIII) antibody titers were measured by ELISA (b). The y-axis shows the geometric mean titers, and the error bars show the 95% level of confidence of the mean.

To test the immunogenicity of PzE, C57BL/6 mice were inoculated three times at 3-week intervals with 50 μg PzE and alum as an adjuvant via subcutaneous injection (FIG. 14a). Adjuvant was only used in the prime injection but not in the subsequent booster injections. Mice were phlebotomized 1 week prior to the first immunization (week −1, pre-immune sample) and 2 weeks after each immunization (week 2, 5 and 8 samples) (FIG. 14a). In the negative control group, animals received saline buffer (PBS)+alum in the first injection and PBS only in the subsequent injections. Anti-zE and anti-zEDIII antibody titers were measured for each individual mouse, and geometric mean titers (GMT) were calculated for the PzE-immunized and the negative control group. As expected, the presence of anti-zE or anti-zEDIII IgG was not detected in sera from the PBS control group throughout the immunization course or in pre-immune serum samples (titer <10) (FIG. 14b). The injection of PzE, however, evoked a potent antigen-specific antibody response after the first inoculation (week 2, anti-zE log titer >3.4; anti-zEDIII log titer >2.3)(P<0.003 compared with PBS control) and IgG titer peaked at week 5 after boosting (anti-zE log titer log titer >5.3; anti-zEDIII log titer >4.3) (P<0.0001 compared with PBS control) (FIG. 14b). Antibody titers at week 8 after the second boost injection were higher than that of week 5 (anti-zE log titer log titer >5.4; anti-zEDIII log titer >4.6), but without statistical significance (P >0.06) (FIG. 14b). IgG titers against the full-length zE are higher throughout the immunization course than that of against the subdomain zEDIII (P<0.0033).

Figure 15:
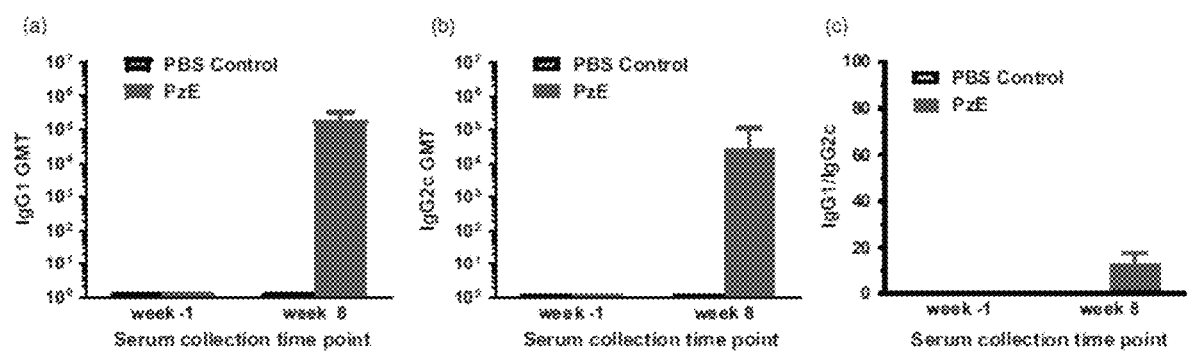
FIG. 15. Anti-zE IgG subtypes induced by immunization of PzE. Sera were collected at week −1 and 8 from PBS or PzE-injected mice, and analyzed by ELISA for zE-specific IgG1 (a) and IgG2c (b) titers. Results (Geometric mean titres and 95% level of confidence of the mean) from three independent measurements are presented for mice in each immunization group. The ratio of zE-specific IgG1 and IgG2c titres was calculated for each individual mouse. The mean IgG1/IgG2c ratio and SD from three independent measurements are presented for each treatment group (c).

To evaluate the type of immune response elicited by PzE, antigen-specific IgG1 and IgG2c subtypes were measured. ELISA results showed that PzE elicited robust response of both IgG1 (FIG. 15a) and IgG2c (FIG. 15b) subtypes with higher titers of IgG1 at week 8 (FIG. 14c). Analysis of serum samples from week 5 also yielded similar results (data not shown) with no significant difference in the ratio of IgG1/IgG2c between weeks 5 and 8 (P >0.05). These results indicate that PzE induced a mixed Th1/Th2 immune response with a Th2-type bias.

Plant-Derived zE Also Elicited Potent Cellular Immune Responses

Figure 16:
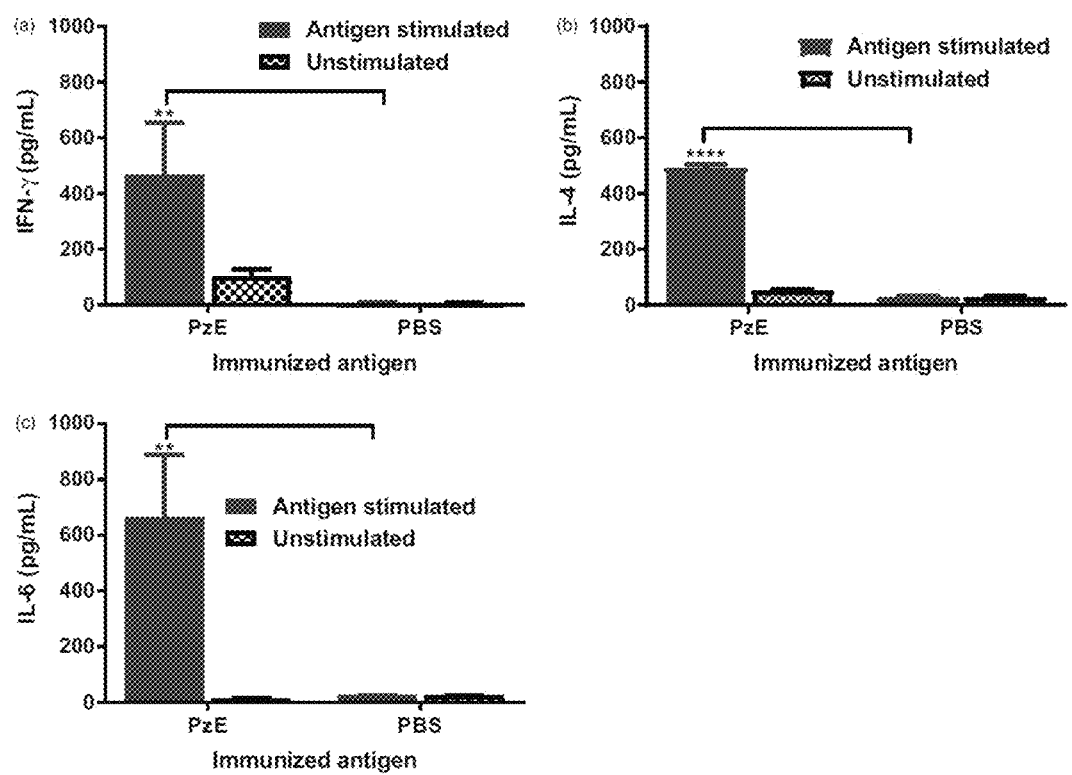
FIG. 16. Production of cytokines by splenocytes from Immunized mice. Spleen cells from mice inoculated with PBS or PzE were stimulated with PzE for 48 h. The production of IFN-c (a), IL-4 (b) and IL-6 (c) was quantitated by ELISA. Mean concentration (pg/mL) and SD from two independent experiments with technical triplicates are presented. ** and  indicate P values <0.0001 and <0.0031, respectively.

The production of cytokines by splenocytes from immunized mice was measured after in vitro antigen stimulation to determine whether PzE can also induce a cellular immune response. The competency of splenocytes in producing cytokines was demonstrated by the detection of high levels of IFN-c, IL-4 and IL-6 upon stimulation with the positive control, ConA (data not shown). As expected, splenocytes of mice receiving PBS did not produce significant titers of cytokines after in vitro stimulation with PzE (FIG. 16). However, splenocytes from PzE-inoculated mice secreted significant levels of IFN-c (FIG. 16a), IL-4 (FIG. 16b) and IL-6 (FIG. 16c). The mean concentrations of IFN-c, IL-4 and IL-6 are similar with each other (P=0.67). These results demonstrated that PzE evoked a potent and mixed Th1/Th2 cellular immune response.

Figure 17:
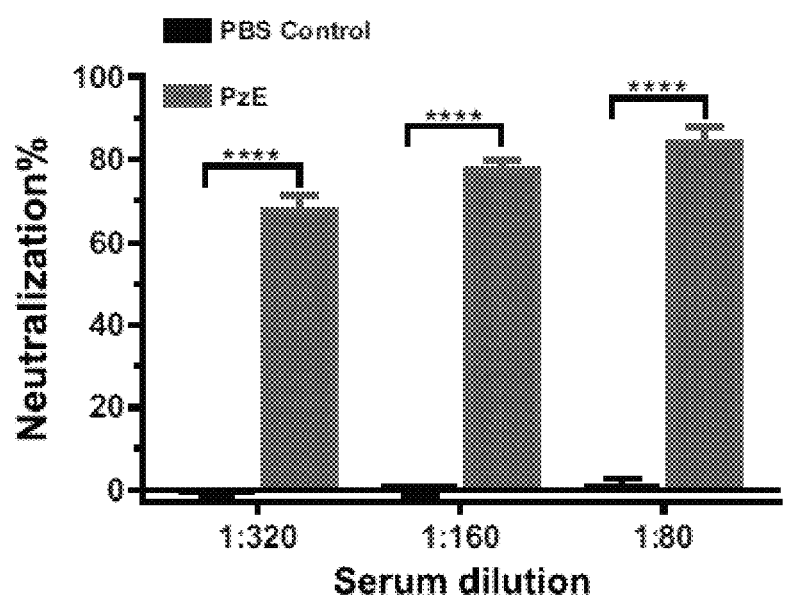
FIG. 17. Neutralization of Zika virus (ZIKV) by anti-PzE serum. Week 5 serum samples from mice received PBS control or PzE were pooled, serially diluted and incubated with ZIKV. The virus/sera mixture was then used to infect Vero cells in a PRNT assay to titer ZIKV-specific neutralizing antibodies in the sera. Mean neutralization % and SD from three independent experiments with technical triplicates for each sample are presented. **** indicates P values <0.0001 of PzE-immunized serum compared to that of PBS control.

PzE-Induced Neutralization Titers Exceed the Threshold that Correlates with Protective Immunity Against ZIKV Recent studies have established that vaccine-evoked anti-zE IgG alone is sufficient to provide protection against multiple strains of ZIKV infection and protection in mice correlates with zE-specific neutralization antibody titers of >10. A plaque reduction neutralization test (PRNT) assay was performed to determine the neutralization titers of anti-zE IgG in sera from vaccinated mice. No reduction in ZIKV infection was detected for sera from mice injected with PBS (FIG. 17). In contrast, sera from mice receiving PzE exhibited potent neutralizing activities against ZIKV infection as early as week 5 (P<0.0001 comparing anti-PzE sera versus PBS sera) (FIG. 17). Importantly, greater than 68% and 84% of ZIKV infection was reduced by sera from PzE-vaccinated mice that have been diluted by 320- and 80-folds, respectively (FIG. 17). These results indicate that PzE induced a neutralization titer that is greater than 320, significantly exceeding the threshold (>10) that has been established for conferring protection against multiple strains of ZIKV.

Discussion

The explosion of the number of ZIKV cases and the association of ZIKV with the development of microcephaly in human foetuses and Guillain-Barre' syndrome in adults ignited a pressing need for potent and safe ZIKV vaccines. While these candidates are promising, alternative vaccine platforms are needed to further improve the safety and affordability of ZIKV vaccines. For example, protein-based subunit vaccines will significantly reduce risk factors associated with incomplete inactivation of live ZIKV, risks of oncogenesis as a result of genome insertion by DNA vaccines and unfavorable host responses to viral vectors (Moyle and Toth, 2013). The global ZIKV epidemic also underscores the need of production platforms that can bring the vaccines to the market with speed, scale and cost-effectiveness.

Similar to other flaviviruses, zE is a major target of host antibody responses and has been shown to contain multiple epitopes of potently neutralizing antibodies against ZIKV. In this study, the inventors examined the capability of plants in producing zE and characterized the immunogenicity of PzE. Our results indicated that zE was robustly expressed in *N. benthamiana* leaves within a week of introduction of the zE gene construct. PzE was also easily enriched from plants to >90% purity by a scalable purification regime. Further analysis indicated that PzE folded properly as it was specifically recognized by a panel of mAbs that bind to various conformational epitopes of zE. This indicates the preservation of key ZIKV neutralization determinants in our PzE preparations.

Recent studies with inactivated ZIKV and DNA vaccines have established that protection against ZIKV infection in mice and non-human primates can be mediated by vaccine-elicited anti-zE IgG alone, and protective immunity correlates with zE-specific antibody titers (log titers >2.3-3.2) and neutralization antibody titers (>10). Even though these correlations were established with the Puerto Rican strain of ZIKV (PRVABC59), it was shown that antibody responses that met these thresholds also protected animals against other strains of ZIKV including the robust Brazilian strain (Brazil ZKV2015). Our results demonstrated that PzE was highly immunogenic and induced a potent zE-specific humoral response, as well as a ZIKV-neutralizing antibody response. Specifically, zE-specific IgG log titers at week 2 (2 weeks after the first PzE injection) and week 5 (2 weeks after the first boost) were as high as >3.4 and >5.3, respectively, higher than those induced by inactivated ZIKV or DNA-based vaccines. Our results also indicated that two doses of PzE are sufficient in inducing the potent IgG response as the IgG titer after the third antigen delivery was higher but without statistical significance. The inventors found that the anti-zE titers are higher than that of anti-zEDIII. This suggests that anti-zEDI/zEDII antibodies were also elicited. This is encouraging as epitopes of potently neutralizing antibodies have been recently mapped to zEDI/zEDII in addition to zEDIII. To ensure the comparability between our results and published data, the same PRVABC59 ZIKV strain as in previous studies was used to examine ZIKV neutralization titers of PzE-induced antibodies. Our results revealed that the neutralization titer of anti-PzE sera was minimally >320 at week 5, significantly exceeding the threshold (>10) for conferring protection against multiple strains of ZIKV. To the best of our knowledge, this is the first demonstration that immunization of recombinant zE elicited a potent humoral response that exceeded the required threshold that correlates with protective immunity against ZIKV. This suggests that our PzE immunization regime has better potency in eliciting IgG response against ZIKV than the reported DNA or inactivated virus-based vaccines and may also protect mice from lethal ZIKV challenges in vivo.

In addition to a potent humoral response, PzE also elicited a robust cellular immune response. This indicates that PzE could potentially contribute to clear ZIKV infection, as well as to provide sterilizing immunity. In this study, alum was chosen as the adjuvant because it has been approved for human applications. Co-delivery of PzE with alum elicited both IgG1 and IgG2c, indicating a mixed Th1/Th2 humoral response. PzE with alum also evoked a significant and mixed Th1/Th2 cellular immune response, corroborating the results from the humoral response studies. Together, the robust production of both Th1 and Th2 types of IgGs and cytokines indicated the induction of potent and mixed Th1/Th2-type immune responses by PzE. Generally, a Th1 or Th1/Th2 mixed response is more preferable than a Th2 type for preventing and treating viral infection, further supporting the effectiveness of PzE and alum as a vaccine. Vaccine-induced antibody responses with neutralizing titers >10 have been found to correlate with protection in humans against YFV and TBEV. The ability of PzE with alum, an approved human adjuvant, in evoking neutralizing anti-body titers of >320 suggests the potential for human application of PzE-based vaccines.

Compared with the published naked plasmid, adenovirus-vectored DNA and inactivated ZIKV-based vaccine candidates, PzE has several advantages in both safety and cost. PzE will be safer than inactivated virus-based vaccines, as the risk of incomplete inactivation of live virus is completely eliminated. As a protein-based subunit vaccine, PzE does not cause genome insertion, a risk associated with DNA-based vaccines. PzE will also have a better safety profile than adenovirus-vectored ZIKV vaccines due to the elimination of potential unfavorable host responses to viral vectors. Addressing these safety issues is particularly important for the development of ZIKV vaccines because pregnant women may make up a large portion of the target population. Engineering mutations in or near the FL of EDII including a combination of mutations comprising but not limited to T76R, Q77E, W101R and L107R (SEQ ID NO: 14) eliminates the likelihood of inducing cross-reactive FL-specific antibodies. These cross-reactive FL-specific antibodies may enhance DENV or WNV infection and disease via antibody-dependent enhancement (ADE).

The successful plant production of PzE also provides an opportunity to address the economic issues of ZIKV vaccine production. Extensive evidence has shown that plants can produce large amount biomass and recombinant proteins with infrastructures that are less capital-demanding than cell-culture facilities and bioreactors. Recent studies have confirmed the long-held belief that it can be more economical to produce biologics by plant-based systems than by traditional platforms. For example, the cost of upstream production can be lowered to $1.00-2.00 per kilogram of protein using plant-based systems for certain biologics. Our results revealed that zE has accumulated rapidly and efficiently in *N. benthamiana* leaves, with expression levels comparable to that of previously reported plant recombinant proteins that are produced under nonoptimized conditions. This expression level under a small-scale laboratory condition can be further increased by process optimization of plant growth conditions and transgene optimization. Moreover, our demonstration of facile purification of PzE by a simple and scalable purification scheme further supports the feasibility of manufacturing PzE with favorable cost and scalability.

Plant-based production of zE may also provide the opportunity to explore the possibility of developing oral vaccines against ZIKV. Oral administration of zE produced in edible plants will eliminate the need for the costly downstream process, the cold chain for vaccine transport and storage, and sterile needles for injection. This will further enhance the affordability of ZIKV vaccines in resource-poor countries. While appealing, oral delivery of vaccines has been difficult due to problems of vaccine denaturation and degradation in the digestive system and their inability to cross the gut epithelium to reach target cells. However, plant cells may provide a solution to these difficulties through bioencapsulation because plant cell wall (i.e. glycosidic bonds in cellulose) is resistant to human digestive enzymes. Thus, plant cells can protect encapsulated vaccines from acids and enzymes in the stomach and allow them to enter the gut lumen where they are enzymatically released by gut commensal bacteria. Indeed, a study with tobacco chloroplast-produced polio virus viral protein 1 (VP1) showed that oral boosting of VP1 after a single priming of inactivated poliovirus significantly enhanced the VP1-specific IgG1 and IgA titers and neutralizing antibody responses in mice. Furthermore, VP1 in lyophilized plant tissue maintained long-term stability and antigenicity at ambient temperature, effectively eliminating the requirement for cold chain. Edible plants such as lettuce may offer a more palatable choice for the production of oral vaccines. Notably, a very recent publication demonstrated that oral administration of lettuce-derived hepatitis C virus E1E2 dimers following an intramuscular priming elicited both systemic and mucosal immune responses. This result illuminates the feasibility of producing E protein-based oral vaccines for Flaviviridae viruses including ZIKV. These striking developments encourage the exploration of using edible plants to produce zE-based oral vaccines to circumvent logistic challenges and allow practical implementation of ZIKV immunization programs in resource-poor regions, where the majority of ZIKV cases exists.

In summary, the inventors have demonstrated the successful production of zE in plants, its proper folding and facile purification, and most importantly, its potent immunogenicity that exceeds the established parameters that correlate with protective immunity against multiple ZIKV strains. To our knowledge, this is the first demonstration of zE-based protein vaccine regardless of the expression system that elicits neutralizing immunity. This warrants further ZIKV challenge studies in animal models to ultimately lead to the development of plant-based ZIKV vaccines with potency, enhanced safety and affordability.

While the preferred embodiments of the present technology have been illustrated in detail, it should be apparent that modifications and adaptations to those embodiments may occur to one skilled in the art without departing from the scope of the present technology.

What is claimed is:

1. An immunogenic composition comprising virus like particles (VLPs) comprising a fusion protein, wherein the fusion protein comprises (i) at least a portion of ZIKA virus envelope (E) protein domain III (zDIII) polypeptide and (ii) at least a portion of a Hepatitis B core Antigen (HBcAg) capable of forming a VLP.

2. The immunogenic composition of claim 1, wherein the portion of zDIII polypeptide comprises a sequence selected from the group consisting of SEQ ID NO: 1, SEQ ID NO: 7, SEQ ID NO: 8, SEQ ID NO: 9, SEQ ID NO: 10, SEQ ID NO: 11, and SEQ ID NO: 12.

3. The immunogenic composition of claim 1, wherein the portion of zDIII polypeptide comprises the sequence of SEQ ID NO: 1.

4. The immunogenic composition of claim 1, wherein the HBcAg comprises the sequence of SEQ ID NO: 2.

5. The immunogenic composition of claim 1, further comprising at least one of an immunological adjuvant, a pharmaceutically acceptable carrier, a buffer, or a stabilizer.

6. A method for eliciting an immunological response in a subject against ZIKA virus infection, the method comprising administering to the subject a therapeutically effective amount of the immunogenic composition of claim 1, whereby the immunogenic composition elicits an immunological response against ZIKA virus infection in the subject.

7. The method of claim 6, wherein the portion of zDIII polypeptide comprises a sequence selected from the group consisting of SEQ ID NO: 1, SEQ ID NO: 7, SEQ ID NO: 8, SEQ ID NO: 9, SEQ ID NO: 10, SEQ ID NO: 11, and SEQ ID NO: 12.

8. The method of claim 6, wherein the portion of zDIII polypeptide comprises the sequence of SEQ ID NO: 1.

9. A method for inhibiting ZIKA virus replication in a subject, the method comprising administering to the subject a therapeutically effective amount of the immunogenic composition of claim 1, whereby the immunogenic composition inhibits ZIKA virus replication in the subject.

10. The method of claim 9, wherein the portion of zDIII polypeptide comprises a sequence selected from the group consisting of SEQ ID NO: 1, SEQ ID NO: 7, SEQ ID NO: 8, SEQ ID NO: 9, SEQ ID NO: 10, SEQ ID NO: 11, and SEQ ID NO: 12.

11. The method of claim 9, wherein the portion of zDIII polypeptide comprises the sequence of SEQ ID NO: 1.

* * * * *

UNITED STATES PATENT AND TRADEMARK OFFICE
CERTIFICATE OF CORRECTION

PATENT NO. : 11,078,491 B2
APPLICATION NO. : 15/989060
DATED : August 3, 2021
INVENTOR(S) : Qiang Chen et al.

It is certified that error appears in the above-identified patent and that said Letters Patent is hereby corrected as shown below:

In the Specification

Column 33, Line 44, "Q3" should be --Qβ--.

Column 38, Line 27, "C02" should be --$CO_2$--.

Signed and Sealed this
Nineteenth Day of July, 2022

Katherine Kelly Vidal
*Director of the United States Patent and Trademark Office*